United States Patent
Kawashima et al.

(10) Patent No.: US 8,470,947 B2
(45) Date of Patent: Jun. 25, 2013

(54) ETHYLENIC POLYMER

(75) Inventors: Yasutoyo Kawashima, Pasadena, CA (US); Takahiro Hino, Chiba (JP); Taichi Senda, Takatsuki (JP)

(73) Assignee: Sumitomo Chemical Company, Limited, Tokyo (JP)

(*) Notice: Subject to any disclaimer, the term of this patent is extended or adjusted under 35 U.S.C. 154(b) by 0 days.

(21) Appl. No.: 13/498,075

(22) PCT Filed: Sep. 30, 2010

(86) PCT No.: PCT/JP2010/067130
§ 371 (c)(1),
(2), (4) Date: Mar. 23, 2012

(87) PCT Pub. No.: WO2011/040557
PCT Pub. Date: Apr. 7, 2011

(65) Prior Publication Data
US 2013/0005931 A1 Jan. 3, 2013

(30) Foreign Application Priority Data

Sep. 30, 2009 (JP) ................................ 2009-226685
Oct. 6, 2009 (JP) ................................ 2009-232247

(51) Int. Cl.
*C08F 10/02* (2006.01)
*C08F 4/6592* (2006.01)

(52) U.S. Cl.
USPC ...... 526/352; 526/348; 526/348.2; 526/348.6; 526/160; 526/170; 526/943; 526/113

(58) Field of Classification Search
USPC ............................ 526/348, 348.2, 348.6, 352
See application file for complete search history.

(56) References Cited

U.S. PATENT DOCUMENTS

| | | | |
|---|---|---|---|
| 6,121,402 A | 9/2000 | Machida et al. | |
| 6,329,478 B1 | 12/2001 | Katayama et al. | |
| 2004/0097772 A1 | 5/2004 | Deckers et al. | |
| 2004/0220359 A1 | 11/2004 | Abhari et al. | |
| 2004/0249046 A1 | 12/2004 | Abhari et al. | |
| 2006/0089417 A1 | 4/2006 | Hisayama et al. | |
| 2007/0037913 A1 | 2/2007 | Heck | |
| 2007/0037914 A1 | 2/2007 | Heck et al. | |
| 2007/0244286 A1 | 10/2007 | Okamoto et al. | |
| 2007/0293640 A1 | 12/2007 | Jiang et al. | |
| 2009/0069475 A1 | 3/2009 | Jiang et al. | |
| 2009/0149604 A1 | 6/2009 | Abhari et al. | |

FOREIGN PATENT DOCUMENTS

| | | | |
|---|---|---|---|
| JP | 07-082322 A | | 3/1995 |
| JP | 08-333407 A | | 12/1996 |
| JP | 09-087313 A | | 3/1997 |
| JP | 2004-524959 A | | 8/2004 |
| JP | 2004-306014 A | | 11/2004 |
| JP | 2005-248013 | * | 9/2005 |
| JP | 2005-248013 A | | 9/2005 |
| JP | 2006-002057 A | | 1/2006 |
| JP | 2006-504858 A | | 2/2006 |
| JP | 2006-083370 A | | 3/2006 |
| JP | 2006-152271 A | | 6/2006 |
| JP | 2006-193605 A | | 7/2006 |
| JP | 2008-546891 A | | 12/2008 |

OTHER PUBLICATIONS

Machine translation of JP 2005-248013, Sep. 2005.*
Int'l Search Report issued Dec. 28, 2010 in Int'l Application No. PCT/JP2010/067130.
Deckers et al, "Catalytic Trimerization of Ethene with Highly Active Cyclopentadienyl-Arene Titanium Catalysts," Organometallics, vol. 21, pp. 5122-5135 (2002).
Wang et al, "Catalytic Trimerization of Ethylene with Highly Active Half-sandwich Titanium Complexes Bearing Pendant p-Fluorophenyl Groups," Chinese Journal of Chemistry, vol. 24, pp. 1397-1401 (2006).
Alobaidi et al, "Direct Synthesis of Linear Low-Density Polyethylene of Ethylene/1-Hexene from Ethylene with a Tandem Catalytic System in a Single Reactor," Journal of Polymer Science Part A: Polymer Chemistry, vol. 42, pp. 4327-4336 (2004).
Int'l Search Report issued Oct. 26, 2010 in Int'l Application No. PCT/JP2010/067128.
Ye et al, "A Tandem Catalytic System for the Synthesis of Ethylene-Hex-1-ene Copolymers from Ethylene Stock," Macromolecular Rapid Communications, vol. 25, pp. 647-652 (2004).
Sassmannshausen et al, "Half-sandwich complexes of titanium and zirconium with pendant phenyl substituents. The influence of ansa-aryl coordination on the polymerisation activity of half-sandwich catalysts," Journal of Organometallic Chemistry, vol. 592, pp. 84-94 (1999).

* cited by examiner

*Primary Examiner* — Roberto Rabago
(74) *Attorney, Agent, or Firm* — Panitch Schwarze Belisario & Nadel LLP

(57) ABSTRACT

Disclosed is an ethylenic polymer having a long characteristic relaxation time. The ethylenic polymer satisfies the following requirements:
(a) the ethylenic polymer is a non-crosslinked ethylenic polymer;
(b) the number of long-chain branches (LCB) per 1000 carbon atoms is 0.1-1.5 inclusive;
(c) the intrinsic viscosity [η] is 1.0-3.0 dl/g inclusive; and
(d) the ratio (G'/G") of the storage modulus (G') to the loss modulus (G"), determined by dynamic viscoelasticity measurement at 190° C. and at an angular frequency of 0.1 rad/sec is 0.8 or more and 4.0 or less.

1 Claim, No Drawings

ETHYLENIC POLYMER

CROSS-REFERENCE TO RELATED APPLICATION

This application is a Section 371 of International Application No. PCT/JP2010/067130, filed Sep. 30, 2010, which was published in the Japanese language on Apr. 7, 2011, under International Publication No. WO 2011/040557 A1, and the disclosure of which is incorporated herein by reference.

TECHNICAL FIELD

The present invention relates to an ethylenic polymer.

BACKGROUND ART

An olefin polymer such as an ethylenic polymer is molded into a bottle, foam, sheet, film, oriented film, etc. by various molding methods such as blow molding, expansion molding and film molding, and applied to various uses such as food packaging materials.

The oriented film is often applied to uses such as a shrink packaging film and the ethylenic polymer to be applied hereto is required to have a polymer chain that is easily oriented by stretching for molding a film, in other words, to have a long characteristic relaxation time.

As such an ethylenic polymer, an ethylene-α-olefin copolymer having a flow activation energy of 50 kJ/mol or more and satisfying a specific relationship between the melt-flow rate and the melt viscosity at the shearing rate of 100 rad/sec and at 190° C. has been proposed (see, for example, Patent Document 1).

CITATION LIST

Patent Document

PATENT DOCUMENT 1: JP 2006-193605A

SUMMARY OF THE INVENTION

Problem to be Solved by the Invention

However, in the method proposed in Patent Document 1, the characteristic relaxation time was not necessarily long.

In the circumstance, an object to be achieved by the present invention is to provide an ethylenic polymer having a long characteristic relaxation time.

Means for Solving the Problem

The present invention relates to an ethylenic polymer satisfying the following requirements:

(a) the ethylenic polymer is a non-crosslinked ethylenic polymer;

(b) the number of long-chain branches (LCB) per 1000 carbon atoms is 0.1 or more and 1.5 or less;

(c) the intrinsic viscosity [η] is 1.0 dl/g or more and 3.0 dl/g or less; and (d) the ratio (G'/G") of the storage modulus (G') to the loss modulus (G"), determined by dynamic viscoelasticity measurement at 190° C. and at an angular frequency of 0.1 rad/sec is 0.8 or more and 4.0 or less.

Effect of the Invention

According to the present invention, an ethylenic polymer having a long characteristic relaxation time can be provided.

In addition, since the ethylenic polymer of the present invention has a high storage modulus (G') in its molten stage, the resultant molded articles obtained by blow molding has superior appearance and surface gloss and, regarding the processability in the foam molding and so on the cells of the obtained foam exhibit superior uniformity.

Furthermore, the ethylenic polymer of the present invention has superior performance in modifying strain hardening properties when it is blended with a resin known in the art. For example, when the ethylenic polymer of the present invention is blended with a linear polyethylene, the strain hardening property of the linear polyethylene can be improved. Furthermore, since the ethylenic polymer of the present invention is a non-crosslinked ethylenic polymer and does not form a gel, the ethylenic polymer is superior in mixing properties when it is blended with a resin known in the art.

DESCRIPTION OF EMBODIMENTS

In the present invention, the term "polymerization" includes not only homopolymerization but also copolymerization. Furthermore, in the present invention, the term "substituent" includes a halogen atom that constitutes a compound or a group.

<Polymer>

Examples of the ethylenic polymer obtained by the manufacturing method of the present invention include an ethylene homopolymer, an ethylene-1-hexene copolymer, an ethylene-1-hexene-propylene copolymer, an ethylene-1-hexene-1-butene copolymer, an ethylene-1-hexene-1-octene copolymer, an ethylene-1-hexene-4-methyl-1-pentene copolymer, an ethylene-1-hexene-1-butene-1-octene copolymer, an ethylene-1-hexene-1-butene-4-methyl-1-pentene copolymer, ethylene-1-hexene-styrene copolymer, an ethylene-1-hexene-norbornene copolymer, an ethylene-1-hexene-propylene-styrene copolymer and an ethylene-1-hexene-propylene-norbornene copolymer.

Preferable examples of the ethylenic polymer of the present invention include an ethylene homopolymer, an ethylene-1-hexene copolymer, an ethylene-1-hexene-propylene copolymer, an ethylene-1-hexene-1-butene copolymer, an ethylene-1-hexene-1-octene copolymer, an ethylene-1-hexene-4-methyl-1-pentene copolymer, an ethylene-1-hexene-styrene copolymer, an ethylene-1-hexene-norbornene copolymer. More preferable examples include an ethylene homopolymer, an ethylene-1-hexene copolymer and an ethylene-1-hexene-1-butene copolymer.

The number of long chain branches per 1000 carbon atoms of the ethylenic polymer of the present invention is 0.1 or more in view of reducing extrusion load during processing, more preferably 0.3 or more and further preferably 0.5 or more, wherein the branches have 7 or more carbon atoms, hereinafter also referred to as "LCB". Furthermore, in view of improving mechanical strength of the obtained molding, the number of LCB is 1.5 or less. The number of LCB can be determined by a carbon nuclear magnetic resonance ($^{13}$C-NMR) method.

The number of LCB can be changed by, for example, varying polymerization conditions such as hydrogen concentration and ethylene pressure, by varying the molar ratio of transition metal complex (1) to transition metal complex (5) (transition metal complex (1)/transition metal complex (5)), by varying the concentration of a catalyst for olefin polymerization in the polymerization process and the like. For example, the number of LCB can be increased by increasing the molar ratio of (transition metal complex (1)/transition metal complex (5)). Also, the number of LCB can be increased by increasing the concentration of the transition metal complex.

The intrinsic viscosity [η] of the ethylenic polymer of the present invention is 1.0 dl/g or more and 3.0 dl/g or less. To improve the mechanical strength of the ethylenic polymer, the intrinsic viscosity [η] of the ethylenic polymer is preferably 1.1 dl/g or more, more preferably 1.2 dl/g or more and further preferably 1.5 dl/g or more. Furthermore, in view of reducing extrusion load during processing, the intrinsic viscosity [η] is preferably 2.8 dl/g or less and more preferably 2.5 dl/g or less. The intrinsic viscosity [η] is measured by an Ubbelohde viscometer. The intrinsic viscosity [η] can be changed by varying polymerization conditions such as hydrogen concentration and ethylene pressure. The value of [η] can be reduced by increasing, for example, the hydrogen concentration during the polymerization process; and can be increased by decreasing the hydrogen concentration during the polymerization process.

The Ea of the ethylenic polymer of the present invention is usually 50 kJ/mol or more and 200 kJ/mol or less. In view of further reducing extrusion load during the processing, Ea is preferably 60 kJ/mol or more, more preferably 80 kJ/mol or more and particularly preferably 100 kJ/mol or more. Furthermore, to increase the gloss of blow molded articles, Ea is preferably 180 kJ/mol or less, more preferably 160 kJ/mol or less and further preferably 140 kJ/mol or less. Ea can be determined by measuring melt complex viscosity-angular frequency curves of the polymer at a plurality of temperatures by use of a viscoelasticity measurement apparatus and applying the temperature-time superposition principle to the melt complex viscosity-angular frequency curves. Ea can be controlled by changing the molar ratio of transition metal complex (1) to transition metal complex (5), changing the concentration of the catalyst for olefin polymerization in the polymerization process and so on.

The ratio (G'/G") of the storage modulus (hereinafter, also referred to as "G'"; the unit thereof is Pa) to the loss modulus (hereinafter, also referred to as "G''"; the unit thereof is Pa) of the ethylenic polymer of the present invention, is usually 0.8 or more and 4.0 or less, wherein they are determined by dynamic viscoelasticity measurement at 190° C. and at an angular frequency (hereinafter, also referred to as "ω"; and the unit thereof is rad/sec.) of 0.1.

In view of increasing the characteristic relaxation time, the ratio is preferably 1.0 or more and more preferably 1.1 or more. Furthermore, in view of reducing extrusion load during molding, the ratio is usually 3.0 or less and preferably 2.0 or less. The value of (G'/G") can be changed by varying polymerization conditions such as hydrogen concentration and ethylene pressure. The (G'/G") value can be increased by reducing the hydrogen concentration during the polymerization process and decreased by increasing the hydrogen concentration during the polymerization process.

The relationship between the storage modulus (G') and the loss modulus (G") of the ethylenic polymer of the present invention determined by dynamic viscoelasticity measurement at 190° C. preferably always satisfies G'>G" in the range of the angular frequency (hereinafter, also referred to as "ω" and the unit thereof is rad/sec) of 0.1 to 10000.

Thus, the angular frequency (hereinafter, also referred to as "$ω_x$"), at which the storage modulus (G') is crossed with the loss modulus (G"), is preferably 0.1 or less.

The storage modulus (G') value (unit: Pa) of the ethylenic polymer of the present invention at 190° C. and at the angular frequency (hereinafter, also referred to as "co"; the unit thereof is rad/sec) of 0.1 rad/second determined by dynamic viscoelasticity measurement is usually 5000 or more and 100000 or less. In view of improving surface gloss of blow molded articles, the storage modulus (G') value is preferably 7000 or more, more preferably 8000 or more and further preferably 10000 or more. In view of reducing the extrusion load during the molding, the storage modulus (G') value is preferably 70000 or less, more preferably 50000 or less and further preferably 30000 or less.

The molecular weight distribution (Mw/Mn) of the ethylenic polymer of the present invention is preferably 2 or more, in view of improving the processability (blow moldability) of the polymer, and more preferably 3 or more. Furthermore, to improve the mechanical strength of the polymer, Mw/Mn is preferably 30 or less and more preferably 15 or less. The molecular weight distribution (Mw/Mn) is determined by obtaining weight-average molecular weight (Mw) and number average molecular weight (Mn) in terms of polystyrene standard by gel permeation chromatography and dividing Mw by Mn. Mw/Mn can be increased by changing the hydrogen concentration at the polymerization field during the polymerization process.

The molecular weight distribution (Mz/Mw), which is represented by the ratio of the z-average molecular weight (Mz) to the weight-average molecular weight (Mw) of the ethylenic polymer of the present invention, is usually 2.5 or more and 10 or less. To improve the processability of the polymer, the molecular weight distribution (Mz/Mw) is preferably 3 or more. Furthermore, to improve the mechanical strength of the polymer, the molecular weight distribution (Mz/Mw) is preferably 8 or less. The molecular weight distribution (Mz/Mw) is determined by obtaining z-average molecular weight (Mz) and weight-average molecular weight (Mw) in terms of polystyrene standard by gel permeation chromatography and dividing Mz by Mw.

The number of short-chain branches per 1000 carbon atoms of the ethylenic polymer of the present invention is usually 0.5 or more and 30 or less, wherein the branches have 6 or less carbon atoms; hereinafter also referred to as "SCB". To improve the mechanical strength of the polymer, the number of short-chain branches is preferably 1 or more and more preferably 3 or more. Furthermore, to improve the rigidity of the polymer, the number of short-chain branches is preferably 25 or less, more preferably 20 or less and particularly preferably 15 or less. The number of short-chain branches can be obtained by a carbon nuclear magnetic resonance ($^{13}$C-NMR) method. The number of short-chain branches can be controlled by changing the amount of α-olefin to be copolymerized.

As the species of the short-chain branch, butyl branch and hexyl branch are preferable.

The ethylenic polymer of the present invention is formed into various molded articles (e.g., films, sheets, containers (bottles, trays, etc.)) by a molding method known in the art, for example, extrusion molding method such as blown film process and flat die process; blow molding method; injection molding method; compression molding method; and crosslinking foam molding method, and then put in use.

The ethylenic polymer of the present invention may be molded in the form of a composition blended with a resin known in the art. Furthermore, the molded article may be a single-layer molded article containing the ethylenic polymer or a multi-layer molded article having a layer containing the ethylenic polymer.

Examples of the composition in which the ethylenic polymer of the present invention is blended with a resin known in the art include a composition in which the ethylenic polymer of the present invention is blended with a linear polyethylene.

The examples of the linear polyethylene include an ethylene-α-olefin copolymer which is produced by copolymerizing ethylene with an α-olefin by a polymerization method known in the art, such as liquid-phase polymerization method, slurry polymerization method, gas phase polymerization method and high-pressure ion polymerization method, using a catalyst for olefin polymerization known in the art, such as a Ziegler catalyst and a metallocene catalyst (preferably a catalyst using an unbridged metallocene complex). These polymerization methods may be either of a batch polymerization method and a continuous polymerization method or may be a multi-stage polymerization method consisting of two-stages or more. Furthermore, a commercially available linear polyethylene may be used.

The content of the ethylenic polymer of the present invention in the composition, in which the ethylenic polymer of the present invention and a linear polyethylene are blended, is usually 0.1 wt % or more and 20 wt % or less. In view of improving the strain hardening ability of the composition, the content of the ethylenic polymer is preferably 1 wt % or more and more preferably 2 wt % or more. In view of reducing the amount of the ethylenic polymer to be used, the content of the ethylenic polymer is preferably 15 wt % or less and more preferably 10 wt % or less.

The density of the linear polyethylene is usually 890 to 960 kg/m$^3$. In view of improving the stiffness property of the composition, the density of the linear polyethylene is preferably 900 kg/m$^3$ or more, and more preferably 910 kg/m$^3$ or more. In view of improving the mechanical strength of the composition, the density of the linear polyethylene is preferably 950 kg/m$^3$ or less, and more preferably 940 kg/m$^3$ or less.

The melt-flow rate (MFR) of the linear polyethylene is usually 0.1 to 10 g/10 minutes. In view of decreasing the extrusion load during the processing, the melt-flow rate (MFR) is preferably 0.5 g/10 minutes or more. In view of improving the mechanical strength of the composition, the melt-flow rate (MFR) is preferably 5 g/10 minutes or less.

The flow activation energy (Ea) of the linear polyethylene is less than 50 kJ/mol, preferably less than 35 kJ/mol, and more preferably less than 30 kJ/mol.

The ethylenic polymer of the present invention is a non-crosslinked polymer. The "crosslinked polymer" mentioned herein represents a structure having a network structure, which is given by purposely introducing a physical bond between molecular chains with the help of an electron beam, a peroxide or heat. The crosslinked product of the ethylenic polymer is a crosslinked product having a gel structure, which is present as an insoluble portion when the ethylenic polymer is dissolved in an ethylenic polymer-soluble organic solvent such as heated xylene. Since the ethylenic polymer of the present invention is a non-crosslinked polymer and thus substantially has no gel structure, the ethylenic polymer of the present invention is excellent in miscibility when it is blended with another resin, compared to a crosslinked ethylenic polymer.

Examples of the molded articles include films for food packaging, containers for food packaging, packaging materials for pharmaceuticals, surface-protective films, packaging materials for electronic parts used in packages for semiconductor products or the like, cross-linking foam moldings, extrusion foam moldings, blow molded articles, blow bottles and squeeze bottles.

Examples of a method for producing the ethylenic polymer of the present invention include a method using a catalyst obtained by bringing transition metal complex (1), transition metal complex (5) and an activating co-catalyst component into contact with each other.

<Transition Metal Complex (1)>

Examples of the transition metal complex (1) include a transition metal complex represented by the following general formula (1).

[Formula 1]

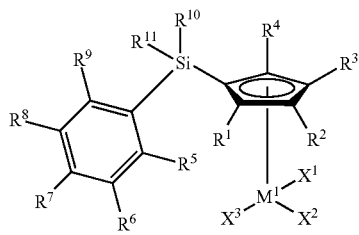

(1)

[In the formula, M$^1$ represents a transition metal atom of Group 4 of the Periodic Table of the Elements; R$^1$, R$^2$, R$^3$ and R$^4$ each independently represent hydrogen atom, a halogen atom,
an alkyl group having 1 to 20 carbon atoms which may have a halogen atom as a substituent,
an alkoxy group having 1 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent,
a substituted silyl group represented by —Si(R$^{12}$)$_3$, wherein the three R$^{12}$ groups each independently represent hydrogen atom, a hydrocarbyl group or a hydrocarbyl halide group, and the total number of the carbon atoms in the three R$^{12}$ groups is 1 to 20,
or a disubstituted amino group represented by —N(R$^{13}$)$_2$, wherein the two R$^{13}$ groups each independently represent a hydrocarbyl group or a hydrocarbyl halide group, and the total number of the carbon atoms in the two R$^{13}$ groups is 2 to 20;
at least one of R$^1$, R$^2$, R$^3$ and R$^4$ is a halogen atom, said alkyl group, said alkoxy group, said aryl group, said aryloxy group, said aralkyl group, said aralkyloxy group, said substituted silyl group or said disubstituted amino group;
R$^5$ and R$^9$ each independently represent
hydrogen atom, a halogen atom,
an alkyl group having 1 to 20 carbon atoms which may have a halogen atom as a substituent,
an alkoxy group having 2 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent,
a substituted silyl group represented by —Si(R$^{12}$)$_3$, wherein the three R$^{12}$ groups each independently represent hydrogen atom, a hydrocarbyl group or a hydrocarbyl halide group, and the total number of the carbon atoms in the three R$^{12}$ groups is 1 to 20,
or a disubstituted amino group represented by —N(R$^{13}$)$_2$, wherein the two R$^{13}$ groups each independently represent a hydrocarbyl group or a hydrocarbyl halide group, and the total number of the carbon atoms in the two R$^{13}$ groups is 2 to 20;
R$^6$, R$^7$ and R$^8$ each independently represent
hydrogen atom, a halogen atom,
an alkyl group having 1 to 20 carbon atoms which may have a halogen atom as a substituent, an alkoxy group having 1 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent,
a substituted silyl group represented by —Si($R^{12}$)$_3$, wherein the three $R^{12}$ groups each independently represent hydrogen atom, a hydrocarbyl group or a hydrocarbyl halide group, and the total number of the carbon atoms in the three $R^{12}$ groups is 1 to 20,
or a disubstituted amino group represented by —N($R^{13}$)$_2$, wherein the two $R^{13}$ groups each independently represent a hydrocarbyl group or a hydrocarbyl halide group, and the total number of the carbon atoms in the two $R^{13}$ groups is 2 to 20;
$R^{10}$ and $R^{11}$ each independently,
hydrogen atom, a halogen atom,
an alkyl group having 1 to 20 carbon atoms which may have a halogen atom as a substituent,
an alkoxy group having 1 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent,
a substituted silyl group represented by —Si($R^{12}$)$_3$, wherein the three $R^{12}$ groups each independently represent hydrogen atom, a hydrocarbyl group or a hydrocarbyl halide group, and the total number of the carbon atoms in the three $R^{12}$ groups is 1 to 20,
or a disubstituted amino group represented by —N($R^{13}$)$_2$, wherein the two $R^{13}$ groups each independently represent a hydrocarbyl group or a hydrocarbyl halide group, and the total number of the carbon atoms present in the two $R^{13}$ groups is 2 to 20;
$X^1$, $X^2$ and $X^3$ each independently represent
hydrogen atom, a halogen atom,
an alkyl group having 1 to 20 carbon atoms which may have a halogen atom as a substituent,
an alkoxy group having 1 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent,
a substituted silyl group represented by —Si($R^{12}$)$_3$, wherein the three $R^{12}$ groups each independently represent hydrogen atom, a hydrocarbyl group or a hydrocarbyl halide group, and the total number of the carbon atoms in the three $R^{12}$ groups is 1 to 20,
or a disubstituted amino group represented by —N($R^{13}$)$_2$, wherein the two $R^{13}$ groups each independently represent a hydrocarbyl group or a hydrocarbyl halide group, and the total number of the carbon atoms in the two $R^{13}$ groups is 2 to 20;
of $R^1$, $R^2$, $R^3$ and $R^4$, two groups bonded to two adjacent carbon atoms may be bonded to form a ring together with the two carbon atoms to which the two groups are bonded,
of $R^5$, $R^6$, $R^7$, $R^8$ and $R^9$, two groups bonded to two adjacent carbon atoms may be bonded to form a ring together with the two carbon atoms to which these two groups are bonded; and $R^{10}$ and $R^{11}$ may be bonded to form a ring together with the silicon atom to which they are bonded.]

The transition metal complex represented by the general formula (1) will be described in detail as follows.

In the transition metal complex (1), $M^1$ represents an element of Group 4 of the Periodic Table of the Elements, such as titanium atom, zirconium atom and hafnium atom. Of these, titanium atom is preferable.

In the transition metal complex (1), substituents $R^1$, $R^2$, $R^3$, $R^4$, $R^5$, $R^6$, $R^7$, $R^8$, $R^9$, $R^{10}$, $R^{11}$, $X^1$, $X^2$ and $X^3$ are as defined above and specific examples thereof will be described below.

Examples of the halogen atom include fluorine atom, chlorine atom, bromine atom and iodine atom, and chlorine atom is preferable.

Specific examples of the "alkyl group having 1 to 20 carbon atoms" of the alkyl group having 1 to 20 carbon atoms which may have a halogen atom as a substituent include methyl group, ethyl group, n-propyl group, isopropyl group, n-butyl group, sec-butyl group, tert-butyl group, n-pentyl group, neopentyl group, amyl group, n-hexyl group, heptyl group, n-octyl group, n-nonyl group, n-decyl group, n-dodecyl group, n-tridecyl group, tetradecyl group, pentadecyl group, hexadecyl group, heptadecyl group, octadecyl group, nonadecyl group and n-eicosyl group. Of these, a preferable alkyl group is an alkyl group having 1 to 10 carbon atoms, and a further preferable alkyl group includes methyl group, ethyl group, isopropyl group, tert-butyl group and amyl group. Furthermore, "which may have a halogen atom as a substituent" of the "alkyl group which may have a halogen atom as a substituent" means that some or all hydrogen atoms in the alkyl group may be substituted with halogen atoms. Specific examples of the halogen atoms are the same as mentioned above. It should be noted that in the case of an alkyl group having a halogen atom as a substituent, the number of carbon atoms thereof preferably falls within the range of 1 to 20 and further preferably within the range of 1 to 10. Preferable examples of the alkyl group having a halogen atom as a substituent include fluoromethyl group, difluoromethyl group, trifluoromethyl group, chloromethyl group, dichloromethyl group, trichloromethyl group, bromomethyl group, dibromomethyl group, tribromomethyl group, fluoroethyl group, perfluoropropyl group, perfluorobutyl group, perfluoropentyl group and perfluorohexyl group.

Specific examples of the "aryl group having 6 to 20 carbon atoms" of the aryl group having 6 to 20 carbon atoms which may have a halogen atom as a substituent include phenyl group, 2-tolyl group, 3-tolyl group, 4-tolyl group, 2,3-xylyl group, 2,4-xylyl group, 2,5-xylyl group, 2,6-xylyl group, 3,4-xylyl group, 3,5-xylyl group, 2,3,4-trimethylphenyl group, 2,3,5-trimethylphenyl group, 2,3,6-trimethylphenyl group, 2,4,6-trimethylphenyl group, 3,4,5-trimethylphenyl group, 2,3,4,5-tetramethylphenyl group, 2,3,4,6-tetramethylphenyl group, 2,3,5,6-tetramethylphenyl group, pentamethylphenyl group, ethylphenyl group, n-propylphenyl group, isopropylphenyl group, n-butylphenyl group, sec-butylphenyl group, tert-butylphenyl group, n-pentylphenyl group, neopentylphenyl group, n-hexylphenyl group, n-octylphenyl group, n-decylphenyl group, n-dodecylphenyl group, n-tetradecylphenyl group, naphthyl group and anthracenyl group. Of these, a preferable aryl group is an aryl group having 6 to 10 carbon atoms and a further preferable aryl group is phenyl group. Furthermore, "which may have a halogen atom as a substituent" of the "aryl group which may have a halogen atom as a substituent" means that some or all hydrogen atoms in the aryl group may be substituted with halogen atoms. Specific examples of the halogen atom are the same as mentioned above. It should be noted that in the case of an aryl group having a halogen atom as a substituent, the number of carbon atoms thereof preferably falls within the range of 6 to 20 and further preferably within the range of 6 to 10. Specific examples of the preferable aryl group having a halogen atom as a substituent include fluorophenyl group, difluorophenyl group, trifluorophenyl group, tetrafluorophenyl group, pentafluorophenyl group, chlorophenyl group, bromophenyl group and iodophenyl group.

Specific examples of the aralkyl group having 7 to 20 carbon atoms" of the aralkyl group having 7 to 20 carbon atoms which may have a halogen atom as a substituent include benzyl group, (2-methylphenyl)methyl group, (3-methylphenyl)methyl group, (4-methylphenyl)methyl group, (2,3-dimethylphenyl)methyl group, (2,4-dimethylphenyl)methyl group, (2,5-dimethylphenyl)methyl group, (2,6-dimethylphenyl)methyl group, (3,4-dimethylphenyl)methyl group, (3,5-dimethylphenyl)methyl group, (2,3,4-trimethylphenyl)methyl group, (2,3,5-trimethylphenyl)methyl group, (2,3,6-trimethylphenyl)methyl group, (3,4,5-trimethylphenyl)methyl group, (2,4,6-trimethylphenyl)methyl group, (2,3,4,5-tetramethylphenyl)methyl group, (2,3,4,6-tetramethylphenyl)methyl group, (2,3,5,6-tetramethylphenyl)methyl group, (pentamethylphenyl)methyl group, (ethylphenyl)methyl group, (n-propylphenyl)methyl group, (isopropylphenyl)methyl group, (n-butylphenyl)methyl group, (sec-butylphenyl)methyl group, (tert-butylphenyl)methyl group, (n-pentylphenyl)methyl group, (neopentylphenyl)methyl group, (n-hexylphenyl)methyl group, (n-octylphenyl)methyl group, (n-decylphenyl)methyl group, (n-dodecylphenyl)methyl group, naphthylmethyl group and anthracenylmethyl group. Of these, a preferable aralkyl group is an aralkyl group having 7 to 10 carbon atoms and a further preferable aralkyl group can be benzyl group. Furthermore, "which may have a halogen atom as a substituent" of the "aralkyl group which may have a halogen atom as a substituent" means that some or all hydrogen atoms in the aralkyl group may be substituted with halogen atoms.

Specific examples of the halogen atoms are the same as mentioned above. It should be noted that in the case of an aralkyl group having a halogen atom as a substituent, the number of carbon atoms thereof preferably falls within the range of 7 to 20 and further preferably within the range of 7 to 10.

Specific examples of the "alkoxy group having 1 to 20 carbon atoms" of the alkoxy group having 1 to 20 carbon atoms which may have a halogen atom as a substituent include methoxy group, ethoxy group, n-propoxy group, isopropoxy group, n-butoxy group, sec-butoxy group, tert-butoxy group, n-pentyloxy group, neopentyloxy group, n-hexyloxy group, n-octyloxy group, n-nonyloxy group, n-decyloxy group, n-dodecyloxy group, n-undecyloxy group, n-dodecyloxy group, tridecyloxy group, tetradecyloxy group, n-pentadecyloxy group, hexadecyloxy group, heptadecyloxy group, octadecyloxy group, nonadecyloxy group and n-eicosyloxy group. Of these, a preferable alkoxy group is an alkoxy group having 1 to 10 carbon atoms, and a further preferable alkoxy group includes methoxy group, ethoxy group and tert-butoxy group. Furthermore, "which may have a halogen atom as a substituent" of the "alkoxy group which may have a halogen atom as a substituent" means that some or all hydrogen atoms in the alkoxy group may be substituted with halogen atoms. Specific examples of the halogen atoms are the same as mentioned above. It should be noted that in the case of an alkoxy group having a halogen atom as a substituent, the number of carbon atoms thereof preferably falls within the range of 1 to 20 and further preferably within the range of 1 to 10.

Specific examples of the "alkoxy group having 2 to 20 carbon atoms" of the alkoxy group having 2 to 20 carbon atoms which may have a halogen atom as a substituent include ethoxy group, n-propoxy group, isopropoxy group, n-butoxy group, sec-butoxy group, tert-butoxy group, n-pentyloxy group, neopentyloxy group, n-hexyloxy group, n-octyloxy group, n-nonyloxy group, n-decyloxy group, n-dodecyloxy group, n-undecyloxy group, n-dodecyloxy group, tridecyloxy group, tetradecyloxy group, n-pentadecyloxy group, hexadecyloxy group, heptadecyloxy group, octadecyloxy group, nonadecyloxy group and n-eicosyloxy group. Of these, a preferable alkoxy group is an alkoxy group having 2 to 10 carbon atoms. A further preferable alkoxy group includes ethoxy group and tert-butoxy group. Furthermore, "which may have a halogen atom as a substituent" of the "alkoxy group which may have a halogen atom as a substituent" means that some or all hydrogen atoms in the alkoxy group may be substituted with halogen atoms. Specific examples of the halogen atoms are the same as mentioned above. It should be noted that in the case of an alkoxy group having a halogen atom as a substituent, the number of carbon atoms thereof preferably falls within the range of 2 to 20 and further preferably within the range of 2 to 10.

Specific examples of the "aryloxy group having 6 to 20 carbon atoms" of the aryloxy group having 6 to 20 carbon atoms which may have a halogen atom as a substituent include phenoxy group, 2-methylphenoxy group, 3-methylphenoxy group, 4-methylphenoxy group, 2,3-dimethylphenoxy group, 2,4-dimethylphenoxy group, 2,5-dimethylphenoxy group, 2,6-dimethylphenoxy group, 3,4-dimethylphenoxy group, 3,5-dimethylphenoxy group, 2,3,4-trimethylphenoxy group, 2,3,5-trimethylphenoxy group, 2,3,6-trimethylphenoxy group, 2,4,5-trimethylphenoxy group, 2,4,6-trimethylphenoxy group, 3,4,5-trimethylphenoxy group, 2,3,4,5-tetramethylphenoxy group, 2,3,4,6-tetramethylphenoxy group, 2,3,5,6-tetramethylphenoxy group, pentamethylphenoxy group, ethylphenoxy group, n-propylphenoxy group, isopropylphenoxy group, n-butylphenoxy group, sec-butylphenoxy group, tert-butylphenoxy group, n-hexylphenoxy group, n-octylphenoxy group, n-decylphenoxy group, n-tetradecylphenoxy group, naphthoxy group and anthracenoxy group. Of these, a preferable aryloxy group is an aryloxy group having 6 to 10 carbon atoms, and a further preferable aryloxy group includes phenoxy group, 2-methylphenoxy group, 3-methylphenoxy group and 4-methylphenoxy group. Furthermore, "which may have a halogen atom as a substituent" of the "aryloxy group which may have a halogen atom as a substituent" means that some or all hydrogen atoms in the aryloxy group may be substituted with halogen atoms. Specific examples of the halogen atoms are the same as mentioned above. It should be noted that in the case of an aryloxy group having a halogen atom as a substituent, the number of carbon atoms thereof preferably falls within the range of 6 to 20 and further preferably within the range of 6 to 10.

Specific examples of the "aralkyloxy group having 7 to 20 carbon atoms" of the aralkyloxy group having 7 to 20 carbon atoms which may have a halogen atom as a substituent include benzyloxy group, (2-methylphenyl)methoxy group, (3-methylphenyl)methoxy group, (4-methylphenyl)methoxy group, (2,3-dimethylphenyl)methoxy group, (2,4-dimethylphenyl)methoxy group, (2,5-dimethylphenyl)methoxy group, (2,6-dimethylphenyl)methoxy group, (3,4-dimethylphenyl)methoxy group, (3,5-dimethylphenyl)methoxy group, (2,3,4-trimethylphenyl)methoxy group, (2,3,5-trimethylphenyl)methoxy group, (2,3,6-trimethylphenyl)methoxy group, (2,4,5-trimethylphenyl)methoxy group, (2,4,6-trimethylphenyl)methoxy group, (3,4,5-trimethylphenyl)methoxy group, (2,3,4,5-tetramethylphenyl)methoxy group, (2,3,4,6-tetramethylphenyl)methoxy group, (2,3,5,6-tetramethylphenyl)methoxy group, (pentamethylphenyl)methoxy group, (ethylphenyl)methoxy group, (n-propylphenyl)methoxy group, (isopropylphenyl)methoxy group, (n-butylphenyl)methoxy group, (sec-butylphenyl)methoxy group, (tert-butylphenyl)methoxy group, (n-hexylphenyl)methoxy group, (n-octylphenyl)methoxy group, (n-decylphenyl)methoxy group, naphthyl methoxy group and anthracenyl methoxy group. Of these, a preferable aralkyloxy group is an aralkyloxy group having 7 to 10 carbon atoms, and a further preferable aralkyloxy group is benzyloxy group. Furthermore, "which may have a halogen atom as a substituent" of the "aralkyloxy group which may have a halogen atom as a substituent" means that some or all hydrogen atoms in the aralkyloxy group may be substituted with halogen atoms. Specific examples of the halogen atoms are the same as mentioned above. It should be noted that in the case of an aralkyloxy group having a halogen atom as a substituent, the number of carbon atoms thereof preferably falls within the range of 7 to 20 and further preferably within the range of 7 to 10.

In a substituted silyl group represented by —Si($R^{12}$)$_3$, wherein the three $R^{12}$ groups each independently represent hydrogen atom, a hydrocarbyl group or a hydrocarbyl halide group, and the total number of the carbon atoms in the three $R^{12}$ groups is 1 to 20, the three $R^{12}$ groups are each independently hydrogen atom; a hydrocarbyl group such as an alkyl group having 1 to 10 carbon atoms (a methyl group, ethyl group, n-propyl group, isopropyl group, n-butyl group, sec-butyl group, tert-butyl group, isobutyl group, n-pentyl group, n-hexyl group, cyclohexyl group, n-heptyl group, n-octyl group, n-nonyl group, a n-decyl group, etc.) and an aryl group (a phenyl group, etc.); a hydrocarbyl halide group in which hydrogen atoms in the hydrocarbyl group are wholly or partly substituted with halogen atoms, and the total number of the carbon atoms in the three $R^{12}$ groups is within the range of 1 to 20. The total number of the carbon atoms in the three $R^{12}$ groups is preferably within the range of 3 to 18. Specific examples of the substituted silyl group include a mono-substituted silyl group having a single hydrocarbyl group or a hydrocarbyl halide group, such as methylsilyl group, ethylsilyl group, phenylsilyl group, and groups obtained by substituting some or all hydrogen atoms of a hydrocarbyl group in these groups with halogen atoms; a disubstituted silyl group having two hydrocarbyl groups and/or hydrocarbyl halide groups such as dimethylsilyl group, diethylsilyl group, diphenylsilyl group and groups obtained by substituting some or all hydrogen atoms of a hydrocarbyl group in these groups with halogen atoms; and a tri-substituted silyl group having three hydrocarbyl groups and/or hydrocarbyl halide groups such as trimethylsilyl group, triethylsilyl group, tri-n-propylsilyl group, triisopropylsilyl group, tri-n-butylsilyl group, tri-sec-butylsilyl group, tri-tert-butylsilyl group, tri-isobutylsilyl group, tert-butyl-dimethylsilyl group, tri-n-pentylsilyl group, tri-n-hexylsilyl group, tricyclohexylsilyl group, triphenylsilyl group and groups obtained by substituting some or all hydrogen atoms of a hydrocarbyl group in these groups with halogen atoms. Of these, a preferable group is a tri-substituted silyl group, and a further preferable group includes trimethylsilyl group, tert-butyldimethylsilyl group, triphenylsilyl group and groups obtained by substituting some or all hydrogen atoms of these groups with halogen atoms.

In the disubstituted amino group represented by —N($R^{13}$)$_2$, wherein the two $R^{13}$ groups each independently represent a hydrocarbyl group or a hydrocarbyl halide group, and the total number of the carbon atoms in the two $R^{13}$ groups is 2 to 20, the two $R^{13}$ groups each independently represent a hydrocarbyl group or a hydrocarbyl halide group; the total number of the carbon atoms of the two $R^{13}$ groups is within the range of 2 to 20 and is further preferably within the range of 2 to 10. Such a hydrocarbyl group and a hydrocarbyl halide group are the same as those described as a hydrocarbyl group and a hydrocarbyl halide group of the substituted silyl group. Furthermore, these two $R^8$ groups may be bonded to form a ring together with nitrogen atoms to which they are bonded. Examples of such disubstituted amino group include dimethylamino group, diethylamino group, di-n-propylamino group, diisopropylamino group, di-n-butylamino group, di-sec-butylamino group, di-tert-butylamino group, di-isobutylamino group, tert-butylisopropylamino group, di-n-hexylamino group, di-n-octylamino group, di-n-decylamino group, diphenylamino group, bistrimethylsilylamino group, bis-tert-butyldimethylsilylamino group, pyrrolyl group, pyrrolidinyl group, piperidinyl group, carbazolyl group, dihydroindolyl group, dihydroisoindolyl group and groups obtained by partly or wholly substituting hydrogen atoms of these groups with halogen atoms. Of these, a preferable group includes dimethylamino group, diethylamino group, pyrrolidinyl group piperidinyl group, and groups obtained by substituting some or all hydrogen atoms of these groups with halogen atoms.

Of $R^1$, $R^2$, $R^3$ and $R^4$, the groups bonded to adjacent two carbon atoms may be mutually bonded to form a ring together with the carbon atoms to which they are bonded; $R^{10}$ and $R^{11}$ may be bonded to form a ring together with the silicon atoms to which they are bonded. Of $R^5$, $R^6$, $R^7$, $R^8$ and $R^9$, the groups bonded to adjacent two carbon atoms may be mutually bonded to form a ring together with carbon atoms to which they are bonded. Examples of the ring mentioned herein include a saturated or unsaturated hydrocarbyl ring substituted with a hydrocarbyl group having 1 to 20 carbon atoms and a saturated or unsaturated silahydrocarbyl ring substituted with a hydrocarbyl group having 1 to 20 carbon atoms. Specific examples thereof include cyclopropane ring, cyclopropene ring, cyclobutane ring, cyclobutene ring, cyclopentane ring, cyclopentene ring, cyclohexane ring, cyclohexene ring, cycloheptane ring, cycloheptene ring, cyclooctane ring, cyclooctane ring, benzene ring, naphthalene ring, anthracene ring, silacyclopropane ring, silacyclobutane ring, silacyclopentane ring and silacyclohexane ring.

In the transition metal complex (1), at least one of $R^1$, $R^2$, $R^3$ and $R^4$ is a substituent other than hydrogen, which is preferably hydrogen atom, a halogen atom, an alkyl group having 1 to 20 carbon atoms, an aryl group having 6 to 20 carbon atoms or an aralkyl group having 7 to 20 carbon atoms.

Specific examples of the combination of $R^1$, $R^2$, $R^3$ and $R^4$ include, in the substructure represented by the formula (15)

[Formula 2]

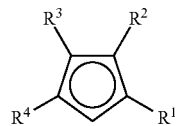

(15)

wherein $R^1$, $R^2$, $R^3$ and $R^4$ are the same as defined above, a combination providing a cyclopentadienyl substructure having at least one substituent other than hydrogen. Examples of the combination include those providing the following substructures:

methylcyclopentadienyl, ethylcyclopentadienyl, n-propylcyclopentadienyl, isopropylcyclopentadienyl, n-butylcyclopentadienyl, sec-butylcyclopentadienyl, tert-butylcyclopentadienyl, dimethylcyclopentadienyl, trimethylcyclopentadienyl, tetramethylcyclopentadienyl, phenylcyclopentadienyl, benzylcyclopentadienyl, indenyl, fluorenyl, tetrahydroindenyl, methyltetrahydroindenyl, dimethyltetrahydroindenyl and octahydrofluorenyl substructures.

Of the cyclopentadienyl substructures exemplified herein, a preferable cyclopentadienyl substructure includes tetramethylcyclopentadienyl substructure.

In the transition metal complex (1), $R^5$, $R^6$, $R^7$, $R^8$ and $R^9$ are each preferably hydrogen atom, a halogen atom, an alkyl group having 1 to 20 carbon atoms, an aryl group having 6 to 20 carbon atoms or an aralkyl group having 7 to 20 carbon atoms.

Examples of a preferable combination of $R^5$, $R^6$, $R^7$, $R^8$ and $R^9$ include combinations providing substructures containing them represented by the formula (16)

[Formula 3]

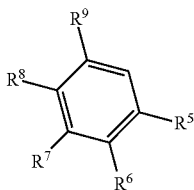
(16)

wherein $R^5$, $R^6$, $R^7$, $R^8$ and $R^9$ are the same as defined above,
such as:
phenyl, methylphenyl, dimethylphenyl, trimethylphenyl, tetramethylphenyl, pentamethylphenyl, tert-butylphenyl, di-tert-butylphenyl, tort-butylmethylphenyl, di(tert-butyl)methylphenyl, naphthyl, anthracenyl, chlorophenyl, dichlorophenyl, fluorophenyl, pentafluorophenyl, bis(trifluoromethyl)phenyl and methoxyphenyl substructures.

Of the substructure exemplified herein, preferable substructures include phenyl, methylphenyl, dimethylphenyl and trimethylphenyl.

In the transition metal complex (1), $R^{10}$ and $R^{11}$ are each preferably hydrogen atom, an alkyl group having 1 to 20 carbon atoms, an aryl group having 6 to 20 carbon atoms or an aralkyl group having 7 to 20 carbon atoms. Specific examples thereof include methyl group, ethyl group, n-propyl group, isopropyl group, n-butyl group, sec-butyl group, tert-butyl group, phenyl group, 4-methylphenyl group, 3-methylphenyl group, 2-methylphenyl group, naphthyl group and benzyl group.

Examples of a preferable combination of $R^{10}$ and $R^{11}$ include combinations providing substructures containing them represented by the formula (17):

[Formula 4]

(17)

wherein $R^{10}$ and $R^{11}$ are the same as defined above,
such as:
dimethylsilylene, diethylsilylene, ethylmethylsilylene, di(n-propyl)silylene, methyl(n-propyl)silylene, di(n-butyl)silylene, n-butylmethylsilylene, n-hexylmethylsilylene, methyl(n-octyl)silylene, n-decylmethylsilylene, methyl(n-octadecyl)silylene, cyclohexylmethylsilylene, cyclotetramethylenesilylene, diphenylsilylene and methylphenylsilylene.

A preferable substructure is a substructure represented by the formula (17) wherein
$R^{10}$ is methyl group,
$R^{11}$ is an alkyl group having 2 to 20 carbon atoms which may have a halogen atom as a substituent, or
an aryl group having 6 to 20 carbon atoms which may have a halogen atom as a substituent;
or a substructure represented by the formula (17) wherein $R^{10}$ and $R^{11}$ are the same as each other and represent an alkyl group having 1 to 20 carbon atoms which may have a halogen atom as a substituent, or
an aryl group having 6 to 20 carbon atoms which may have a halogen atom as a substituent can be preferably mentioned.

Specific examples thereof include dimethylsilylene, diethylsilylene, ethylmethylsilylene, n-butylmethylsilylene, cyclohexylmethylsilylene, cyclotetramethylenesilylene, diphenylsilylene and methylphenylsilylene.

As a transition metal complex represented by the formula (1), preferably a transition metal complex wherein $R^6$ and $R^8$ represent
an alkyl group having 1 to 20 carbon atoms which may have a halogen atom as a substituent or an aryl group having 6 to 20 carbon atoms which may have a halogen atom as a substituent; and
$R^{10}$ and $R^{11}$ represent
an aryl group having 6 to 20 carbon atoms which may have a halogen atom as a substituent, can be mentioned.

Specific examples of the transition metal complex (1) include the following complexes such as titanium chloride complexes including:
[1-dimethylphenylsilyl-2-methylcyclopentadienyl]titanium trichloride, [1-dimethylphenylsilyl-3-methylcyclopentadienyl]titanium trichloride, [1-dimethylphenylsilyl-2,3-dimethylcyclopentadienyl]titanium trichloride, [1-dimethylphenylsilyl-2,4-dimethylcyclopentadienyl]titanium trichloride, [1-dimethylphenylsilyl-2,5-dimethylcyclopentadienyl]titanium trichloride, [1-dimethylphenylsilyl-2,3,5-trimethylcyclopentadienyl]titanium trichloride, [1-dimethylphenylsilyl-2,3,4,5-tetramethylcyclopentadienyl]titanium trichloride, [1-dimethylphenylsilyl-2-ethylcyclopentadienyl]titanium trichloride, [1-dimethylphenylsilyl-3-ethylcyclopentadienyl]titanium trichloride, [1-dimethylphenylsilyl-2-n-propylcyclopentadienyl]titanium trichloride, [1-dimethylphenylsilyl-3-n-propylcyclopentadienyl]titanium trichloride, [1-dimethylphenylsilyl-2-isopropylcyclopentadienyl]titanium trichloride, [1-dimethylphenylsilyl-2-n-butylcyclopentadienyl]titanium trichloride, [1-dimethylphenylsilyl-3-n-butylcyclopentadienyl]titanium trichloride, [1-dimethylphenylsilyl-2-sec-butylcyclopentadienyl]titanium trichloride, [1-dimethylphenylsilyl-3-sec-butylcyclopentadienyl]titanium trichloride, [1-dimethylphenylsilyl-2-tert-butylcyclopentadienyl]titanium trichloride, [1-dimethylphenylsilyl-3-tert-butylcyclopentadienyl]titanium trichloride, [1-dimethylphenylsilyl-2-phenylcyclopentadienyl]titanium trichloride, [1-dimethylphenylsilyl-3-phenylcyclopentadienyl]titanium trichloride, [1-dimethylphenylsilyl-2-benzylcyclopentadienyl]titanium trichloride, [1-dimethylphenylsilyl-3-benzylcyclopentadienyl]titanium trichloride, [1-dimethylphenylsilyl-indenyl]titanium trichloride, [1-dimethylphenylsilyl-2-methylindenyl]titanium trichloride, [9-dimethylphenylsilyl-fluorenyl]titanium trichloride, [1-dimethylphenylsilyl-tetrahydroindenyl]titanium trichloride, [1-dimethylphenylsilyl-2-methyl-tetrahydroindenyl]titanium trichloride, [9-dimethylphenylsilyl-octahydrofluorenyl]titanium trichloride,
[1-diethylphenylsilyl-2-methylcyclopentadienyl]titanium trichloride, [1-diethylphenylsilyl-3-methylcyclopentadienyl]titanium trichloride, β-diethylphenylsilyl-2,3-dimethylcyclopentadienyl]titanium trichloride, [1-diethylphenylsilyl-2,4-dimethylcyclopentadienyl]titanium trichloride, [1-diethylphenylsilyl-2,5-dimethylcyclopentadienyl]titanium trichloride, [1-diethylphenylsilyl-2,3,5-trimethylcyclopentadienyl]titanium trichloride, [1-diethylphenylsilyl-2,3,4,5-tetramethylcyclopentadienyl]titanium trichloride, [1-diethylphenylsilyl-2-ethylcyclopentadienyl]titanium trichloride, [1-diethylphenylsilyl-3-ethylcyclopentadienyl]titanium trichloride, [1-diethylphenylsilyl-2-n-propylcyclopentadienyl]titanium trichloride, [1-diethylphenylsilyl-3-n-propylcyclopentadienyl]titanium trichloride, [1-diethylphenylsilyl-2-isopropylcyclopentadienyl]titanium trichloride, [1-diethylphenylsilyl-3-isopropylcyclopentadienyl]titanium trichloride, [1-diethylphenylsilyl-2-n-butylcyclopentadienyl]titanium trichloride, [1-diethylphenylsilyl-3-n-butylcyclopentadienyl]titanium trichloride, [1-diethylphenylsilyl-2-sec-butylcyclopentadienyl]titanium trichloride, [1-diethylphenylsilyl-3-sec-butylcyclopentadienyl]titanium trichloride, [1-diethylphenylsilyl-2-tert-butylcyclopentadienyl]titanium trichloride, [1-diethylphenylsilyl- 3-tert-butylcyclopentadienyl]titanium trichloride, [1-diethylphenylsilyl-2-phenylcyclopentadienyl]titanium trichloride, [1-diethylphenylsilyl-3-phenylcyclopentadienyl] titanium trichloride, [1-diethylphenylsilyl-2-benzylcyclopentadienyl]titanium trichloride, [1-diethylphenylsilyl-3-benzylcyclopentadienyl]titanium trichloride, [1-diethylphenylsilyl-indenyl]titanium trichloride, [1-diethylphenylsilyl-2-methylindenyl]titanium trichloride, [9-diethylphenylsilyl-fluorenyl]titanium trichloride, [1-diethylphenylsilyl-tetrahydroindenyl]titanium trichloride, [1-diethylphenylsilyl-2-methyltetrahydroindenyl]titanium trichloride, [9-diethylphenylsilyl-octahydrofluorenyl]titanium trichloride,
[1-cyclotetramethylene(phenyl)silyl-2-methylcyclopentadienyl]titanium trichloride, [1-cyclotetramethylene(phenyl)silyl-3-methylcyclopentadienyl]titanium trichloride, [1-cyclotetramethylene(phenyl)silyl-2,3-dimethylcyclopentadienyl]titanium trichloride, [1-cyclotetramethylene(phenyl)silyl-2,4-dimethylcyclopentadienyl]titanium trichloride, [1-cyclotetramethylene(phenyl)silyl-2,5-dimethylcyclopentadienyl]titanium trichloride, [1-cyclotetramethylene(phenyl)silyl-2,3,5-trimethylcyclopentadienyl]titanium trichloride, [1-cyclotetramethylene(phenyl)silyl-2,3,4,5-tetramethylcyclopentadienyl]titanium trichloride, [1-cyclotetramethylene(phenyl)silyl-2-ethylcyclopentadienyl]titanium trichloride, [1-cyclotetramethylene(phenyl)silyl-3-ethylcyclopentadienyl]titanium trichloride, [1-cyclotetramethylene(phenyl)silyl-2-n-propylcyclopentadienyl]titanium trichloride, [1-cyclotetramethylene(phenyl)silyl-3-n-propylcyclopentadienyl]titanium trichloride, [1-cyclotetramethylene(phenyl)silyl-2-isopropylcyclopentadienyl]titanium trichloride, [1-cyclotetramethylene(phenyl)silyl-3-isopropylcyclopentadienyl]titanium trichloride, [1-cyclotetramethylene(phenyl)silyl-2-n-butylcyclopentadienyl]titanium trichloride, [1-cyclotetramethylene(phenyl)silyl-3-n-butylcyclopentadienyl]titanium trichloride, [1-cyclotetramethylene(phenyl)silyl-2-sec-butylcyclopentadienyl]titanium trichloride, [1-cyclotetramethylene(phenyl)silyl-3-sec-butylcyclopentadienyl]titanium trichloride, [1-cyclotetramethylene(phenyl)silyl-2-tert-butylcyclopentadienyl]titanium trichloride, [1-cyclotetramethylene(phenyl)silyl-3-tert-butylcyclopentadienyl]titanium trichloride, [1-cyclotetramethylene(phenyl)silyl-2-phenylcyclopentadienyl]titanium trichloride, [1-cyclotetramethylene(phenyl)silyl-3-phenylcyclopentadienyl]titanium trichloride, [1-cyclotetramethylene(phenyl)silyl-2-benzylcyclopentadienyl]titanium trichloride, [1-cyclotetramethylene(phenyl)silyl-3-benzylcyclopentadienyl]titanium trichloride, [1-cyclotetramethylene(phenyl)silyl-indenyl]titanium trichloride, [1-cyclotetramethylene(phenyl)silyl-2-methylindenyl]titanium trichloride, [9-cyclotetramethylene(phenyl)silyl-fluorenyl]titanium trichloride, [1-cyclotetramethylene(phenyl)silyl-tetrahydroindenyl]titanium trichloride, [1-cyclotetramethylene(phenyl)silyl-2-methyltetrahydroindenyl]titanium trichloride, [9-cyclotetramethylene(phenyl)silyl-octahydrofluorenyl]titanium trichloride,
[1-ethylmethylphenylsilyl-2-methylcyclopentadienyl]titanium trichloride, [1-ethylmethylphenylsilyl-3-methylcyclopentadienyl]titanium trichloride, [1-ethylmethylphenylsilyl-2,3-dimethylcyclopentadienyl]titanium trichloride, [1-ethylmethylphenylsilyl-2,4-dimethylcyclopentadienyl]titanium trichloride, [1-ethylmethylphenylsilyl-2,5-dimethylcyclopentadienyl]titanium trichloride, [1-ethylmethylphenylsilyl-2,3,5-trimethylcyclopentadienyl]titanium trichloride, [1-ethylmethylphenylsilyl-2,3,4,5-tetramethylcyclopentadienyl]titanium trichloride, [1-ethylmethylphenylsilyl-2-ethylcyclopentadienyl]titanium trichloride, [1-ethylmethylphenylsilyl-3-ethylcyclopentadienyl]titanium trichloride, [1-ethylmethylphenylsilyl-2-n-propylcyclopentadienyl]titanium trichloride, [1-ethylmethylphenylsilyl-3-n-propylcyclopentadienyl]titanium trichloride, [1-ethylmethylphenylsilyl-2-isopropylcyclopentadienyl]titanium trichloride, [1-ethylmethylphenylsilyl-3-isopropylcyclopentadienyl]titanium trichloride, [1-ethylmethylphenylsilyl-2-n-butylcyclopentadienyl]titanium trichloride, [1-ethylmethylphenylsilyl-3-n-butylcyclopentadienyl]titanium trichloride, [1-ethylmethylphenylsilyl-2-sec-butylcyclopentadienyl]titanium trichloride, [1-ethylmethylphenylsilyl-3-sec-butylcyclopentadienyl]titanium trichloride, [1-ethylmethylphenylsilyl-2-tert-butylcyclopentadienyl]titanium trichloride, [1-ethylmethylphenylsilyl-3-tert-butylcyclopentadienyl]titanium trichloride, [1-ethylmethylphenylsilyl-2-phenylcyclopentadienyl]titanium trichloride, [1-ethylmethylphenylsilyl-3-phenylcyclopentadienyl]titanium trichloride, [1-ethylmethylphenylsilyl-2-benzylcyclopentadienyl]titanium trichloride, [1-ethylmethylphenylsilyl-3-benzylcyclopentadienyl]titanium trichloride, [1-ethylmethylphenylsilyl-indenyl]titanium trichloride, [1-ethylmethylphenylsilyl-2-methylindenyl]titanium trichloride, [9-ethylmethylphenylsilyl-fluorenyl]titanium trichloride, [1-ethylmethylphenylsilyl-tetrahydroindenyl]titanium trichloride, [1-ethylmethylphenylsilyl-2-methyltetrahydroindenyl]titanium trichloride, [9-ethylmethylphenylsilyl-octahydrofluorenyl]titanium trichloride,
[1-n-butylmethylphenylsilyl-2-methylcyclopentadienyl]titanium trichloride, [1-n-butylmethylphenylsilyl-3-methylcyclopentadienyl]titanium trichloride, [1-n-butylmethylphenylsilyl-2,3-dimethylcyclopentadienyl]titanium trichloride, [1-n-butylmethylphenylsilyl-2,4-dimethylcyclopentadienyl]titanium trichloride, [1-n-butylmethylphenylsilyl-2,5-dimethylcyclopentadienyl]titanium trichloride, [1-n-butylmethylphenylsilyl-2,3,5-trimethylcyclopentadienyl]titanium trichloride, [1-n-butylmethylphenylsilyl-2,3,4,5-tetramethylcyclopentadienyl]titanium trichloride, [1-n-butylmethylphenylsilyl-2-ethylcyclopentadienyl]titanium trichloride, [1-n-butylmethylphenylsilyl-3-ethylcyclopentadienyl]titanium trichloride, [1-n-butylmethylphenylsilyl-2-n-propylcyclopentadienyl]titanium trichloride, [1-n-butylmethylphenylsilyl-3-n-propylcyclopentadienyl]titanium trichloride, [1-n-butylmethylphenylsilyl-2-isopropylcyclopentadienyl]titanium trichloride, [1-n-butylmethylphenylsilyl-3-isopropylcyclopentadienyl]titanium trichloride, [1-n-butylmethylphenylsilyl-2-n-butylcyclopentadienyl]titanium trichloride, [1-n-butylmethylphenylsilyl-3-n-butylcyclopentadienyl]titanium trichloride, [1-n-butylmethylphenylsilyl-2-sec-butylcyclopentadienyl]titanium trichloride, [1-n-butylmethylphenylsilyl-3-sec-butylcyclopentadienyl]titanium trichloride, [1-n butylmethylphenylsilyl-2-tert-butylcyclopentadienyl]titanium trichloride, [1-n-butylmethylphenylsilyl-3-tert-butylcyclopentadienyl]titanium trichloride, [1-n-butylmethylphenylsilyl-2-phenylcyclopentadienyl]titanium trichloride, [1-n-butylmethylphenylsilyl-3-phenylcyclopentadienyl]titanium trichloride, [1-n-butylmethylphenylsilyl-2-benzylcyclopentadienyl]titanium trichloride, [1-n-butylmethylphenylsilyl-3-benzylcyclopentadienyl]titanium trichloride, [1-n-butylmethylphenylsilyl-indenyl]titanium trichloride, [1-n-butylmethylphenylsilyl-2-methylindenyl]titanium trichloride, [9-n-butylmethylphenylsilyl-fluorenyl]titanium trichloride, [1-n-butylmethylphenylsilyl-tetrahydroindenyl]titanium trichloride, [1-n-butylmethylphenylsilyl-2-methyltetrahydroindenyl]titanium trichloride, [9-n-butylmethylphenylsilyl-octahydrofluorenyl]titanium trichloride,
[1-methyldiphenylsilyl-2-methylcyclopentadienyl]titanium trichloride, [1-methyldiphenylsilyl-3-methylcyclopentadienyl]titanium trichloride, [1-methyldiphenylsilyl-2,3-dimethylcyclopentadienyl]titanium trichloride, [1-methyldiphenylsilyl-2,4-dimethylcyclopentadienyl]titanium trichloride, [1-methyldiphenylsilyl-2,5-dimethylcyclopentadienyl]titanium trichloride, [1-methyldiphenylsilyl-2,3,5-trimethylcyclopentadienyl]titanium trichloride, [1-methyldiphenylsilyl-2,3,4,5-tetramethylcyclopentadienyl]titanium trichloride,

[1-methyldiphenylsilyl-2-ethylcyclopentadienyl]titanium trichloride, [1-methyldiphenylsilyl-3-ethylcyclopentadienyl]titanium trichloride, [1-methyldiphenylsilyl-2-n-propylcyclopentadienyl]titanium trichloride, [1-methyldiphenylsilyl-3-n-propylcyclopentadienyl]titanium trichloride, [1-methyldiphenylsilyl-2-isopropylcyclopentadienyl]titanium trichloride, [1-methyldiphenylsilyl-2-n-butylcyclopentadienyl]titanium trichloride, [1-methyldiphenylsilyl-3-n-butylcyclopentadienyl]titanium trichloride, [1-methyldiphenylsilyl-2-sec-butylcyclopentadienyl]titanium trichloride, [1-methyldiphenylsilyl-3-sec-butylcyclopentadienyl]titanium trichloride, [1-methyldiphenylsilyl-2-tert-butylcyclopentadienyl]titanium trichloride, [1-methyldiphenylsilyl-3-tert-butylcyclopentadienyl]titanium trichloride, [1-methyldiphenylsilyl-2-phenylcyclopentadienyl]titanium trichloride, [1-methyldiphenylsilyl-3-phenylcyclopentadienyl]titanium trichloride, [1-methyldiphenylsilyl-2-benzylcyclopentadienyl]titanium trichloride, [1-methyldiphenylsilyl-3-benzylcyclopentadienyl]titanium trichloride, [1-methyldiphenylsilyl-indenyl]titanium trichloride, [1-methyldiphenylsilyl-2-methylindenyl]titanium trichloride, [9-methyldiphenylsilyl-fluorenyl]titanium trichloride, [1-methyldiphenylsilyl-tetrahydroindenyl]titanium trichloride, [1-methyldiphenylsilyl-2-methyltetrahydroindenyl]titanium trichloride, [9-methyldiphenylsilyl-octahydrofluorenyl]titanium trichloride,
[1-cyclohexylmethylphenylsilyl-2-methylcyclopentadienyl]titanium trichloride, [1-cyclohexylmethylphenylsilyl-3-methylcyclopentadienyl]titanium trichloride, [1-cyclohexylmethylphenylsilyl-2,3-dimethylcyclopentadienyl]titanium trichloride, [1-cyclohexylmethylphenylsilyl-2,4-dimethylcyclopentadienyl]titanium trichloride, [1-cyclohexylmethylphenylsilyl-2,5-dimethylcyclopentadienyl]titanium trichloride, [1-cyclohexylmethylphenylsilyl-2,3,5-trimethylcyclopentadienyl]titanium trichloride, [1-cyclohexylmethylphenylsilyl-2,3,4,5-tetramethylcyclopentadienyl]titanium trichloride, [1-cyclohexylmethylphenylsilyl-2-ethylcyclopentadienyl]titanium trichloride, [1-cyclohexylmethylphenylsilyl-3-ethylcyclopentadienyl]titanium trichloride, [1-cyclohexylmethylphenylsilyl-2-n-propylcyclopentadienyl]titanium trichloride, [1-cyclohexylmethylphenylsilyl-3-n-propylcyclopentadienyl]titanium trichloride, [1-cyclohexylmethylphenylsilyl-2-isopropylcyclopentadienyl]titanium trichloride, cyclohexylmethylphenylsilyl-3-isopropylcyclopentadienyl]titanium trichloride, [1-cyclohexylmethylphenylsilyl-2-n-butylcyclopentadienyl]titanium trichloride, [1-cyclohexylmethylphenylsilyl-3-n-butylcyclopentadienyl]titanium trichloride, [1-cyclohexylmethylphenylsilyl-2-sec-butylcyclopentadienyl]titanium trichloride, [1-cyclohexylmethylphenylsilyl-3-sec-butylcyclopentadienyl]titanium trichloride, [1-cyclohexylmethylphenylsilyl-2-tert-butylcyclopentadienyl]titanium trichloride, cyclohexylmethylphenylsilyl-3-tert-butylcyclopentadienyl]titanium trichloride, [1-cyclohexylmethylphenylsilyl-2-phenylcyclopentadienyl]titanium trichloride, [1-cyclohexylmethylphenylsilyl-3-phenylcyclopentadienyl]titanium trichloride, [1-cyclohexylmethylphenylsilyl-2-benzylcyclopentadienyl]titanium trichloride, cyclohexylmethylphenylsilyl-3-benzylcyclopentadienyl]titanium trichloride, [1-cyclohexylmethylphenylsilyl-indenyl]titanium trichloride, [1-cyclohexylmethylphenylsilyl-2-methylindenyl]titanium trichloride, [9-cyclohexylmethylphenylsilyl-fluorenyl]titanium trichloride, [1-cyclohexylmethylphenylsilyl-tetrahydroindenyl]titanium trichloride, [1-cyclohexylmethylphenylsilyl-2-methyltetrahydroindenyl]titanium trichloride, [9-cyclohexylmethylphenylsilyl-octahydrofluorenyl]titanium trichloride,
[1-methyl(n-octadecyl)phenylsilyl-2-methylcyclopentadienyl]titanium trichloride, [1-methyl(n-octadecyl)phenylsilyl-3-methylcyclopentadienyl]titanium trichloride, [1-methyl(n-octadecyl)phenylsilyl-2,3-dimethylcyclopentadienyl]titanium trichloride, [1-methyl(n-octadecyl)phenylsilyl-2,4-dimethylcyclopentadienyl]titanium trichloride, [1-methyl(n-octadecyl)phenylsilyl-2,5-dimethylcyclopentadienyl]titanium trichloride, [1-methyl(n-octadecyl)phenylsilyl-2,3,5-trimethylcyclopentadienyl]titanium trichloride, [1-methyl(n-octadecyl)phenylsilyl-2,3,4,5-tetramethylcyclopentadienyl]titanium trichloride, [1-methyl(n-octadecyl)phenylsilyl-2-ethylcyclopentadienyl]titanium trichloride, [1-methyl(n-octadecyl)phenylsilyl-3-ethylcyclopentadienyl]titanium trichloride, [1-methyl(n-octadecyl)phenylsilyl-2-n-propylcyclopentadienyl]titanium trichloride, [1-methyl(n-octadecyl)phenylsilyl-3-n-propylcyclopentadienyl]titanium trichloride, [1-methyl(n-octadecyl)phenylsilyl-2-isopropylcyclopentadienyl]titanium trichloride, [1-methyl(n-octadecyl)phenylsilyl-3-isopropylcyclopentadienyl]titanium trichloride, [1-methyl(n-octadecyl)phenylsilyl-2-n-butylcyclopentadienyl]titanium trichloride, [1-methyl(n-octadecyl)phenylsilyl-3-n-butylcyclopentadienyl]titanium trichloride, [1-methyl(n-octadecyl)phenylsilyl-2-sec-butylcyclopentadienyl]titanium trichloride, [1-methyl(n-octadecyl)phenylsilyl-3-sec-butylcyclopentadienyl]titanium trichloride, [1-methyl(n-octadecyl)phenylsilyl-2-tert-butylcyclopentadienyl]titanium trichloride, [1-methyl(n-octadecyl)phenylsilyl-3-tert-butylcyclopentadienyl]titanium trichloride, [1-methyl(n-octadecyl)phenylsilyl-2-phenylcyclopentadienyl]titanium trichloride, [1-methyl(n-octadecyl)phenylsilyl-3-phenylcyclopentadienyl]titanium trichloride, [1-methyl(n-octadecyl)phenylsilyl-2-benzylcyclopentadienyl]titanium trichloride, [1-methyl(n-octadecyl)phenylsilyl-3-benzylcyclopentadienyl]titanium trichloride, [1-methyl(n-octadecyl)phenylsilyl-indenyl]titanium trichloride, [1-methyl(n-octadecyl)phenylsilyl-2-methylindenyl]titanium trichloride, [9-methyl(n-octadecyl)phenylsilyl-fluorenyl]titanium trichloride, [1-methyl(n-octadecyl)phenylsilyl-tetrahydroindenyl]titanium trichloride, [1-methyl(n-octadecyl)phenylsilyl-2-methyltetrahydroindenyl]titanium trichloride, [9-methyl(n-octadecyl)phenylsilyl-octahydrofluorenyl]titanium trichloride,
[1-triphenylsilyl-2-methylcyclopentadienyl]titanium trichloride, [1-triphenylsilyl-3-methylcyclopentadienyl]titanium trichloride, [1-triphenylsilyl-2,3-dimethylcyclopentadienyl]titanium trichloride, [1-triphenylsilyl-2,4-dimethylcyclopentadienyl]titanium trichloride, [1-triphenylsilyl-2,5-dimethylcyclopentadienyl]titanium trichloride, [1-triphenylsilyl-2,3,5-trimethylcyclopentadienyl]titanium trichloride, [1-triphenylsilyl-2,3,4,5-tetramethylcyclopentadienyl]titanium trichloride, [1-triphenylsilyl-2-ethylcyclopentadienyl]titanium trichloride, [1-triphenylsilyl-3-ethylcyclopentadienyl]titanium trichloride, [1-triphenylsilyl-2-n-propylcyclopentadienyl]titanium trichloride, [1-triphenylsilyl-3-n-propylcyclopentadienyl]titanium trichloride, [1-triphenylsilyl-2-isopropylcyclopentadienyl]titanium trichloride, [1-triphenylsilyl-3-isopropylcyclopentadienyl]titanium trichloride, [1-triphenylsilyl-2-n-butylcyclopentadienyl]titanium trichloride, [1-triphenylsilyl-3-n-butylcyclopentadienyl]titanium trichloride, [1-triphenylsilyl-2-sec-butylcyclopentadienyl]titanium trichloride, [1-triphenylsilyl-3-sec-butylcyclopentadienyl]titanium trichloride, [1-triphenylsilyl-2-tert-butylcyclopentadienyl]titanium trichloride, [1-triphenylsilyl-3-tert-butylcyclopentadienyl]titanium trichloride, [1-triphenylsilyl-2-phenylcyclopentadienyl]titanium trichloride, [1-triphenylsilyl-3-phenylcyclopentadienyl]titanium trichloride, [1-triphenylsilyl-2-benzylcyclopentadienyl]titanium trichloride, [1-triphenylsilyl-3-benzylcyclopentadienyl]titanium trichloride, [1-triphenylsilyl-indenyl]titanium trichloride, [1-triphenylsilyl-2-methylindenyl]titanium trichloride, [9-triphenylsilyl-fluorenyl]titanium trichloride, [1-triphenylsilyl-tetrahydroindenyl]titanium trichloride, [1-triphenylsilyl-2-methyltetrahydroindenyl]titanium trichloride, [9-triphenylsilyl-octahydrofluorenyl]titanium trichloride, [1-tri(4-n-butylphenyl)silyl-2-methylcyclopentadienyl]titanium trichloride, [1-tri(4-n-butylphenyl)silyl-3-methylcyclopentadienyl]titanium trichloride, [1-tri(4-n-butylphenyl)silyl-2,3-dimethylcyclopentadienyl]titanium trichloride, [1-tri(4-n-butylphenyl)silyl-2,4-dimethylcyclopentadienyl]titanium trichloride, [1-tri(4-n-butylphenyl)silyl-2,5-dimethylcyclopentadienyl]titanium trichloride, [1-tri(4-n-butylphenyl)silyl-2,3,5-trimethylcyclopentadienyl]titanium trichloride, [1-tri(4-n-butylphenyl)silyl-2,3,4,5-tetramethylcyclopentadienyl]titanium trichloride, [1-tri(4-n-butylphenyl)silyl-2-ethylcyclopentadienyl]titanium trichloride, [1-tri(4-n-butylphenyl)silyl-3-ethylcyclopentadienyl]titanium trichloride, [1-tri(4-n-butylphenyl)silyl-2-n-propylcyclopentadienyl]titanium trichloride, [1-tri(4-n-butylphenyl)silyl-3-n-propylcyclopentadienyl]titanium trichloride, [1-tri(4-n-butylphenyl)silyl-2-isopropylcyclopentadienyl]titanium trichloride, [1-tri(4-n-butylphenyl)silyl-3-isopropylcyclopentadienyl]titanium trichloride, [1-tri(4-n-butylphenyl)silyl-2-n-butylcyclopentadienyl]titanium trichloride, [1-tri(4-n-butylphenyl)silyl-3-n-butylcyclopentadienyl]titanium trichloride, [1-tri(4-n-butylphenyl)silyl-2-sec-butylcyclopentadienyl]titanium trichloride, [1-tri(4-n-butylphenyl)silyl-3-sec-butylcyclopentadienyl]titanium tri chloride, [1-tri(4-n-butylphenyl)silyl-2-tert-butylcyclopentadienyl]titanium trichloride, [1-tri(4-n-butylphenyl)silyl-3-tert-butylcyclopentadienyl]titanium trichloride, [1-tri(4-n-butylphenyl)silyl-2-phenylcyclopentadienyl]titanium trichloride, [1-tri(4-n-butylphenyl)silyl-3-phenylcyclopentadienyl]titanium trichloride, [1-tri(4-n-butylphenyl)silyl-2-benzylcyclopentadienyl]titanium trichloride, [1-tri(4-n-butylphenyl)silyl-3-benzylcyclopentadienyl]titanium trichloride, [1-tri(4-n-butylphenyl)silyl-indenyl]titanium trichloride, [1-tri(4-n-butylphenyl)silyl-2-methylindenyl]titanium trichloride, [9-tri(4-n-butylphenyl)silyl-fluorenyl]titanium trichloride, [1-tri(4-n-butylphenyl)silyl-tetrahydroindenyl]titanium trichloride, [1-tri(4-n-butylphenyl)silyl-2-methyltetrahydroindenyl]titanium trichloride, [9-tri(4-n-butylphenyl)silyl-octahydrofluorenyl]titanium trichloride, [1-dimethyl(3,5-dimethylphenyl)silyl-2-methylcyclopentadienyl]titanium trichloride, [1-dimethyl(3,5-dimethylphenyl)silyl-3-methylcyclopentadienyl]titanium trichloride, [1-dimethyl(3,5-dimethylphenyl)silyl-2,3-dimethylcyclopentadienyl]titanium trichloride, [1-dimethyl(3,5-dimethylphenyl)silyl-2,4-dimethylcyclopentadienyl]titanium trichloride, [1-dimethyl(3,5-dimethylphenyl)silyl-2,5-dimethylcyclopentadienyl]titanium trichloride, [1-dimethyl(3,5-dimethylphenyl)silyl-2,3,5-trimethylcyclopentadienyl]titanium trichloride, [1-dimethyl(3,5-dimethylphenyl)silyl-2,3,4,5-tetramethylcyclopentadienyl]titanium trichloride, [1-dimethyl(3,5-dimethylphenyl)silyl-2-ethylcyclopentadienyl]titanium trichloride, [1-dimethyl(3,5-dimethylphenyl)silyl-3-ethylcyclopentadienyl]titanium trichloride, [1-dimethyl(3,5-dimethylphenyl)silyl-2-n-propylcyclopentadienyl]titanium trichloride, [1-dimethyl(3,5-dimethylphenyl)silyl-3-n-propylcyclopentadienyl]titanium trichloride, [1-dimethyl(3,5-dimethylphenyl)silyl-2-isopropylcyclopentadienyl]titanium trichloride, [1-dimethyl(3,5-dimethylphenyl)silyl-3-isopropylcyclopentadienyl]titanium trichloride, [1-dimethyl(3,5-dimethylphenyl)silyl-2-n-butylcyclopentadienyl]titanium trichloride, [1-dimethyl(3,5-dimethylphenyl)silyl-3-n-butylcyclopentadienyl]titanium trichloride, [1-dimethyl(3,5-dimethylphenyl)silyl-2-sec-butylcyclopentadienyl]titanium trichloride, [1-dimethyl(3,5-dimethylphenyl)silyl-3-sec-butylcyclopentadienyl]titanium trichloride, [1-dimethyl(3,5-dimethylphenyl)silyl-2-tert-butylcyclopentadienyl]titanium trichloride, [1-dimethyl(3,5-dimethylphenyl)silyl-3-tert-butylcyclopentadienyl]titanium trichloride, [1-dimethyl(3,5-dimethylphenyl)silyl-2-phenylcyclopentadienyl]titanium trichloride, [1-dimethyl(3,5-dimethylphenyl)silyl-3-phenylcyclopentadienyl]titanium trichloride, [1-dimethyl(3,5-dimethylphenyl)silyl-2-benzylcyclopentadienyl]titanium trichloride, [1-dimethyl(3,5-dimethylphenyl)silyl-3-benzylcyclopentadienyl]titanium trichloride, [1-dimethyl(3,5-dimethylphenyl)silyl-indenyl]titanium trichloride, [1-dimethyl(3,5-dimethylphenyl)silyl-2-methylindenyl]titanium trichloride, [9-dimethyl(3,5-dimethylphenyl)silyl-fluorenyl]titanium trichloride, [1-dimethyl(3,5-dimethylphenyl)silyl-tetrahydroindenyl]titanium trichloride, [1-dimethyl(3,5-dimethylphenyl)silyl-2-methyltetrahydroindenyl]titanium trichloride, [9-dimethyl(3,5-dimethylphenyl)silyl-octahydrofluorenyl]titanium trichloride, [1-n-butylmethyl(3,5-dimethylphenyl)silyl-2-methylcyclopentadienyl]titanium trichloride, [1-n-butylmethyl(3,5-dimethylphenyl)silyl-3-methylcyclopentadienyl]titanium trichloride, [1-n-butylmethyl(3,5-dimethylphenyl)silyl-2,3-dimethylcyclopentadienyl]titanium trichloride, [1-n-butylmethyl(3,5-dimethylphenyl)silyl-2,4-dimethylcyclopentadienyl]titanium trichloride, [1-n-butylmethyl(3,5-dimethylphenyl)silyl-2,5-dimethylcyclopentadienyl]titanium trichloride, [1-n-butylmethyl(3,5-dimethylphenyl)silyl-2,3,5-trimethylcyclopentadienyl]titanium trichloride, [1-n-butylmethyl(3,5-dimethylphenyl)silyl-2,3,4,5-tetramethylcyclopentadienyl]titanium trichloride, [1-n-butylmethyl(3,5-dimethylphenyl)silyl-2-ethylcyclopentadienyl]titanium trichloride, [1-n-butylmethyl(3,5-dimethylphenyl)silyl-3-ethylcyclopentadienyl]titanium trichloride, [1-n-butylmethyl(3,5-dimethylphenyl)silyl-2-n-propylcyclopentadienyl]titanium trichloride, [1-n-butylmethyl(3,5-dimethylphenyl)silyl-3-n-propylcyclopentadienyl]titanium trichloride, [1-n-butylmethyl(3,5-dimethylphenyl)silyl-2-isopropylcyclopentadienyl]titanium trichloride, [1-n-butylmethyl(3,5-dimethylphenyl)silyl-3-isopropylcyclopentadienyl]titanium trichloride, [1-n-butylmethyl(3,5-dimethylphenyl)silyl-2-n-butylcyclopentadienyl]titanium trichloride, [1-n-butylmethyl(3,5-dimethylphenyl)silyl-3-n-butylcyclopentadienyl]titanium trichloride, [1-n-butylmethyl(3,5-dimethylphenyl)silyl-2-sec-butylcyclopentadienyl]titanium trichloride, [1-n-butylmethyl(3,5-dimethylphenyl)silyl-3-sec-butylcyclopentadienyl]titanium trichloride, [1-n-butylmethyl(3,5-dimethylphenyl)silyl-2-tert-butylcyclopentadienyl]titanium trichloride, [1-n-butylmethyl(3,5-dimethylphenyl)silyl-3-tert-butylcyclopentadienyl]titanium trichloride, [1-n-butylmethyl(3,5-dimethylphenyl)silyl-2-phenylcyclopentadienyl]titanium trichloride, [1-n-butylmethyl(3,5-dimethylphenyl)silyl-3-phenylcyclopentadienyl]titanium trichloride, [1-n-butylmethyl(3,5-dimethylphenyl)silyl-2-benzylcyclopentadienyl]titanium trichloride, [1-n-butylmethyl(3,5-dimethylphenyl)silyl-3-benzylcyclopentadienyl]titanium trichloride, [1-n-butylmethyl(3,5-dimethylphenyl)silyl-indenyl]titanium trichloride, [1-n-butylmethyl(3,5-dimethylphenyl)silyl-2-methylindenyl]titanium trichloride, [9-n-butylmethyl(3,5-dimethylphenyl)silyl-fluorenyl]titanium trichloride, [1-n-butylmethyl(3,5-dimethylphenyl)silyl-tetrahydroindenyl]titanium trichloride, [1-n-butylmethyl(3,5-dimethylphenyl)silyl-2-methyltetrahydroindenyl]titanium trichloride, [9-n-butylmethyl(3,5-dimethylphenyl)silyl-octahydrofluorenyl]titanium trichloride, [1-tris(3,5-dimethylphenyl)silyl-2-methylcyclopentadienyl]titanium trichloride, [1-tris(3,5-dimethylphenyl)silyl-3-methylcyclopentadienyl]titanium trichloride, [1-tris(3,5-dimethylphenyl)silyl-2,3-dimethylcyclopentadienyl]titanium trichloride, [1-tris(3,5-dimethylphenyl)silyl-2,4-dimethylcyclopentadienyl]titanium trichloride, [1-tris(3,5-dimethylphenyl)silyl-2,5-dimethylcyclopentadienyl]titanium trichloride, [1-tris(3,5-dimethylphenyl)silyl-2,3,5-trimethylcyclopentadienyl]titanium trichloride, [1-tris(3,5-dimethylphenyl)silyl-2,3,4,5-tetramethylcyclopentadienyl]titanium trichloride,

[1-tris(3,5-dimethylphenyl)silyl-2-ethylcyclopentadienyl]titanium trichloride, [1-tris(3,5-dimethylphenyl)silyl-3-ethylcyclopentadienyl]titanium trichloride, [1-tris(3,5-dimethylphenyl)silyl-2-n-propylcyclopentadienyl]titanium trichloride, [1-tris(3,5-dimethylphenyl)silyl-3-n-propylcyclopentadienyl]titanium trichloride, [1-tris(3,5-dimethylphenyl)silyl-2-isopropylcyclopentadienyl]titanium trichloride, [1-tris(3,5-dimethylphenyl)silyl-3-isopropylcyclopentadienyl]titanium trichloride, [1-tris(3,5-dimethylphenyl)silyl-2-n-butylcyclopentadienyl]titanium trichloride, [1-tris(3,5-dimethylphenyl)silyl-3-n-butylcyclopentadienyl]titanium trichloride, [1-tris(3,5-dimethylphenyl)silyl-2-sec-butylcyclopentadienyl]titanium trichloride, [1-tris(3,5-dimethylphenyl)silyl-3-sec-butylcyclopentadienyl]titanium trichloride, [1-tris(3,5-dimethylphenyl)silyl-2-tert-butylcyclopentadienyl]titanium trichloride, [1-tris(3,5-dimethylphenyl)silyl-3-tert-butylcyclopentadienyl]titanium trichloride, [1-tris(3,5-dimethylphenyl)silyl-2-phenylcyclopentadienyl]titanium trichloride, [1-tris(3,5-dimethylphenyl)silyl-3-phenylcyclopentadienyl]titanium trichloride, [1-tris(3,5-dimethylphenyl)silyl-2-benzylcyclopentadienyl]titanium trichloride, [1-tris(3,5-dimethylphenyl)silyl-3-benzylcyclopentadienyl]titanium trichloride, [1-tris(3,5-dimethylphenyl)silyl-indenyl]titanium trichloride, [1-tris(3,5-dimethylphenyl)silyl-2-methylindenyl]titanium trichloride, [9-tris(3,5-dimethylphenyl)silylsilyl)-fluorenyl]titanium trichloride, [1-tris(3,5-dimethylphenyl)silyl-tetrahydroindenyl]titanium trichloride, [1-tris(3,5-dimethylphenyl)silyl-2-methyltetrahydroindenyl]titanium trichloride, [9-tris(3,5-dimethylphenyl)silyl-octahydrofluorenyl]titanium trichloride, [1-n-butylmethyl(2,4,6-trimethylphenyl)silyl-2-methylcyclopentadienyl]titanium trichloride, [1-n-butylmethyl(2,4,6-trimethylphenyl)silyl-3-methylcyclopentadienyl]titanium trichloride, [1-n-butylmethyl(2,4,6-trimethylphenyl)silyl-2,3-dimethylcyclopentadienyl]titanium trichloride, [1-n-butylmethyl(2,4,6-trimethylphenyl)silyl]-2,4-dimethylcyclopentadienyl]titanium trichloride, [1-n-butylmethyl(2,4,6-trimethylphenyl)silyl-2,5-dimethylcyclopentadienyl] titanium trichloride, [1-n-butylmethyl(2,4,6-trimethylphenyl)silyl-2,3,5-trimethylcyclopentadienyl] titanium trichloride, [1-n-butylmethyl(2,4,6-trimethylphenyl)silyl-2,3,4,5-tetramethylcyclopentadienyl] titanium trichloride, [1-n-butylmethyl(2,4,6-trimethylphenyl)silyl-2-ethylcyclopentadienyl]titanium trichloride, [1-n-butylmethyl(2,4,6-trimethylphenyl)silyl-3-ethylcyclopentadienyl]titanium trichloride, [1-n-butylmethyl(2,4,6-trimethylphenyl)silyl-2-n-propylcyclopentadienyl]titanium trichloride, [1-n-butylmethyl(2,4,6-trimethylphenyl)silyl-3-n-propylcyclopentadienyl]titanium trichloride, [1-n-butylmethyl(2,4,6-trimethylphenyl)silyl-2-isopropylcyclopentadienyl]titanium trichloride, [1-n-butylmethyl(2,4,6-trimethylphenyl)silyl-3-isopropylcyclopentadienyl]titanium trichloride, [1-n-butylmethyl(2,4,6-trimethylphenyl)silyl-2-n-butylcyclopentadienyl]titanium trichloride, [1-n-butylmethyl(2,4,6-trimethylphenyl)silyl-3-n-butylcyclopentadienyl]titanium trichloride, [1-n-butylmethyl(2,4,6-trimethylphenyl)silyl-2-sec-butylcyclopentadienyl]titanium trichloride, [1-n-butylmethyl(2,4,6-trimethylphenyl)silyl-3-sec-butylcyclopentadienyl]titanium trichloride, [1-n-butylmethyl(2,4,6-trimethylphenyl)silyl-2-tert-butylcyclopentadienyl]titanium trichloride, [1-n-butylmethyl(2,4,6-trimethylphenyl)silyl-3-tert-butylcyclopentadienyl]titanium trichloride, [1-n-butylmethyl(2,4,6-trimethylphenyl)silyl-2-phenylcyclopentadienyl]titanium trichloride, [1-n-butylmethyl(2,4,6-trimethylphenyl)silyl-3-phenylcyclopentadienyl]titanium trichloride, [1-n-butylmethyl(2,4,6-trimethylphenyl)silyl-2-benzylcyclopentadienyl]titanium trichloride, [1-n-butylmethyl(2,4,6-trimethylphenyl)silyl-3-benzylcyclopentadienyl]titanium trichloride, [1-n-butylmethyl(2,4,6-trimethylphenyl)silyl-indenyl]titanium trichloride, [1-n-butylmethyl(2,4,6-trimethylphenyl)silyl-2-methylindenyl]titanium trichloride, [9-n-butylmethyl(2,4,6-trimethylphenyl)silyl-fluorenyl]titanium trichloride, [1-n-butylmethyl(2,4,6-trimethylphenyl)silyl-tetrahydroindenyl]titanium trichloride, [1-n-butylmethyl(2,4,6-trimethylphenyl)silyl-2-methyltetrahydroindenyl]titanium trichloride, [9-n-butylmethyl(2,4,6-trimethylphenyl)silyl-octahydrofluorenyl]titanium trichloride,
[1-n-butylmethyl(pentamethylphenyl)silyl-2-methylcyclopentadienyl]titanium trichloride, [1-n-butylmethyl(pentamethylphenyl)silyl-3-methylcyclopentadienyl]titanium trichloride, [1-n-butylmethyl(pentamethylphenyl)silyl-2,3-dimethylcyclopentadienyl]titanium trichloride, [1-n-butylmethyl(pentamethylphenyl)silyl-2,4-dimethylcyclopentadienyl]titanium trichloride, [1-n-butylmethyl(pentamethylphenyl)silyl-2,5-dimethylcyclopentadienyl] titanium trichloride, [1-n-butylmethyl(pentamethylphenyl)silyl-2,3,5-trimethylcyclopentadienyl]titanium trichloride, [1-n-butylmethyl(pentamethylphenyl)silyl-2,3,4,5-tetramethylcyclopentadienyl]titanium trichloride, [1-n-butylmethyl(pentamethylphenyl)silyl-2-ethylcyclopentadienyl]titanium trichloride, [1-n-butylmethyl(pentamethylphenyl)silyl-3-ethylcyclopentadienyl]titanium trichloride, [1-n-butylmethyl(pentamethylphenyl)silyl-2-n-propylcyclopentadienyl]titanium trichloride, [1-n-butylmethyl(pentamethylphenyl)silyl-3-n-propylcyclopentadienyl]titanium trichloride, [1-n-butylmethyl(pentamethylphenyl)silyl-2-isopropylcyclopentadienyl]titanium trichloride, [1-n-butylmethyl(pentamethylphenyl)silyl-3-isopropylcyclopentadienyl]titanium trichloride, [1-n-butylmethyl(pentamethylphenyl)silyl-2-n-butylcyclopentadienyl]titanium trichloride, [1-n-butylmethyl(pentamethylphenyl)silyl-3-n-butylcyclopentadienyl]titanium trichloride, [1-n-butylmethyl(pentamethylphenyl)silyl-2-sec-butylcyclopentadienyl]titanium trichloride, [1-n-butylmethyl(pentamethylphenyl)silyl-3-sec-butylcyclopentadienyl]titanium trichloride, [1-n-butylmethyl(pentamethylphenyl)silyl-2-tert-butylcyclopentadienyl]titanium trichloride, [1-n-butylmethyl(pentamethylphenyl)silyl-3-tert-butylcyclopentadienyl]titanium trichloride, [1-n-butylmethyl(pentamethylphenyl)silyl-2-phenylcyclopentadienyl]titanium trichloride, [1-n-butylmethyl(pentamethylphenyl)silyl-3-phenylcyclopentadienyl]titanium trichloride, [1-n-butylmethyl(pentamethylphenyl)silyl-2-benzylcyclopentadienyl]titanium trichloride, [1-n-butylmethyl(pentamethylphenyl)silyl-3-benzylcyclopentadienyl]titanium trichloride, [1-n-butylmethyl(pentamethylphenyl)silyl-indenyl]titanium trichloride, [1-n-butylmethyl(pentamethylphenyl)silyl-2-methylindenyl]titanium trichloride, [9-n-butylmethyl(pentamethylphenyl)silyl-fluorenyl]titanium trichloride, [1-n-butylmethyl(pentamethylphenyl)silyl-tetrahydroindenyl] titanium trichloride, [1-n-butylmethyl(pentamethylphenyl) silyl-2-methyltetrahydroindenyl]titanium trichloride and [9-n-butylmethyl(pentamethylphenyl)silyl-octahydrofluorenyl]titanium trichloride.

Moreover, examples of the transition metal complex (1) also include: transition metal chloride complexes such as zirconium chloride complexes obtained by substituting "zirconium" for "titanium" in the complexes exemplified above, and hafnium chloride complexes obtained by substituting "hafnium" therefor; titanium halide complexes such as titanium fluoride complexes obtained by substituting "fluoride" for "chloride in the complexes, titanium bromide complexes obtained by substituting "bromide" therefor and titanium iodide complexes obtained by substituting "iodide" therefor; titanium hydride complexes obtained by substituting "hydride" therefor; alkylated titanium complexes such as a methylated titanium complex obtained by substituting "methyl" therefor; arylated titanium complexes such as a phenylated titanium complex obtained by substituting "phenyl" therefor; aralkylated titanium complexes such as a benzylated titanium complex obtained by substituting "benzyl" therefor; titanium alkoxide complexes such as a titanium methoxide complex obtained by substituting "methoxide" therefor, a titanium n-butoxide complex obtained by substituting "n-butoxide" therefor and a titanium isopropoxide complex obtained by substituting "isopropoxide" therefor; titanium aryloxide complexes such as a titanium phenoxide complex obtained by substituting "phenoxide" therefor; titanium aralkyloxide complexes such as a titanium benzyloxide complex obtained by substituting "benzyloxide" therefor; and titanium amide complexes such as a titanium dimethylamide complex obtained by substituting "dimethylamide" therefor and a titanium diethylamide complex obtained by substituting "diethylamide" therefor.

Preferable examples of the transition metal complex of the formula (1) include [1-dimethylphenylsilyl-2,3,4,5-tetramethylcyclopentadienyl]titanium trichloride, [1-diethylphenylsilyl-2,3,4,5-tetramethylcyclopentadienyl]titanium trichloride, [1-cyclotetramethylene(phenyl)silyl-2,3,4,5-tetramethylcyclopentadienyl]titanium trichloride, [1-ethylmethylphenylsilyl-2,3,4,5-tetramethylcyclopentadienyl]titanium trichloride, [1-n-butylmethylphenylsilyl-2,3,4,5-tetramethylcyclopentadienyl]titanium trichloride, [1-methyldiphenylsilyl-2,3,4,5-tetramethylcyclopentadienyl]titanium trichloride, [1-cyclohexylmethylphenylsilyl-2,3,4,5-tetramethylcyclopentadienyl]titanium trichloride, [1-methyl(n-octadecyl)phenylsilyl-2,3,4,5-tetramethylcyclopentadienyl]titanium trichloride, [1-triphenylsilyl-2,3,4,5-tetramethylcyclopentadienyl]titanium trichloride, [1-tri(4-n-butylphenyl)silyl-2,3,4,5-tetramethylcyclopentadienyl] titanium trichloride, [1-dimethyl(3,5-dimethylphenyl)silyl-2,3,4,5-tetramethylcyclopentadienyl]titanium trichloride, [1-n-butylmethyl(3,5-dimethylphenyl)silyl-2,3,4,5-tetramethylcyclopentadienyl]titanium trichloride, [1-tris(3,5-dimethylphenyl)silyl-2,3,4,5-tetramethylcyclopentadienyl]titanium trichloride and [1-methyl di(4-methylphenyl)silyl-2,3,4,5-tetramethylcyclopentadienyl]titanium trichloride. Further preferable examples thereof include [1-n-butylmethylphenylsilyl-2,3,4,5-tetramethylcyclopentadienyl]titanium trichloride, [1-methyldiphenylsilyl-2,3,4,5-tetramethylcyclopentadienyl]titanium trichloride, [1-triphenylsilyl-2,3,4,5-tetramethylcyclopentadienyl]titanium trichloride, [1-tris(3,5-dimethylphenyl)silyl-2,3,4,5-tetramethylcyclopentadienyl]titanium trichloride and [1-dimethyl(4-methoxyphenyl)silyl-2,3,4,5-tetramethylcyclopentadienyl]titanium trichloride.

<Transition Metal Complex (5)>

Examples of the transition metal complex (5) include a transition metal complex represented by the following general formula (5).

[Formula 5]

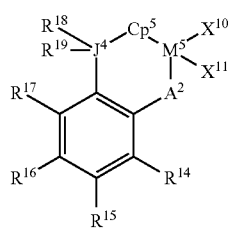

(5)

[In the formula, $M^5$ represents a transition metal atom of Group 4 of the Periodic Table of the Elements;
$A^2$ represents an atom of Group 16 of the Periodic Table of the Elements;
$J^4$ represents an atom of Group 14 of the Periodic Table of the Elements;
$Cp^5$ represents a group having a cyclopentadiene type anion skeleton;
$X^{10}, X^{11}, R^{14}, R^{15}, R^{16}$ and $R^{17}$ each independently represent, hydrogen atom, a halogen atom,
an alkyl group having 1 to 20 carbon atoms which may have a halogen atom as a substituent,
an alkoxy group having 1 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent,
a substituted silyl group represented by —Si($R^{12}$)$_3$, wherein the three $R^{12}$ groups each independently represent hydrogen atom, a hydrocarbyl group or a hydrocarbyl halide group, and the total number of the carbon atoms in the three $R^{12}$ groups is 1 to 20,
or a disubstituted amino group represented by —N($R^{13}$)$_2$, wherein the two $R^{13}$ groups each independently represent a hydrocarbyl group or a hydrocarbyl halide group, and the total number of the carbon atoms in the two $R^{13}$ groups is 2 to 20;
$R^{18}$ and $R^{19}$ each independently represent,
hydrogen atom,
an alkyl group having 1 to 20 carbon atoms which may have a halogen atom as a substituent,
an alkoxy group having 1 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent,
a substituted silyl group represented by —Si($R^{12}$)$_3$, wherein the three $R^{12}$ groups each independently represent hydrogen atom, a hydrocarbyl group or a hydrocarbyl halide group, and the total number of the carbon atoms in the three $R^{12}$ groups is 1 to 20,
or a disubstituted amino group represented by —N($R^{13}$)$_2$, wherein the two $R^{13}$ groups each independently represent a hydrocarbyl group or a hydrocarbyl halide group, and the total number of the carbon atoms in the two $R^{13}$ groups is 2 to 20;
of $R^{14}, R^{15}, R^{16}$ and $R^{17}$, two groups bonded to two adjacent carbon atoms may be bonded to form a ring together with the two carbon atoms to which the two groups are bonded;
$X^{10}$ and $X^{11}$ may be bonded to form a ring together with $M^5$; and
$R^{18}$ and $R^{19}$ may be bonded to form a ring together with $J^4$.]

A complex represented by the general formula (5) will be more specifically described. Examples of the transition metal atom represented by $M^5$ and belonging to Group 4 of the Periodic Table of the Elements (IUPAC Nomenclature of Inorganic Chemistry, revised in 1989) include titanium atom, zirconium atom and hafnium atom and preferably titanium atom.

Examples of the atom represented by $A^2$ and belonging to Group 16 of the Periodic Table of the Elements include oxygen atom, sulfur atom and selenium atom and preferably oxygen atom.

Examples of the atom represented by $J^4$ and belonging to Group 14 of the Periodic Table of the Elements include carbon atom, silicon atom and germanium atom, preferably carbon atom and silicon atom and more preferably carbon atom.

Examples of the group having a cyclopentadiene type anion skeleton represented by substituent $Cp^5$ include $\eta^5$-cyclopentadienyl group, $\eta^5$-methylcyclopentadienyl group, $\eta^5$-dimethylcyclopentadienyl group, $\eta^5$-trimethylcyclopentadienyl group, $\eta^5$-tetramethylcyclopentadienyl group, $\eta^5$-ethylcyclopentadienyl group, $\eta^5$-n-propylcyclopentadienyl group, $\eta^5$-isopropylcyclopentadienyl group, $\eta^5$-n-butylcyclopentadienyl group, $\eta^5$-sec-butylcyclopentadienyl group, $\eta^5$-tert-butylcyclopentadienyl group, $\eta^5$-n-pentylcyclopentadienyl group, $\eta^5$-neopentylcyclopentadienyl group, $\eta^5$-n-hexylcyclopentadienyl group, $\eta^5$-n-octylcyclopentadienyl group, $\eta^5$-phenylcyclopentadienyl group, $\eta^5$-naphthylcyclopentadienyl group, $\eta^5$-trimethylsilylcyclopentadienyl group, $\eta^5$-triethylsilylcyclopentadienyl group, $\eta^5$-tert-butyldimethylsilylcyclopentadienyl group, $\eta^5$-indenyl group, $\eta^5$-methylindenyl group, $\eta^5$-dimethylindenyl group, $\eta^5$-ethylindenyl group, $\eta^5$-n-propylindenyl group, $\eta^5$-isopropylindenyl group, $\eta^5$-n-butylindenyl group, $\eta^5$-sec-butylindenyl group, $\eta^5$-tert-butylindenyl group, $\eta^5$-n-pentylindenyl group, $\eta^5$-neopentylindenyl group, $\eta^5$-n-hexylindenyl group, $\eta^5$-n-octylindenyl group, $\eta^5$-n-decylindenyl group, $\eta^5$-phenylindenyl group, $\eta^5$-methylphenylindenyl group, $\eta^5$-naphthylindenyl group, $\eta^5$-trimethylsilylindenyl group, $\eta^5$-triethylsilylindenyl group, $\eta^5$-tert-butyldimethylsilylindenyl group, $\eta^5$-tetrahydroindenyl group, $\eta^5$-fluorenyl group, $\eta^5$-methylfluorenyl group, $\eta^5$-dimethylfluorenyl group, $\eta^5$-ethylfluorenyl group, $\eta^5$-diethylfluorenyl group, $\eta^5$-n-propylfluorenyl group, $\eta^5$-di-n-propylfluorenyl group, $\eta^5$-isopropylfluorenyl group, $\eta^5$-diisopropylfluorenyl group, $\eta^5$-n-butylfluorenyl group, re-sec-butylfluorenyl group, $\eta^5$-tert-butylfluorenyl group, $\eta^5$-di-n-butylfluorenyl group, $\eta^5$-di-sec-butylfluorenyl group, $\eta^5$-di-tert-butylfluorenyl group, $\eta^5$-n-pentylfluorenyl group, $\eta^5$-neopentylfluorenyl group, $\eta^5$-n-hexylfluorenyl group, $\eta^5$-n-octylfluorenyl group, $\eta^5$-n-decylfluorenyl group, $\eta^5$-n-dodecylfluorenyl group, $\eta^5$-phenylfluorenyl group, $\eta^5$-di-phenylfluorenyl group, $\eta^5$-methylphenylfluorenyl group, $\eta^5$-naphthylfluorenyl group, $\eta^5$-trimethylsilylfluorenyl group, $\eta^5$-bis-trimethylsilylfluorenyl group, re-triethylsilylfluorenyl group and $\eta^5$-tert-butyldimethylsilylfluorenyl group and preferably $\eta^5$-cyclopentadienyl group, $\eta^5$-methylcyclopentadienyl group, $\eta^5$-tert-butylcyclopentadienyl group, $\eta^5$-tetramethylcyclopentadienyl group, $\eta^5$-indenyl group and $\eta^5$-fluorenyl group.

In $X^{10}$, $X^{11}$, $R^{14}$, $R^{15}$, $R^{16}$ and $R^{17}$, examples of the halogen atom include fluorine atom, chlorine atom, bromine atom and iodine atom.

In $X^{10}$, $X^{11}$, $R^{14}$, $R^{15}$, $R^{16}$, $R^{17}$, $R^{18}$ and $R^{19}$, examples of the alkyl group having 1 to 20 carbon atoms include methyl group, ethyl group, n-propyl group, isopropyl group, n-butyl group, sec-butyl group, tert-butyl group, n-pentyl group, neopentyl group, amyl group, n-hexyl group, n-octyl group, n-decyl group, n-dodecyl group, n-pentadecyl group and n-eicosyl group.

Furthermore, "which may have a halogen atom as a substituent" of the "alkyl group which may have a halogen atom as a substituent" means that some or all hydrogen atoms in the alkyl group may be substituted with halogen atoms. Examples of the halogen atom include fluorine atom, chlorine atom, bromine atom and iodine atom. Examples of the alkyl group having 1 to 20 carbon atoms and having a halogen atom as a substituent include fluoromethyl group, difluoromethyl group, trifluoromethyl group, chloromethyl group, dichloromethyl group, trichloromethyl group, bromomethyl group, dibromomethyl group, tribromomethyl group, iodomethyl group, diiodomethyl group, triiodomethyl group, fluoroethyl group, difluoroethyl group, trifluoroethyl group, tetrafluoroethyl group, pentafluoroethyl group, chloroethyl group, dichloroethyl group, trichloroethyl group, tetrachloroethyl group, pentachloroethyl group, bromoethyl group, dibromoethyl group, tribromoethyl group, tetrabromoethyl group, pentabromoethyl group, perfluoropropyl group, perfluorobutyl group, perfluoropentyl group, perfluorohexyl group, perfluorooctyl group, perfluorododecyl group, perfluoropentadecyl group, perfluoroeicosyl group, perchloropropyl group, perchlorobutyl group, perchloropentyl group, perchlorohexyl group, perchlorooctyl group, perchlorododecyl group, perchloropentadecyl group, perchloroeicosyl group, perbromopropyl group, perbromobutyl group, perbromopentyl group, perbromohexyl group, perbromooctyl group, perbromododecyl group, perbromopentadecyl group and perbromoeicosyl group.

In $X^{10}$, $X^{11}$, $R^{14}$, $R^{15}$, $R^{16}$, $R^{17}$, $R^{18}$ and $R^{19}$, examples of the aryl group having 6 to 20 carbon atoms include phenyl group, 2-tolyl group, 3-tolyl group, 4-tolyl group, 2,3-xylyl group, 2,4-xylyl group, 2,5-xylyl group, 2,6-xylyl group, 3,4-xylyl group, 3,5-xylyl group, 2,3,4-trimethylphenyl group, 2,3,5-trimethylphenyl group, 2,3,6-trimethylphenyl group, 2,4,6-trimethylphenyl group, 3,4,5-trimethylphenyl group, 2,3,4,5-tetramethylphenyl group, 2,3,4,6-tetramethylphenyl group, 2,3,5,6-tetramethylphenyl group, pentamethylphenyl group, ethylphenyl group, n-propylphenyl group, isopropylphenyl group, n-butylphenyl group, sec-butylphenyl group, tert-butylphenyl group, n-pentylphenyl group, neopentylphenyl group, n-hexylphenyl group, n-octylphenyl group, n-decylphenyl group, n-dodecylphenyl group, n-tetradecylphenyl group, naphthyl group and anthracenyl group.

Furthermore, "which may have a halogen atom as a substituent" of the "aryl group which may have a halogen atom as a substituent" means that some or all hydrogen atoms in the aryl group may be substituted with halogen atoms. Examples of the halogen atom include fluorine atom, chlorine atom, bromine atom and iodine atom. Examples of an aryl group having 6 to 20 carbon atoms and a halogen atom as a substituent include fluorophenyl group, difluorophenyl group, trifluorophenyl group, tetrafluorophenyl group, pentafluorophenyl group, chlorophenyl group, bromophenyl group and iodophenyl group.

In $X^{10}$, $X^{11}$, $R^{14}$, $R^{15}$, $R^{16}$, $R^{17}$, $R^{18}$, and $R^{19}$, examples of the aralkyl group having 7 to 20 carbon atoms include benzyl group, (2-methylphenyl)methyl group, (3-methylphenyl)methyl group, (4-methylphenyl)methyl group, (2,3-dimethylphenyl)methyl group, (2,4-dimethylphenyl)methyl group, (2,5-dimethylphenyl)methyl group, (2,6-dimethylphenyl)methyl group, (3,4-dimethylphenyl)methyl group, (4,6-dimethylphenyl)methyl group, (2,3,4-trimethylphenyl)methyl group, (2,3,5-trimethylphenyl)methyl group, (2,3,6-trimethylphenyl)methyl group, (3,4,5-trimethylphenyl)methyl group, (2,4,6-trimethylphenyl)methyl group, (2,3,4,5-tetramethylphenyl)methyl group, (2,3,4,6-tetramethylphenyl)methyl group, (2,3,5,6-tetramethylphenyl)methyl group, (pentamethylphenyl)methyl group, (ethylphenyl)methyl group, (n-propylphenyl)methyl group, (isopropylphenyl)methyl group, (n-butylphenyl)methyl group, (sec-butylphenyl)methyl group, (tert-butylphenyl)methyl group, (n-pentylphenyl)methyl group, (neopentylphenyl)methyl group, (n-hexylphenyl)methyl group, (n-octylphenyl)methyl group, (n-decylphenyl)methyl group, (n-decylphenyl)methyl group, (n-tetradecylphenyl)methyl group, naphthyl methyl group and anthracenylmethyl group.

Furthermore, "which may have a halogen atom as a substituent" of the "aralkyl group which may have a halogen atom as a substituent" means that some or all hydrogen atoms in the aralkyl group may be substituted with halogen atoms. Examples of the halogen atom include fluorine atom, chlorine atom, bromine atom and iodine atom. Examples of the aralkyl group having 7 to 20 carbon atoms and a halogen atom as a substituent include the aforementioned aralkyl groups having hydrogen atoms wholly or partly substituted with halogen atoms.

In $X^{10}$, $X^{11}$, $R^{14}$, $R^{15}$, $R^{16}$, $R^{17}$, $R^{18}$, and $R^{19}$, examples of the alkoxy group having 1 to 20 carbon atoms include methoxy group, ethoxy group, n-propoxy group, isopropoxy group, n-butoxy group, sec-butoxy group, tert-butoxy group, n-pentoxy group, neopentoxy group, n-hexoxy group, n-octoxy group, n-dodesoxy group, n-pentadesoxy group and n-icosoxy group.

Furthermore, "which may have a halogen atom as a substituent" of the "an alkoxy group which may have a halogen atom as a substituent" means that some or all hydrogen atoms in the alkoxy group may be substituted with halogen atoms. Examples of the halogen atom include fluorine atom, chlorine atom, bromine atom and iodine atom. Examples of the alkoxy group having 1 to 20 carbon atoms and a halogen atom as a substituent include the aforementioned alkoxy groups having hydrogen atoms wholly or partly substituted with halogen atoms.

In $X^{10}$, $X^{11}$, $R^{14}$, $R^{15}$, $R^{16}$, $R^{17}$, $R^{18}$, and $R^{19}$, examples of the aryloxy group having 6 to 20 carbon atoms include aryloxy groups having 6 to 20 carbon atoms such as phenoxy group, 2-methylphenoxy group, 3-methylphenoxy group, 4-methylphenoxy group, 2,3-dimethylphenoxy group, 2,4-dimethylphenoxy group, 2,5-dimethylphenoxy group, 2,6-dimethylphenoxy group, 3,4-dimethylphenoxy group, 3,5-dimethylphenoxy group, 2,3,4-trimethylphenoxy group, 2,3,5-trimethylphenoxy group, 2,3,6-trimethylphenoxy group, 2,4,5-trimethylphenoxy group, 2,4,6-trimethylphenoxy group, 3,4,5-trimethylphenoxy group, 2,3,4,5-tetramethylphenoxy group, 2,3,4,6-tetramethylphenoxy group, 2,3,5,6-tetramethylphenoxy group, pentamethylphenoxy group, ethylphenoxy group, n-propylphenoxy group, isopropylphenoxy group, n-butylphenoxy group, sec-butylphenoxy group, tert-butylphenoxy group, n-hexylphenoxy group, n-octylphenoxy group, n-decylphenoxy group, n-tetradecylphenoxy group, naphthoxy group and anthracenoxy group.

Furthermore, "which may have a halogen atom as a substituent" of the "aryloxy group which may have a halogen atom as a substituent" means that some or all hydrogen atoms in the aryloxy group may be substituted with halogen atoms. Examples of the halogen atom include fluorine atom, chlorine atom, bromine atom and iodine atom.

Examples of the an aryloxy group having 6 to 20 carbon atoms and a halogen atom as a substituent include the aforementioned aryloxy groups having hydrogen atoms wholly or partly substituted with halogen atoms.

In $X^{10}$, $X^{11}$, $R^{14}$, $R^{15}$, $R^{16}$, $R^{17}$, $R^{18}$, and $R^{19}$, examples of the aralkyloxy group having 7 to 20 carbon atoms include benzyloxy group, (2-methylphenyl)methoxy group, (3-methylphenyl)methoxy group, (4-methylphenyl)methoxy group, (2,3-dimethylphenyl)methoxy group, (2,4-dimethylphenyl)methoxy group, (2,5-dimethylphenyl)methoxy group, (2,6-dimethylphenyl)methoxy group, (3,4-dimethylphenyl)methoxy group, (3,5-dimethylphenyl)methoxy group, (2,3,4-trimethylphenyl)methoxy group, (2,3,5-trimethylphenyl)methoxy group, (2,3,6-trimethylphenyl)methoxy group, (2,4,5-trimethylphenyl)methoxy group, (2,4,6-trimethylphenyl)methoxy group, (3,4,5-trimethylphenyl)methoxy group, (2,3,4,5-tetramethylphenyl)methoxy group, (2,3,4,6-tetramethylphenyl)methoxy group, (2,3,5,6-tetramethylphenyl)methoxy group, (pentamethylphenyl)methoxy group, (ethylphenyl)methoxy group, (n-propylphenyl)methoxy group, (isopropylphenyl)methoxy group, (n-butylphenyl)methoxy group, (sec-butylphenyl)methoxy group, (tert-butylphenyl)methoxy group, (n-hexylphenyl)methoxy group, (n-octylphenyl)methoxy group, (n-decylphenyl)methoxy group, (n-tetradecylphenyl)methoxy group, naphthylmethoxy group and anthracenylmethoxy group.

Furthermore, "which may have a halogen atom as a substituent" of the "aralkyloxy group which may have a halogen atom as a substituent" means that some or all hydrogen atoms in the aralkyloxy group may be substituted with halogen atoms. Examples of the halogen atom include fluorine atom, chlorine atom, bromine atom and iodine atom. Examples of the aralkyloxy group having 7 to 20 carbon atoms and a halogen atom as a substituent include the aforementioned aralkyloxy groups having hydrogen atoms wholly or partly substituted with halogen atoms.

In $X^{10}$, $X^{11}$, $R^{14}$, $R^{15}$, $R^{16}$, $R^{17}$, $R^{18}$, and $R^{19}$, the substituted silyl group represented by $-Si(R^{12})_3$, wherein the three $R^{12}$ groups each independently represent hydrogen atom, a hydrocarbyl group or a hydrocarbyl halide group, and the total number of the carbon atoms in the three $R^{12}$ groups is 1 to 20, the three $R^{12}$ groups each independently represent, hydrogen atom; a hydrocarbyl group such as an alkyl group having 1 to 10 carbon atoms (e.g., methyl group, ethyl group, n-propyl group, isopropyl group, n-butyl group, sec-butyl group, tert-butyl group, isobutyl group, n-pentyl group, n-hexyl group, cyclohexyl group, n-heptyl group, n-octyl group, n-nonyl group and n-decyl group) and aryl group (phenyl group, etc.); and hydrocarbyl halide group having hydrogen atoms whole or part of which are substituted with halogen atoms, and the total number of the carbon atoms in the three $R^{12}$ groups falls within the range of 1 to 20. The total number of the carbon atoms in the three $R^{12}$ groups is preferably within the range of 3 to 18. Specific examples of the substituted silyl group include a mono-substituted silyl group having either a hydrocarbyl group or a hydrocarbyl halide group, such as methylsilyl group, ethylsilyl group, phenylsilyl group, and groups obtained by substituting some or all hydrogen atoms of a hydrocarbyl group in these groups with halogen atoms; a disubstituted silyl group having two of hydrocarbyl groups and/or hydrocarbyl halide groups such as dimethylsilyl group, diethylsilyl group, diphenylsilyl group, and groups obtained by substituting some or all hydrogen atoms of a hydrocarbyl group in these groups with halogen atoms; and a tri-substituted silyl group having three of hydrocarbyl groups and/or hydrocarbyl halide groups, such as trimethylsilyl group, triethylsilyl group, tri-n-propylsilyl group, triisopropylsilyl group, tri-n-butylsilyl group, tri-sec-butylsilyl group, tri-tert-butylsilyl group, tri-isobutylsilyl group, tert-butyl-dimethylsilyl group, tri-n-pentylsilyl group, tri-n-hexylsilyl group, tricyclohexylsilyl group and triphenylsilyl group, and groups obtained by substituting some or all hydrogen atoms of a hydrocarbyl group in these groups with halogen atoms. Of these, a preferable substituted silyl group is tri-substituted silyl group, a further preferable substituted silyl group includes trimethylsilyl group, tert-butyldimethylsilyl group, triphenylsilyl group, and groups obtained by substituting some or all hydrogen atoms in these groups with halogen atoms.

In $X^{10}$, $X^{11}$, $R^{14}$, $R^{15}$, $R^{16}$, $R^{17}$, $R^{18}$, and $R^{19}$, the disubstituted amino group represented by $-N(R^{13})_2$, wherein the two $R^{13}$ groups each independently represent a hydrocarbyl group or a hydrocarbyl halide group, and the total number of the carbon atoms present in the two $R^{13}$ groups is 2 to 20, $R^{13}$ groups each independently represent a hydrocarbyl group or a hydrocarbyl halide group, and the total number of the carbon atoms in the two $R^{13}$ groups is within the range of 2 to 20 and further preferably within the range of 2 to 10. Such a hydrocarbyl group and hydrocarbyl halide group are the same as those described as the hydrocarbyl group and hydrocarbyl halide group of the aforementioned substituted silyl group. Furthermore, two $R^{13}$ groups may be mutually bonded to form a ring together with nitrogen atoms to which they are bonded. Examples of such a disubstituted amino group include dimethylamino group, diethylamino group, di-n-propylamino group, diisopropylamino group, di-n-butylamino group, di-sec-butylamino group, di-tert-butylamino group, di-isobutylamino group, tert-butylisopropylamino group, di-n-hexylamino group, di-n-octylamino group, di-n-decylamino group, diphenylamino group, bistrimethylsilylamino group, bis-tert-butyldimethylsilylamino group, pyrrolyl group, pyrrolidinyl group, piperidinyl group, carbazolyl group, dihydroindolyl group, dihydroisoindolyl group and groups obtained by substituting some or all hydrogen atoms in these groups with halogen atoms. Of these, a preferable disubstituted amino group includes dimethylamino group, diethylamino group, pyrrolidinyl group, piperidinyl group and groups obtained by substituting some or all hydrogen atoms in these groups with halogen atoms.

Of $R^{14}$, $R^{15}$, $R^{16}$ and $R^{17}$, two groups bonded to adjacent two carbon atoms may be bonded to form a ring together with the two carbon atoms to which they are bonded; and $R^{18}$ and $R^{19}$ may be bonded to form a ring together with $J^4$ to which they are bonded. As the ring, for example, a saturated or unsaturated hydrocarbyl ring may be mentioned. Specific examples of the ring include cyclopropane ring, cyclopropene ring, cyclobutane ring, cyclobutene ring, cyclopentane ring, cyclopentene ring, cyclohexane ring, cyclohexene ring, cycloheptane ring, cycloheptene ring, cyclooctane ring, cyclooctene ring, benzene ring, naphthalene ring, anthracene ring, silacyclopropane ring, silacyclobutane ring, silacyclopentane ring and silacyclohexane ring. These rings may be substituted with a hydrocarbyl group having 1 to 20 carbon atoms.

Preferable examples of substituents $X^{10}$ and $X^{11}$ include a halogen atom, an alkyl group having 1 to 20 carbon atoms which may have a halogen atom as a substituent, and an aralkyl group having 7 to 20 carbon atoms which may have a halogen atom as a substituent, and further preferable examples include a halogen atom.

Preferable examples of $R^{14}$ include an alkyl group having 1 to 20 carbon atoms which may have a halogen atom as a substituent, an aryl group having 6 to 20 carbon atoms which may have a halogen atom as a substituent, an aralkyl group having 7 to 20 carbon atoms which may have a halogen atom as a substituent, and a substituted silyl group represented by —Si $(R^{12})_3$, wherein the three $R^{12}$ groups each independently represent hydrogen atom and a hydrocarbyl group or a hydrocarbyl halide group, and the total number of the carbon atoms in the three $R^{12}$ groups is 1 to 20. Specific examples thereof include methyl group, ethyl group, isopropyl group, tert-butyl group, amyl group, phenyl group, benzyl group, trimethylsilyl group, tert-butyldimethylsilyl group and triphenylsilyl group. Further preferable examples thereof include tert-butyl group, trimethylsilyl group, tert-butyldimethylsilyl group and triphenylsilyl group.

A transition metal complex represented by the general formula (5) can be produced by a method described, for example, in JP 9-87313 A.

Examples of the complex represented by the general formula (5) include transition metal complexes represented by the general formula (5) where $J^4$ is carbon atom, such as methylene(cyclopentadienyl)(3,5-dimethyl-2-phenoxy)titanium dichloride, methylene(cyclopentadienyl)(3-tert-butyl-2-phenoxy)titanium dichloride, methylene(cyclopentadienyl)(3-tert-butyl-5-methyl-2-phenoxy)titanium dichloride, methylene(cyclopentadienyl)(3-phenyl-2-phenoxy)titanium dichloride, methylene(cyclopentadienyl)(3-tert-butyldimethylsilyl-5-methyl-2-phenoxy)titanium dichloride, methylene(cyclopentadienyl)(3-trimethylsilyl-5-methyl-2-phenoxy)titanium dichloride, methylene(cyclopentadienyl)(3-tert-butyl-5-methoxy-2-phenoxy)titanium dichloride, methylene(cyclopentadienyl)(3-tert-butyl-5-chloro-2-phenoxy)titanium dichloride, methylene(methylcyclopentadienyl)(3,5-dimethyl-2-phenoxy)titanium dichloride, methylene(methylcyclopentadienyl)(3-tert-butyl-2-phenoxy)titanium dichloride, methylene(methylcyclopentadienyl)(3-tert-butyl-5-methyl-2-phenoxy)titanium dichloride, methylene(methylcyclopentadienyl)(3-phenyl-2-phenoxy)titanium dichloride, methylene(methylcyclopentadienyl)(3-tert-butyldimethylsilyl-5-methyl-2-phenoxy)titanium dichloride, methylene(methylcyclopentadienyl)(3-trimethylsilyl-5-methyl-2-phenoxy)titanium dichloride, methylene(methylcyclopentadienyl)(3-tert-butyl-5-methoxy-2-phenoxy)titanium dichloride, methylene(methylcyclopentadienyl)(3-tert-butyl-5-chloro-2-phenoxy)titanium dichloride, methylene(tert-butylcyclopentadienyl)(3,5-dimethyl-2-phenoxy)titanium dichloride, methylene(tert-butylcyclopentadienyl)(3-tert-butyl-2-phenoxy)titanium dichloride, methylene(tert-butylcyclopentadienyl)(3-tert-butyl-5-methyl-2-phenoxy)titanium dichloride, methylene(tert-butylcyclopentadienyl)(3-phenyl-2-phenoxy)titanium dichloride, methylene(tert-butylcyclopentadienyl)(3-tert-butyldimethylsilyl-5-methyl-2-phenoxy)titanium dichloride, methylene(tert-butylcyclopentadienyl)(3-trimethylsilyl-5-methyl-2-phenoxy)titanium dichloride, methylene(tert-butylcyclopentadienyl)(3-tert-butyl-5-methoxy-2-phenoxy)titanium dichloride, methylene(tert-butylcyclopentadienyl)(3-tert-butyl-5-chloro-2-phenoxy)titanium dichloride, methylene(tetramethylcyclopentadienyl)(3,5-dimethyl-2-phenoxy)titanium dichloride, methylene(tetramethylcyclopentadienyl)(3-tert-butyl-2-phenoxy)titanium dichloride, methylene(tetramethylcyclopentadienyl)(3-tert-butyl-5-methyl-2-phenoxy)titanium dichloride, methylene(tetramethylcyclopentadienyl)(3-phenyl-2-phenoxy)titanium dichloride, methylene(tetramethylcyclopentadienyl)(3-tert-butyldimethylsilyl-5-methyl-2-phenoxy)titanium dichloride, methylene(tetramethylcyclopentadienyl)(3-trimethylsilyl-5-methyl-2-phenoxy)titanium dichloride, methylene(tetramethylcyclopentadienyl)(3-tert-butyl-5-methoxy-2-phenoxy)titanium dichloride, methylene(tetramethylcyclopentadienyl)(3-tert-butyl-5-chloro-2-phenoxy)titanium dichloride, methylene(trimethylsilylcyclopentadienyl)(3,5-dimethyl-2-phenoxy)titanium dichloride, methylene(trimethylsilylcyclopentadienyl)(3-tert-butyl-2-phenoxy)titanium dichloride, methylene(trimethylsilylcyclopentadienyl)(3-tert-butyl-5-methyl-2-phenoxy)titanium dichloride, methylene(trimethylsilylcyclopentadienyl)(3-phenyl-2-phenoxy)titanium dichloride, methylene(trimethylsilylcyclopentadienyl)(3-tert-butyldimethylsilyl-5-methyl-2-phenoxy)titanium dichloride, methylene(trimethylsilylcyclopentadienyl)(3-trimethylsilyl-5-methyl-2-phenoxy)titanium dichloride, methylene(trimethylsilylcyclopentadienyl)(3-tert-butyl-5-methoxy-2-phenoxy)titanium dichloride, methylene(trimethylsilylcyclopentadienyl)(3-tert-butyl-5-chloro-2-phenoxy)titanium dichloride, methylene(fluorenyl)(3,5-dimethyl-2-phenoxy)titanium dichloride, methylene(fluorenyl)(3-tert-butyl-2-phenoxy)titanium dichloride, methylene(fluorenyl)(3-tert-butyl-5-methyl-2-phenoxy)titanium dichloride, methylene(fluorenyl)(3-phenyl-2-phenoxy)titanium dichloride, methylene(fluorenyl)(3-tert-butyldimethylsilyl-5-methyl-2-phenoxy)titanium dichloride, methylene(fluorenyl)(3-trimethylsilyl-5-methyl-2-phenoxy)titanium dichloride, methylene(fluorenyl)(3-tert-butyl-5-methoxy-2-phenoxy)titanium dichloride, methylene(fluorenyl)(3-tert-butyl-5-chloro-2-phenoxy)titanium dichloride, isopropylidene(cyclopentadienyl)(3,5-dimethyl-2-phenoxy)titanium dichloride, isopropylidene(cyclopentadienyl)(3-tert-butyl-2-phenoxy)titanium dichloride, isopropylidene(cyclopentadienyl)(3-tert-butyl-5-methyl-2-phenoxy)titanium dichloride, isopropylidene(cyclopentadienyl)(3-phenyl-2-phenoxy)titanium dichloride, isopropylidene(cyclopentadienyl)(3-tert-butyldimethylsilyl-5-methyl-2-phenoxy)titanium dichloride, isopropylidene(cyclopentadienyl)(3-trimethylsilyl-5-methyl-2-phenoxy)titanium dichloride, isopropylidene(cyclopentadienyl)(3-tert-butyl-5-methoxy-2-phenoxy)titanium dichloride, isopropylidene(cyclopentadienyl)(3-tert-butyl-5-chloro-2-phenoxy)titanium dichloride, isopropylidene(methylcyclopentadienyl)(3,5-dimethyl-2-phenoxy)titanium dichloride, isopropylidene(methylcyclopentadienyl)(3-tert-butyl-2-phenoxy)titanium dichloride,- isopropylidene(methylcyclopentadienyl)(3-tert-butyl-5-methyl-2-phenoxy)titanium dichloride, isopropylidene(methylcyclopentadienyl)(3-phenyl-2-phenoxy)titanium dichloride, isopropylidene(methylcyclopentadienyl)(3-tert-butyldimethylsilyl-5-methyl-2-phenoxy)titanium dichloride, isopropylidene(methylcyclopentadienyl)(3-trimethylsilyl-5-methyl-2-phenoxy)titanium dichloride, isopropylidene(methylcyclopentadienyl)(3-tert-butyl-5-methoxy-2-phenoxy)titanium dichloride, isopropylidene(methylcyclopentadienyl)(3-tert-butyl-5-chloro-2-phenoxy)titanium dichloride, isopropylidene(tert-butylcyclopentadienyl)(3,5-dimethyl-2-phenoxy)titanium dichloride, isopropylidene(tert-butylcyclopentadienyl)(3-tert-butyl-2-phenoxy)titanium dichloride, isopropylidene(tert-butylcyclopentadienyl)(3-tert-butyl-5-methyl-2-phenoxy)titanium dichloride, isopropylidene(tert-butylcyclopentadienyl)(3-phenyl-2-phenoxy)titanium dichloride, isopropylidene(tert-butylcyclopentadienyl)(3-tert-butyldimethylsilyl-5-methyl-2-phenoxy)titanium dichloride, isopropylidene(tert-butylcyclopentadienyl)(3-trimethylsilyl-5-methyl-2-phenoxy)titanium dichloride, isopropylidene(tert-butylcyclopentadienyl)(3-tert-butyl-5-methoxy-2-phenoxy)titanium dichloride, isopropylidene(tert-butylcyclopentadienyl)(3-tert-butyl-5-chloro-2-phenoxy)titanium dichloride, isopropylidene(tetramethylcyclopentadienyl)(3,5-dimethyl-2-phenoxy)titanium di chloride, isopropylidene(tetramethylcyclopentadienyl)(3-tert-butyl-2-phenoxy)titanium dichloride, isopropylidene(tetramethylcyclopentadienyl)(3-tert-butyl-5-methyl-2-phenoxy)titanium dichloride, isopropylidene(tetramethylcyclopentadienyl)(3-phenyl-2-phenoxy)titanium dichloride, isopropylidene(tetramethylcyclopentadienyl)(3-tert-butyldimethylsilyl-5-methyl-2-phenoxy)titanium dichloride, isopropylidene(tetramethylcyclopentadienyl)(3-trimethylsilyl-5-methyl-2-phenoxy)titanium dichloride, isopropylidene(tetramethylcyclopentadienyl)(3-tert-butyl-5-methoxy-2-phenoxy)titanium dichloride, isopropylidene(tetramethylcyclopentadienyl)(3-tert-butyl-5-chloro-2-phenoxy)titanium dichloride, isopropylidene(trimethylsilylcyclopentadienyl)(3,5-dimethyl-2-phenoxy)titanium dichloride, isopropylidene(trimethylsilylcyclopentadienyl)(3-tert-butyl-2-phenoxy)titanium dichloride, isopropylidene(trimethylsilylcyclopentadienyl)(3-tert-butyl-5-methyl-2-phenoxy)titanium dichloride, isopropylidene(trimethylsilylcyclopentadienyl)(3-phenyl-2-phenoxy)titanium dichloride, isopropylidene(trimethylsilylcyclopentadienyl)(3-tert-butyldimethylsilyl-5-methyl-2-phenoxy)titanium dichloride, isopropylidene(trimethylsilylcyclopentadienyl)(3-trimethylsilyl-5-methyl-2-phenoxy)titanium dichloride, isopropylidene(trimethylsilylcyclopentadienyl)(3-tert-butyl-5-methoxy-2-phenoxy)titanium dichloride, isopropylidene(trimethylsilylcyclopentadienyl)(3-tert-butyl-5-chloro-2-phenoxy)titanium dichloride, isopropylidene(fluorenyl)(3,5-dimethyl-2-phenoxy)titanium dichloride, isopropylidene(fluorenyl)(3-tert-butyl-2-phenoxy)titanium dichloride, isopropylidene(fluorenyl)(3-tert-butyl-5-methyl-2-phenoxy)titanium dichloride, isopropylidene(fluorenyl)(3-phenyl-2-phenoxy)titanium dichloride, isopropylidene(fluorenyl)(3-tert-butyldimethylsilyl-5-methyl-2-phenoxy)titanium dichloride, isopropylidene(fluorenyl)(3-trimethylsilyl-5-methyl-2-phenoxy)titanium dichloride, isopropylidene(fluorenyl)(3-tert-butyl-5-methoxy-2-phenoxy)titanium dichloride, isopropylidene(fluorenyl)(3-tert-butyl-5-chloro-2-phenoxy)titanium dichloride, diphenylmethylene(cyclopentadienyl)(3,5-dimethyl-2-phenoxy)titanium dichloride, diphenylmethylene(cyclopentadienyl)(3-tert-butyl-2-phenoxy)titanium dichloride, diphenylmethylene(cyclopentadienyl)(3-tert-butyl-5-methyl-2-phenoxy)titanium dichloride, diphenylmethylene(cyclopentadienyl)(3-phenyl-2-phenoxy)titanium dichloride, diphenylmethylene(cyclopentadienyl)(3-tert-butyldimethylsilyl-5-methyl-2-phenoxy)titanium dichloride, diphenylmethylene(cyclopentadienyl)(3-trimethylsilyl-5-methyl-2-phenoxy)titanium dichloride, diphenylmethylene(cyclopentadienyl)(3-tert-butyl-5-methoxy-2-phenoxy)titanium dichloride, diphenylmethylene(cyclopentadienyl)(3-tert-butyl-5-chloro-2-phenoxy)titanium dichloride, diphenylmethylene(methylcyclopentadienyl)(3,5-dimethyl-2-phenoxy)titanium dichloride, diphenylmethylene(methylcyclopentadienyl)(3-tert-butyl-2-phenoxy)titanium dichloride, diphenylmethylene(methylcyclopentadienyl)(3-tert-butyl-5-methyl-2-phenoxy)titanium dichloride, diphenylmethylene(methylcyclopentadienyl)(3-phenyl-2-phenoxy)titanium dichloride, diphenylmethylene(methylcyclopentadienyl)(3-tert-butyldimethylsilyl-5-methyl-2-phenoxy)titanium dichloride, diphenylmethylene(methylcyclopentadienyl)(3-trimethylsilyl-5-methyl-2-phenoxy)titanium dichloride, diphenylmethylene(methylcyclopentadienyl)(3-tert-butyl-5-methoxy-2-phenoxy)titanium dichloride, diphenylmethylene(methylcyclopentadienyl)(3-tert-butyl-5-chloro-2-phenoxy)titanium dichloride, diphenylmethylene(tert-butylcyclopentadienyl)(3,5-dimethyl-2-phenoxy)titanium dichloride, diphenylmethylene(tert-butylcyclopentadienyl)(3-tert-butyl-2-phenoxy)titanium dichloride, diphenylmethylene(tert-butylcyclopentadienyl)(3-tert-butyl-5-methyl-2-phenoxy)titanium dichloride, diphenylmethylene(tert-butylcyclopentadienyl)(3-phenyl-2-phenoxy)titanium dichloride, diphenylmethylene(tert-butylcyclopentadienyl)(3-tert-butyldimethylsilyl-5-methyl-2-phenoxy)titanium dichloride, diphenylmethylene(tert-butylcyclopentadienyl)(3-trimethylsilyl-5-methyl-2-phenoxy)titanium dichloride, diphenylmethylene(tert-butylcyclopentadienyl)(3-tert-butyl-5-methoxy-2-phenoxy)titanium dichloride, diphenylmethylene(tert-butylcyclopentadienyl)(3-tert-butyl-5-chloro-2-phenoxy)titanium dichloride, diphenylmethylene(tetramethylcyclopentadienyl)(3,5-dimethyl-2-phenoxy)titanium dichloride, diphenylmethylene(tetramethylcyclopentadienyl)(3-tert-butyl-2-phenoxy)titanium dichloride, diphenylmethylene(tetramethylcyclopentadienyl)(3-tert-butyl-5-methyl-2-phenoxy)titanium dichloride, diphenylmethylene(tetramethylcyclopentadienyl)(3-phenyl-2-phenoxy)titanium dichloride, diphenylmethylene(tetramethylcyclopentadienyl)(3-tert-butyldimethylsilyl-5-methyl-2-phenoxy)titanium dichloride, diphenylmethylene(tetramethylcyclopentadienyl)(3-trimethylsilyl-5-methyl-2-phenoxy)titanium dichloride, diphenylmethylene(tetramethylcyclopentadienyl)(3-tert-butyl-5-methoxy-2-phenoxy)titanium dichloride, diphenylmethylene(tetramethylcyclopentadienyl)(3-tert-butyl-5-chloro-2-phenoxy)titanium dichloride, diphenylmethylene(trimethylsilylcyclopentadienyl)(3,5-dimethyl-2-phenoxy)titanium dichloride, diphenylmethylene(trimethylsilylcyclopentadienyl)(3-tert-butyl-2-phenoxy)titanium dichloride, diphenylmethylene(trimethylsilylcyclopentadienyl)(3-tert-butyl-5-methyl-2-phenoxy)titanium dichloride, diphenylmethylene(trimethylsilylcyclopentadienyl)(3-phenyl-2-phenoxy)titanium dichloride, diphenylmethylene(trimethylsilylcyclopentadienyl)(3-tert-butyldimethylsilyl-5-methyl-2-phenoxy)titanium dichloride, diphenylmethylene(trimethylsilylcyclopentadienyl)(3-trimethylsilyl-5-methyl-2-phenoxy)titanium dichloride, diphenylmethylene(trimethylsilylcyclopentadienyl)(3-tert-butyl-5-methoxy-2-phenoxy)titanium dichloride, diphenylmethylene(trimethylsilylcyclopentadienyl)(3-tert-butyl-5-chloro-2-phenoxy)titanium dichloride, diphenylmethylene(fluorenyl)(3,5-dimethyl-2-phenoxy)titanium dichloride, diphenylmethylene(fluorenyl)(3-tert-butyl-2-phenoxy)titanium dichloride, diphenylmethylene(fluorenyl)(3-tert-butyl-5-methyl-2-phenoxy)titanium dichloride, diphenylmethylene(fluorenyl)(3-phenyl-2-phenoxy)titanium dichloride, diphenylmethylene(fluorenyl)(3-tert-butyldimethylsilyl-5-methyl-2-phenoxy)titanium dichloride, diphenylmethylene(fluorenyl)(3-trimethylsilyl-5-methyl-2-phenoxy)titanium dichloride, diphenylmethylene(fluorenyl)(3-tert-butyl-5-methoxy-2-phenoxy)titanium dichloride and diphenylmethylene(fluorenyl)(3-tert-butyl-5-chloro-2-phenoxy)titanium dichloride; and compounds obtained by substituting zirconium or hafnium for titanium of these compounds, compounds obtained by substituting bromide, iodide, hydride, methyl, phenyl, benzyl, methoxide, n-butoxide, isopropoxide, phenoxide, benzyloxide, dimethylamide or diethylamide for chloride of these compounds, compounds obtained by substituting (dimethylcyclopentadienyl), (trimethylcyclopentadienyl), (n-butylcyclopentadienyl), (tert-butyldimethylsilylcyclopentadienyl) or (indenyl) for (cyclopentadienyl) of these compounds, compounds obtained by substituting 2-phenoxy, 3-methyl-2-phenoxy, 3,5-di-tert-butyl-2-phenoxy, 3-phenyl-5-methyl-2-phenoxy, 3-tert-butyldimethylsilyl-2-phenoxy or 3-trimethylsilyl-2-phenoxy for 3,5-dimethyl-2-phenoxy and compounds obtained by substituting diethylmethylene for methylene; and transition metal compounds represented by the general formula (5) where $J^4$ is an atom of Group 14 of the Periodic Table of the Elements other than carbon atom such as dimethylsilylene(cyclopentadienyl)(2-phenoxy)titanium dichloride, dimethylsilylene(cyclopentadienyl)(3-methyl-2-phenoxy)titanium dichloride, dimethylsilylene(cyclopentadienyl)(3,5-dimethyl-2-phenoxy)titanium dichloride, dimethylsilylene(cyclopentadienyl)(3-tert-butyl-2-phenoxy)titanium dichloride, dimethylsilylene(cyclopentadienyl)(3-tert-butyl-5-methyl-2-phenoxy)titanium dichloride, dimethylsilylene(cyclopentadienyl)(3,5-di-tert-butyl-2-phenoxy)titanium dichloride, dimethylsilylene(cyclopentadienyl)(5-methyl-3-phenyl-2-phenoxy)titanium dichloride, dimethylsilylene(cyclopentadienyl)(3-tert-butyldimethylsilyl-5-methyl-2-phenoxy)titanium dichloride, dimethylsilylene(cyclopentadienyl)(5-methyl-3-trimethylsilyl-2-phenoxy)titanium dichloride, dimethylsilylene(cyclopentadienyl)(3-tert-butyl-5-methoxy-2-phenoxy)titanium dichloride, dimethylsilylene(cyclopentadienyl)(3-tert-butyl-5-chloro-2-phenoxy)titanium dichloride, dimethylsilylene(cyclopentadienyl)(3,5-diamyl-2-phenoxy)titanium dichloride,
dimethylsilylene(methylcyclopentadienyl)(2-phenoxy)titanium dichloride, dimethylsilylene(methylcyclopentadienyl)(3-methyl-2-phenoxy)titanium dichloride, dimethylsilylene(methylcyclopentadienyl)(3,5-dimethyl-2-phenoxy)titanium dichloride, dimethylsilylene(methylcyclopentadienyl)(3-tert-butyl-2-phenoxy)titanium dichloride, dimethylsilylene(methylcyclopentadienyl)(3-tert-butyl-5-methyl-2-phenoxy)titanium dichloride, dimethylsilylene(methylcyclopentadienyl)(3,5-di-tert-butyl-2-phenoxy)titanium dichloride, dimethylsilylene(methylcyclopentadienyl)(5-methyl-3-phenyl-2-phenoxy)titanium dichloride, dimethylsilylene(methylcyclopentadienyl)(3-tert-butyldimethylsilyl-5-methyl-2-phenoxy)titanium dichloride, dimethylsilylene(methylcyclopentadienyl)(5-methyl-3-trimethylsilyl-2-phenoxy)titanium dichloride, dimethylsilylene(methylcyclopentadienyl)(3-tert-butyl-5-methoxy-2-phenoxy)titanium dichloride, dimethylsilylene(methylcyclopentadienyl)(3-tert-butyl-5-chloro-2-phenoxy)titanium dichloride, dimethylsilylene(methylcyclopentadienyl)(3,5-diamyl-2-phenoxy)titanium dichloride,
dimethylsilylene(n-butylcyclopentadienyl)(2-phenoxy)titanium dichloride, dimethylsilylene(n-butylcyclopentadienyl)(3-methyl-2-phenoxy)titanium dichloride, dimethylsilylene(n butylcyclopentadienyl)(3,5-dimethyl-2-phenoxy)titanium dichloride, dimethylsilylene(n-butylcyclopentadienyl)(3-tert-butyl-2-phenoxy)titanium dichloride, dimethylsilylene(n-butylcyclopentadienyl)(3-tert-butyl-5-methyl-2-phenoxy)titanium dichloride, dimethylsilylene(n-butylcyclopentadienyl)(3,5-di-tert-butyl-2-phenoxy)titanium dichloride, dimethylsilylene(n-butylcyclopentadienyl)(5-methyl-3-phenyl-2-phenoxy)titanium dichloride, dimethylsilylene(n-butylcyclopentadienyl)(3-tert-butyldimethylsilyl-5-methyl-2-phenoxy)titanium dichloride, dimethylsilylene(n-butylcyclopentadienyl)(5-methyl-3-trimethylsilyl-2-phenoxy)titanium dichloride, dimethylsilylene(n-butylcyclopentadienyl)(3-tert-butyl-5-methoxy-2-phenoxy)titanium dichloride, dimethylsilylene(n-butylcyclopentadienyl)(3-tert-butyl-5-chloro-2-phenoxy)titanium dichloride, dimethylsilylene(n-butylcyclopentadienyl)(3,5-diamyl-2-phenoxy)titanium dichloride,
dimethylsilylene(tert-butylcyclopentadienyl)(2-phenoxy)titanium dichloride, dimethylsilylene(tert-butylcyclopentadienyl)(3-methyl-2-phenoxy)titanium dichloride, dimethylsilylene(tert-butylcyclopentadienyl)(3,5-dimethyl-2-phenoxy)titanium dichloride, dimethylsilylene(tert-butylcyclopentadienyl)(3-tert-butyl-2-phenoxy)titanium dichloride, dimethylsilylene(tert-butylcyclopentadienyl)(3-tert-butyl-5-methyl-2-phenoxy)titanium dichloride, dimethylsilylene(tert-butylcyclopentadienyl)(3,5-di-tert-butyl-2-phenoxy)titanium dichloride, dimethylsilylene(tert-butylcyclopentadienyl)(5-methyl-3-phenyl-2-phenoxy)titanium dichloride, dimethylsilylene(tert-butylcyclopentadienyl)(3-tert-butyldimethylsilyl-5-methyl-2-phenoxy)titanium dichloride, dimethylsilylene(tert-butylcyclopentadienyl)(5-methyl-3-trimethylsilyl-2-phenoxy)titanium dichloride, dimethylsilylene(tert-butylcyclopentadienyl)(3-tert-butyl-5-methoxy-2-phenoxy)titanium dichloride, dimethylsilylene(tert-butylcyclopentadienyl)(3-tert-butyl-5-chloro-2-phenoxy)titanium dichloride, dimethylsilylene(tert-butylcyclopentadienyl)(3,5-diamyl-2-phenoxy)titanium dichloride,
dimethylsilylene(tetramethylcyclopentadienyl)(2-phenoxy)titanium dichloride, dimethylsilylene(tetramethylcyclopentadienyl)(3-methyl-2-phenoxy)titanium dichloride, dimethylsilylene(tetramethylcyclopentadienyl)(3,5-dimethyl-2-phenoxy)titanium dichloride, dimethylsilylene(tetramethylcyclopentadienyl)(3-tert-butyl-2-phenoxy)titanium dichloride, dimethylsilylene(tetramethylcyclopentadienyl)(3-tert-butyl-5-methyl-2-phenoxy)titanium dichloride, dimethylsilylene(tetramethylcyclopentadienyl)(3,5-di-tert-butyl-2-phenoxy)titanium dichloride, dimethylsilylene(tetramethylcyclopentadienyl)(5-methyl-3-phenyl-2-phenoxy)titanium dichloride, dimethylsilylene(tetramethylcyclopentadienyl)(3-tert-butyldimethylsilyl-5-methyl-2-phenoxy)titanium dichloride, dimethylsilylene(tetramethylcyclopentadienyl)(5-methyl-3-trimethylsilyl-2-phenoxy)titanium dichloride, dimethylsilylene(tetramethylcyclopentadienyl)(3-tert-butyl-5-methoxy-2-phenoxy)titanium dichloride, dimethylsilylene(tetramethylcyclopentadienyl)(3-tert-butyl-5-chloro-2-phenoxy)titanium dichloride, dimethylsilylene(tetramethylcyclopentadienyl)(3,5-diamyl-2-phenoxy)titanium dichloride,
dimethylsilylene(trimethylsilylcyclopentadienyl)(2-phenoxy)titanium dichloride, dimethylsilylene(trimethylsilylcyclopentadienyl)(3-methyl-2-phenoxy)titanium dichloride, dimethylsilylene(trimethylsilylcyclopentadienyl)(3,5-dimethyl-2-phenoxy)titanium dichloride, dimethylsilylene(trimethylsilylcyclopentadienyl)(3-tert-butyl-2-phenoxy)titanium dichloride, dimethylsilylene(trimethylsilylcyclopentadienyl)(3-tert-butyl-5-methyl-2-phenoxy)titanium dichloride, dimethylsilylene(trimethylsilylcyclopentadienyl)(3,5-di-tert-butyl-2-phenoxy)titanium dichloride, dimethylsilylene (trimethylsilylcyclopentadienyl)(5-methyl-3-phenyl-2-phenoxy)titanium dichloride, dimethylsilylene(trimethylsilylcyclopentadienyl)(3-tert-butyldimethylsilyl-5-methyl-2-phenoxy)titanium dichloride, dimethylsilylene (trimethylsilylcyclopentadienyl)(5-methyl-3-trimethylsilyl-2-phenoxy)titanium dichloride, dimethylsilylene (trimethylsilylcyclopentadienyl)(3-tert-butyl-5-methoxy-2-phenoxy)titanium dichloride, dimethylsilylene (trimethylsilylcyclopentadienyl)(3-tert-butyl-5-chloro-2-phenoxy)titanium dichloride, dimethylsilylene (trimethylsilylcyclopentadienyl)(3,5-diamyl-2-phenoxy) titanium dichloride,
dimethylsilylene(indenyl)(2-phenoxy)titanium dichloride, dimethylsilylene(indenyl)(3-methyl-2-phenoxy)titanium dichloride, dimethylsilylene(indenyl)(3,5-dimethyl-2-phenoxy)titanium dichloride, dimethylsilylene(indenyl)(3-tert-butyl-2-phenoxy)titanium dichloride, dimethylsilylene(indenyl)(3-tert-butyl-5-methyl-2-phenoxy)titanium dichloride, dimethylsilylene(indenyl)(3,5-di-tert-butyl-2-phenoxy)titanium dichloride, dimethylsilylene(indenyl)(5-methyl-3-phenyl-2-phenoxy)titanium dichloride, dimethylsilylene(indenyl)(3-tert-butyldimethylsilyl-5-methyl-2-phenoxy)titanium dichloride, dimethylsilylene(indenyl)(5-methyl-3-trimethylsilyl-2-phenoxy)titanium dichloride, dimethylsilylene(indenyl)(3-tert-butyl-5-methoxy-2-phenoxy)titanium dichloride, dimethylsilylene(indenyl)(3-tert-butyl-5-chloro-2-phenoxy) titanium dichloride, dimethylsilylene(indenyl)(3,5-diamyl-2-phenoxy)titanium dichloride,
dimethylsilylene(fluorenyl)(2-phenoxy)titanium dichloride, dimethylsilylene(fluorenyl)(3-methyl-2-phenoxy)titanium dichloride, dimethylsilylene(fluorenyl)(3,5-dimethyl-2-phenoxy)titanium dichloride, dimethylsilylene(fluorenyl)(3-tert-butyl-2-phenoxy)titanium dichloride, dimethylsilylene (fluorenyl)(3-tert-butyl-5-methyl-2-phenoxy)titanium dichloride, dimethylsilylene(fluorenyl)(3,5-di-tert-butyl-2-phenoxy)titanium dichloride, dimethylsilylene(fluorenyl)(5-methyl-3-phenyl-2-phenoxy)titanium dichloride, dimethylsilylene(fluorenyl)(3-tert-butyldimethylsilyl-5-methyl-2-phenoxy)titanium dichloride, dimethylsilylene(fluorenyl)(5-methyl-3-trimethylsilyl-2-phenoxy)titanium dichloride, dimethylsilylene(fluorenyl)(3-tert-butyl-5-methoxy-2-phenoxy)titanium dichloride, dimethylsilylene(fluorenyl)(3-tert-butyl-5-chloro-2-phenoxy)titanium dichloride, dimethylsilylene(fluorenyl)(3,5-diamyl-2-phenoxy)titanium dichloride and dimethylsilylene(tetramethylcyclopentadienyl)(1-naphthoxy-2-yl)titanium dichloride; and compounds obtained by substituting (dimethylcyclopentadienyl), (trimethylcyclopentadienyl), (ethylcyclopentadienyl), (n-propylcyclopentadienyl), (isopropylcyclopentadienyl), (sec-butylcyclopentadienyl), (isobutylcyclopentadienyl), (tert-butyldimethylsilylcyclopentadienyl), (phenylcyclopentadienyl), (methylindenyl) or (phenylindenyl) for (cyclopentadienyl) of these compounds, compounds obtained by substituting 3-phenyl-2-phenoxy, 3-trimethylsilyl-2-phenoxy or 3-tert-butyldimethylsilyl-2-phenoxy for 2-phenoxy of these compounds, compounds obtained by substituting diethylsilylene, diphenylsilylene or dimethoxysilylene for dimethylsilylene of these compounds, compounds obtained by substituting zirconium or hafnium for titanium of these compounds, and compounds obtained by substituting bromide, iodide, hydride, methyl, phenyl, benzyl, methoxide, n-butoxide, isopropoxide, phenoxide, benzyloxide, dimethylamide or diethylamide for chloride of these compounds.

Preferable examples of the transition metal complex of the formula (1) include methylphenylsilylene(tetramethylcyclopentadienyl)(3-tert-butyl-5-methyl-2-phenoxy)titanium dichloride and dimethylsilylene(tetramethylcyclopentadienyl)(3-tert-butyl-5-methyl-2-phenoxy)titanium dichloride.

<Activating Co-Catalyst Component>

Examples of an activating co-catalyst component include the following compound (A) and compound (B). Compound (A) and compound (B) may be used in combination.

Compound (A): at least one aluminum compound selected from the group of compounds consisting of the following compounds (A1) to (A3):

(A1): an organic aluminum compound represented by the general formula $(E^1)_a Al(G)_{3-a}$, (A2): a cyclic aluminoxane having the structure represented by the general formula $\{—Al(E^2)—O—\}_b$, (A3): a linear aluminoxane having the structure represented by the general formula $E^3\{—Al(E^3)—O—\}_c Al(E^3)_2$, wherein $E^1$, $E^2$ and $E^3$ represent a hydrocarbyl group having 1 to 8 carbon atoms, G represents hydrogen atom or a halogen atom, a represents an integer of 1 to 3, b represents an integer of 2 or more, and c represents an integer of 1 or more; in the case that more than one $E^1$ groups exist, the $E^1$ groups may be the same as or different from each other; in the case that more than one G groups exist, the G groups may be the same as or different from each other; a plurality of $E^2$ groups may be the same as or different from each other; and a plurality of $E^3$ groups may be the same as or different from each other.

Compound (B): at least one boron compound selected from the group of compounds consisting of the following compounds (B1) to (B3):

(B1): a boron compound represented by the general formula $BQ^1 Q^2 Q^3$, (B2): a borate compound represented by the general formula $T^+(BQ^1 Q^2 Q^3 Q^4)^-$, (B3): a borate compound represented by the general formula $(L-H)^+(BQ^1 Q^2 Q^3 Q^4)^-$ wherein B represents a trivalent boron; $Q^1$, $Q^2$, $Q^3$ and $Q^4$ are the same as or different from each other and represent a hydrocarbyl group having 1 to 20 carbon atoms, a hydrocarbylsilyl group having 1 to 20 carbon atoms, an alkoxy group having 1 to 20 carbon atoms or a dihydrocarbylamino group having 2 to 20 carbon atoms, which may be substituted with a halogen atom and a halogen atom; $T^+$ represents an inorganic or organic cation; and $(L-H)^+$ represents a Broensted acid.

In the compounds (A1) to (A3), as a hydrocarbyl group having 1 to 8 carbon atoms represented by $E^1$, $E^2$ and $E^3$, for example, an alkyl having 1 to 8 carbon atoms is mentioned. Examples of the alkyl group having 1 to 8 carbon atoms include methyl group, ethyl group, normal propyl group, isopropyl group, normal butyl group, isobutyl group, normal pentyl group and neopentyl group.

Examples of the organic aluminum compound (A1) represented by the general formula $(E^1)_a Al(G)_{3-a}$ include trialkylaluminum, dialkylaluminum chloride, alkylaluminum dichloride and dialkylaluminum hydride. Examples of the trialkylaluminum include trimethylaluminum, triethylaluminum, tripropylaluminum, triisobutylaluminum and trihexylaluminum. Examples of the dialkylaluminum chloride include dimethylaluminum chloride, diethylaluminum chloride, dipropylaluminum chloride, diisobutylaluminum chloride and dihexylaluminum chloride. Examples of the alkylaluminum dichloride include methylaluminum dichloride, ethylaluminum dichloride, propylaluminum dichloride, isobutylaluminum dichloride and hexylaluminum dichloride. Examples of dialkylaluminum hydride include dimethylaluminum hydride, diethylaluminum hydride, dipropylaluminum hydride, diisobutylaluminum hydride and dihexylaluminum hydride.

In (A2) cyclic aluminoxanes having a structure represented by the formula $\{—Al(E^2)—O-\}_1$, or (A3) linear aluminoxanes having a structure represented by the formula $E^3\{—Al(E^3)—O-\}_c AlE^3_2$, examples of groups represented by $E^2$ and $E^3$ include alkyl groups such as methyl group, ethyl group, normal propyl group, isopropyl group, normal butyl group, isobutyl group, normal pentyl group and neopentyl group; b is an integer of 2 or more; and c is an integer of 1 or more. Preferably, $E^2$ and $E^3$ are each independently methyl group or isobutyl group; b is 2 to 40 and c is 1 to 40.

The aforementioned aluminoxanes can be produced by various methods. The method is not particularly limited. The aluminoxane may be produced in accordance with a method known in the art. Examples thereof include a method for producing an aluminoxane by bringing a solution, which is obtained by dissolving trialkylaluminum (for example, trimethylaluminum) in an appropriate organic solvent (benzene, aliphatic hydrocarbyl, etc.), into contact with water and a method for producing an aluminoxane by bringing trialkylaluminum (for example, trimethylaluminum) into contact with a metal salt containing crystal water (for example, copper sulfate hydrate).

In the compounds (B1) to (B3), $Q^1$, $Q^2$, $Q^3$ and $Q^4$ preferably represent a halogen atom or a hydrocarbyl group having 1 to 20 carbon atoms which may be substituted with a halogen atom. Examples of the inorganic cation represented by $T^+$ include a ferrocenium cation, an alkyl-substituted ferrocenium cation and a silver cation. Examples of the organic cation include a triphenylmethyl cation. Examples of $(BQ^1Q^2Q^3Q^4)^-$ include tetrakis(pentafluorophenyl)borate, tetrakis(2,3,5,6-tetrafluorophenyl)borate, tetrakis(2,3,4,5-tetrafluorophenyl)borate, tetrakis(3,4,5-trifluorophenyl)borate, tetrakis(2,3,4-trifluorophenyl)borate, phenyltris(pentafluorophenyl)borate and tetrakis(3,5-bistrifluoromethylphenyl)borate. Examples of $(L-H)^+$ representing a Broensted acid include trialkyl-substituted ammonium, N,N-dialkylanilinium, dialkylammonium and triarylphosphonium.

Examples of the boron compound (B1) represented by the general formula $BQ^1Q^2Q^3$ include tris(pentafluorophenyl)borane, tris(2,3,5,6-tetrafluorophenyl)borane, tris(2,3,4,5-tetrafluorophenyl)borane, tris(3,4,5-trifluorophenyl)borane, tris(2,3,4-trifluorophenyl)borane and phenylbis(pentafluorophenyl)borane.

Examples of the borate compound (B2) represented by the general formula $T^+(BQ^1Q^2Q^3Q^4)^-$ include ferrocenium tetrakis(pentafluorophenyl)borate, 1,1'-bis-trimethylsilylferrocenium tetrakis(pentafluorophenyl)borate, silver tetrakis(pentafluorophenyl)borate, triphenylmethyl tetrakis(pentafluorophenyl)borate and triphenylmethyl tetrakis(3,5-bistrifluoromethylphenyl)borate.

Examples of the borate compound (B3) represented by the general formula $(L-H)^+(BQ^1Q^2Q^3Q^4)^-$ include triethylammonium tetrakis(pentafluorophenyl)borate, tripropylammonium tetrakis(pentafluorophenyl)borate, tri(normal-butyl)ammonium tetrakis(pentafluorophenyl)borate, tri(normal-butyl)ammonium tetrakis(3,5-bistrifluoromethylphenyl)borate, N,N-bis-trimethylsilylanilinium tetrakis(pentafluorophenyl)borate, N,N-diethylanilinium tetrakis(pentafluorophenyl)borate, N,N-2,4,6-pentamethylanilinium tetrakis(pentafluorophenyl)borate, N,N-bis-trimethylsilylanilinium tetrakis(3,5-bistrifluoromethylphenyl)borate, diisopropylammonium tetrakis(pentafluorophenyl)borate, dicyclohexylammonium tetrakis(pentafluorophenyl)borate, triphenylphosphonium tetrakis(pentafluorophenyl)borate, tri(methylphenyl)phosphonium tetrakis(pentafluorophenyl)borate and tri(bis-trimethylsilylphenyl)phosphonium tetrakis(pentafluorophenyl)borate.

<Catalyst for Olefin Polymerization>

A catalyst for olefin polymerization for use in producing the ethylenic polymer of the present invention is a catalyst obtained by bringing transition metal complex (1) represented by the general formula (1), transition metal complex (5) represented by the general formula (5) and the aforementioned activating co-catalyst component into contact with each other.

The amounts of the individual catalytic components to be used, more specifically, the molar ratio (transition metal complex (1)/transition metal complex (5)), which is the molar ratio of transition metal complex (1) to transition metal complex (5), is usually 0.0001 to 100, preferably 0.001 to 1, more preferably, 0.005 to 0.5, and further preferably, 0.01 to 0.15.

The amounts of the individual catalytic components to be used, more specifically, the molar ratio (compound (A) (in terms of aluminum atom)/transition metal complex), which is the molar ratio of compound (A) (in terms of aluminum atom) to the transition metal complexes (total of transition metal complex (1) and transition metal complex (5)) serving as the catalytic component, is usually 0.01 to 10000 and preferably 5 to 5000. Furthermore, the molar ratio (compound (B)/transition metal complex), which is the molar ratio of compound (B) to the transition metal complexes (total of transition metal complex (1) and transition metal complex (5)) serving as the catalytic component, is usually 0.01 to 100 and preferably 0.5 to 10.

Furthermore, the molar ratio (aluminum atom in compound (A)/titanium atom in solid catalytic component), which is the molar ratio of the aluminum atom in compound (A) to the titanium atom in the solid catalytic component, is usually 1 to 10000, preferably 1 to 2000 and more preferably 2 to 600.

When the catalytic components are used in a solution, the concentration of the transition metal complex serving as the catalytic component is usually 0.0001 to 5 mmol/liter, preferably, 0.001 to 2 mmol/liter, and more preferably 0.01 to 1 mmol/liter. The concentration of compound (A) in terms of aluminum atom is usually 0.01 to 500 mmol/liter and preferably 5 to 200 mmol/liter. The concentration of compound (B) is usually 0.0001 to 5 mmol/liter, preferably, 0.001 to 2 mmol/liter, and more preferably 0.01 to 1 mmol/liter.

The catalytic components may be supported on a carrier. As the carrier, a porous substance is preferably used, an inorganic substance or an organic polymer is more preferably used, and an inorganic substance is further preferably used. The carrier will be described later.

A method of bringing catalytic components into contact with each other is not particularly limited. Transition metal complex (1), transition metal complex (5) and an activating co-catalyst component can be brought into contact with each other in advance to prepare a polymerization catalyst, and then the polymerization catalyst can be supplied to a polymerization reactor. Alternatively, the catalytic components can be supplied to a polymerization reactor in any order and then allowed to be in contact with each other in the polymerization reactor. To the polymerization reactor, transition metal complex (1) and transition metal complex (5) having been in contact with each other (including transition metal complex (1) and transition metal complex (5) having been simultaneously produced) may be supplied; transition metal complex (1) and an activating co-catalyst component having been in contact with each other may be supplied; or transition metal complex (5) and an activating co-catalyst component having been in contact with each other may be supplied.

(Carrier)

Examples of the inorganic substance to be used in a carrier include inorganic oxides, magnesium compounds and so on. Clay, clay mineral, etc. can be used as well. These may be used as a mixture.

Specific examples of the inorganic oxide to be used in a carrier include $SiO_2$, $Al_2O_3$, $MgO$, $ZrO_2$, $TiO_2$, $B_2O_3$, $CaO$, $ZnO$, $BaO$, $ThO_2$ and mixtures of these such as $SiO_2$—$MgO$, $SiO_2$—$Al_2O_3$, $SiO_2$—$TiO_2$, $SiO_2$—$V_2O_5$, $SiO_2$—$Cr_2O_3$ and $SiO_2$—$TiO_2$—$MgO$. Of these inorganic oxides, $SiO_2$ and $Al_2O_3$ are preferable and $SiO_2$ is more preferable. The aforementioned inorganic oxide may contain a small amount of carbonate, sulfate, nitrate oxide component such as $Na_2CO_3$, $K_2CO_3$, $CaCO_3$, $MgCO_3$, $Na_2SO_4$, $Al_2(SO_4)_3$, $BaSO_4$, $KNO_3$, $Mg(NO_3)_2$, $Al(NO_3)_3$, $Na_2O$, $K_2O$ and $Li_2O$.

Furthermore, while a hydroxy group is usually produced and present on the surface of an inorganic oxide, active hydrogen of the hydroxy group on the surface can be substituted with various substituents to form a modified inorganic oxide, which can be used as the inorganic oxide. As the substituent, a silyl group is preferable. Specific examples of the modified inorganic oxide include inorganic oxides that have been brought into contact with a trialkylchlorosilane such as trimethylchlorosilane and tert-butyldimethylchlorosilane; a triarylchlorosilane such as triphenylchlorosilane; a dialkyldichlorosilane such as dimethyldichlorosilane; a diaryldichlorosilane such as diphenyl dichlorosilane; an alkyltrichlorosilane such as methyltrichlorosilane; an aryltrichlorosilane such as phenyltrichlorosilane; a trialkylalkoxysilane such as trimethylmethoxysilane; a triarylalkoxysilane such as triphenylmethoxysilane; a dialkyldialkoxysilane such as dimethyl dimethoxysilane; a diaryldialkoxysilane such as diphenyldimethoxysilane; an alkyltrialkoxysilane such as methyltrimethoxysilane; an aryltrialkoxysilane such as phenyltrimethoxysilane; a tetraalkoxysilane such as tetramethoxysilane; an alkyldisilazane such as 1,1,1,3,3,3-hexamethyldisilazane and tetrachlorosilane.

Examples of the magnesium compound to be used in a carrier include a magnesium halide such as magnesium chloride, magnesium bromide, magnesium iodide and magnesium fluoride; an alkoxymagnesium halide such as magnesium methoxychloride, magnesium ethoxychloride, magnesium isopropoxychloride, magnesium butoxychloride and magnesium octoxychloride; an allyloxymagnesium halide such as magnesium phenoxychloride and magnesium methylphenoxychloride; an alkoxy magnesium such as ethoxy magnesium, isopropoxy magnesium, butoxy magnesium, n-octoxy magnesium and 2-ethylhexoxy magnesium; an allyloxy magnesium such as phenoxy magnesium and dimethylphenoxy magnesium; and a magnesium carboxylate such as magnesium laurate and magnesium stearate. Of these, a preferable magnesium compound is magnesium halide or alkoxy magnesium and a further preferable magnesium compound is magnesium chloride or butoxy magnesium.

Examples of the clay or clay mineral to be used in a carrier include kaolin, bentonite, kibushi clay, gaerome clay, allophane, hisingerite, pyrophyllite, talc, mica, montmorillonite, vermiculite, chlorite, palygorskite, kaolinite, nacrite, dickite and halloysite. Of these, preferable clay or clay mineral include smectite, montmorillonite, hectorite, Laponite or saponite, further preferably montmorillonite or hectorite.

As the inorganic substance to be used in a carrier, an inorganic oxide is preferable.

As these inorganic substances to be used in a carrier, those dried by a heat treatment are preferably used. The temperature of the heat treatment is usually 100 to 1500° C., preferably 100 to 1000° C. and further preferably 200 to 800° C. The time for the heat treatment is not particularly limited; however, it is preferably 10 minutes to 50 hours, and more preferably 1 hour to 30 hours. As a heat treatment method, a method of heating an inorganic substance and then passing a dried inert gas (for example, nitrogen or argon) at a predetermined flow rate for several hours or more or then reducing pressure for several hours is mentioned. However, the heat treatment method is not limited.

An average particle size of a carrier formed of an inorganic substance is preferably 5 to 1000 μm, more preferably 10 to 500 μm and further preferably 10 to 100 μm. The pore volume of a carrier formed of an inorganic substance is preferably 0.1 ml/g or more and more preferably 0.3 to 10 ml/g. The specific surface area of a carrier formed of an inorganic substance is preferably 10 to 1000 m²/g and more preferably 100 to 500 m²/g.

The organic polymer to be used in a carrier is not particularly limited and two or more organic polymers may be used as a mixture. A polymer having a group having an active hydrogen and/or a non-proton donating Lewis basic group is preferable.

A group having an active hydrogen is not particularly limited as long as it has an active hydrogen. Specific examples thereof include a primary amino group, a secondary amino group, an imino group, an amide group, a hydrazide group, an amidino group, hydroxy group, a hydroperoxy group, carboxyl group, a formyl group, a carbamoyl group, a sulfonic acid group, a sulfinic acid group, a sulfenic acid group, a thiol group, a thioformyl group, a pyrrolyl group, an imidazolyl group, a piperidyl group, an indazolyl group and a carbazolyl group. A preferable group is a primary amino group, a secondary amino group, an imino group, an amide group, an imide group, hydroxy group, a formyl group, carboxyl group, a sulfonic acid group or a thiol group. Particularly preferable group is a primary amino group, a secondary amino group, an amide group or hydroxy group. It should be noted that these groups may be substituted with a halogen atom or a hydrocarbyl group having 1 to 20 carbon atoms.

A non-proton donating Lewis basic group is not particularly limited as long as it has a group having a Lewis base moiety having no active hydrogen atom. Specific examples thereof include a pyridyl group, an N-substituted imidazolyl group, an N-substituted indazolyl group, a nitrile group, an azide group, an N-substituted imino group, an N,N-substituted amino group, an N,N-substituted aminooxy group, an N,N,N-substituted hydrazino group, a nitroso group, a nitro group, a nitrooxy group, a furyl group, a carbonyl group, a thiocarbonyl group, an alkoxy group, an alkyloxycarbonyl group, an N,N-substituted carbamoyl group, a thioalkoxy group, a substituted sulfinyl group, a substituted sulfonyl group and a substituted sulfonic acid group. The non-proton donating Lewis basic group is preferably a heterocyclic group, further preferably, an aromatic heterocyclic group having an oxygen atom and/or a nitrogen atom within the ring, particularly preferably, a pyridyl group, an N-substituted imidazolyl group or a N-substituted indazolyl group and most preferably a pyridyl group. It should be noted that these groups may be substituted with a halogen atom or a hydrocarbyl group having 1 to 20 carbon atoms.

The amount of the groups having an active hydrogen and the non-proton donating Lewis basic groups in a polymer, more specifically, the molar amount of the groups per unit gram of the polymer is preferably 0.01 to 50 mmol/g and more preferably 0.1 to 20 mmol/g.

The polymer having such a group can be obtained by homo-polymerizing, for example, a monomer having a group having an active hydrogen and/or a non-proton donating Lewis basic group and one or more polymerizable unsaturated group or by copolymerizing this monomer with an additional monomer(s) having one or more polymerizable unsaturated groups. Furthermore, as at least one of the additional monomers, a crosslinking polymerizable monomer having two or more polymerizable unsaturated groups is preferably used.

As the monomer having a group having an active hydrogen and/or a non-proton donating Lewis basic group and one or more polymerizable unsaturated groups, the aforementioned monomer having a group having an active hydrogen and one or more polymerizable unsaturated groups and the aforementioned monomer having a group having a Lewis base moiety having no active hydrogen atom and one or more polymerizable unsaturated groups can be mentioned. Examples of the polymerizable unsaturated group include an alkenyl group such as vinyl group and allyl group; and an alkynyl group such as ethyne group.

Examples of the monomer having a group having an active hydrogen and one or more polymerizable unsaturated groups include a vinyl group-containing primary amine, a vinyl group-containing secondary amine, a vinyl group-containing amide compound and a vinyl group-containing hydroxy compound. Specific examples thereof include N-(1-ethenyl)amine, N-(2-propenyl)amine, N-(1-ethenyl)-N-methylamine, N-(2-propenyl)-N-methylamine, 1-ethenylamide, 2-propenylamide, N-methyl-(1-ethenyl)amide, N-methyl-(2-propenyl)amide, vinyl alcohol, 2-propen-1-ol and 3-buten-1-ol.

Specific examples of the monomer having a non-proton donating Lewis basic group and one or more polymerizable unsaturated groups include vinyl pyridine, vinyl(N-substituted)imidazole and vinyl(N-substituted)indazole.

As the additional monomers having one or more polymerizable unsaturated groups, e.g., an olefin and an aromatic vinyl compound are exemplified. Specific examples thereof include ethylene, propylene, 1-butene, 1-hexene, 4-methyl-1-pentene and styrene. Preferable monomer is ethylene or styrene. These monomers may be used in combination of two or more species. Furthermore, specific examples of the crosslinking polymerizable monomer having two or more polymerizable unsaturated groups include divinylbenzene.

An average particle size of the carrier formed of an organic polymer is preferably 5 to 1000 μm, and more preferably 10 to 500 μm. The pore volume of the carrier formed of an organic polymer is preferably 0.1 ml/g or more and more preferably 0.3 to 10 ml/g. The specific surface area of the carrier formed of an organic polymer is preferably 10 to 1000 $m^2/g$ and more preferably 50 to 500 $m^2/g$.

As the organic polymer to be used in a carrier, those dried by a heat treatment are preferably used. The temperature of the heat treatment is usually 30 to 400° C., preferably 50 to 200° C. and further preferably 70 to 150° C. The time for the heat treatment is not particularly limited; however, it is preferably 10 minutes to 50 hours, more preferably 1 hour to 30 hours. As the heat treatment method, a method of heating an organic polymer and then passing a dried inert gas (for example, nitrogen or argon) at a predetermined flow rate for several hours or more or then reducing the pressure for several hours is mentioned. However, the heating treatment method is not limited.

Geometric standard deviation of the particle size of the carrier in terms of volume is preferably 2.5 or less, more preferably 2.0 or less and further preferably 1.7 or less.

<Polymerization>

The present invention relates to a method for producing an ethylenic polymer by polymerizing ethylene in the presence of the aforementioned catalyst for olefin polymerization.

Polymerization may be performed by supplying only ethylene as the raw-material monomer or supplying a monomer copolymerizable with ethylene and ethylene.

Examples of the monomer copolymerizable with ethylene include an olefin having 3 to 20 carbon atoms such as propylene, 1-butene, 1-pentene, 1-hexene, 1-heptene, 1-octene, 1-nonene, 1-decene, 1-dodecene, 4-methyl-1-pentene and 4-methyl-1-hexene; a cyclic olefin such as norbornene; an alkenyl aromatic hydrocarbyl such as styrene; an unsaturated carboxylic acid such as acrylic acid and methacrylic acid; an unsaturated carboxylic acid ester such as methyl acrylate, ethyl acrylate, butyl acrylate, methyl methacrylate and ethyl methacrylate; and a vinyl ester compound such as vinyl acetate. These may be used solely or in combination of two or more.

The polymerization method is not particularly limited; however, for example, solvent polymerization using an aliphatic hydrocarbyl such as butane, pentane, hexane, heptane and octane, an aromatic hydrocarbyl such as benzene and toluene or a hydrocarbyl halide such as methylene dichloride as a solvent, slurry polymerization, or vapor-phase polymerization performed in a gaseous monomer can be employed. Furthermore, it can be a continuous polymerization or batch-polymerization.

In the cases of solution polymerization and slurry polymerization, the concentration of the catalyst for olefin polymerization in the polymerization solution is usually 0.0001 to 5 mmol/liter in terms of the mole equivalent of the transition metal complexes (total of transition metal complex (1) and transition metal complex (5)) serving as the catalytic component. The concentration of a catalyst for olefin polymerization for improving economic potential is preferably 2 mmol/liter or less and more preferably 1 mmol/liter or less. Furthermore, the concentration of a catalyst for olefin polymerization for improving the number of long chain branches is preferably 0.001 mmol/liter or more, more preferably 0.01 mmol/liter or more, further preferably 0.1 mmol/liter or more and particularly preferably 0.5 mmol/liter or more.

The polymerization pressure is preferably from normal pressure to 5 MPa. The polymerization time is generally appropriately determined depending upon the desired polymer type and the reactor; however, it can fall within the range of 1 minute to 20 hours. Furthermore, a chain transfer agent such as hydrogen can be added in order to control the molecular weight of the ethylenic polymer.

The polymerization temperature in producing the ethylenic polymer of the present invention is usually 0 to 220° C. The polymerization temperature for obtaining high polymerization activity is preferably 20° C. or more, more preferably 40° C. or more and particularly preferably 70° C. or more. Furthermore, the polymerization temperature for improving stability of a catalyst is preferably 130° C. or less and more preferably 100° C. or less.

EXAMPLES

The present invention will be explained by way of the following Examples and Comparative Examples.

<Production of Transition Metal Complex>

The physical properties were measured by the following methods.

(1) Proton Nuclear Magnetic Resonance Spectrum ($^1$H-NMR)

Apparatus: EX270 manufactured by JEOL Ltd.
Sample cell: Tube of 5 mm in diameter
Measurement solvent: $CDCl_3$
Sample concentration: 10 mg/0.5 mL ($CDCl_3$)
Measurement temperature: Room temperature (about 25° C.)
Measurement parameter: Probe of 5 mm in diameter, EXMOD NON, OBNUC $^1$H, accumulation number: 64
Repeat time: ACQTM 6 seconds, PD 1 second
Internal standard: $CDCl_3$ (7.26 ppm)

(2) Carbon Nuclear Magnetic Resonance Spectrum ($^{13}$C-NMR)

Apparatus: EX270 manufactured by JEOL Ltd.
Sample cell: Tube of 5 mm in diameter
Measurement solvent: $CDCl_3$
Sample concentration: 30 mg/0.5 mL ($CDCl_3$)
Measurement temperature: Room temperature (about 25° C.)
Measurement parameter: Probe of 5 mm in diameter, EXMOD BCM, OBNUC $^{13}$C, accumulation number: 2560
Repeat time: ACQTM 1.79 seconds, PD 1.21 seconds
Internal standard: $CDCl_3$ (77 ppm)

(3) Mass Spectrum
[Electron Ionization Mass Spectrometry (EI-MS)]
Apparatus: JMS-T100GC manufactured by JEOL Ltd.
Ionization voltage: 70 eV
Ion source temperature: 230° C.
Acceleration voltage: 7 kV
MASS RANGE: m/z 35-800

Reference Example 1

Synthesis of [1-n-butylmethylphenylsilyl-2,3,4,5-tetramethylcyclopentadienyl]titanium trichloride (Hereinafter, Referred to as "Complex 1")

Synthesis of 1-n-butylmethylphenylsilyl-2,3,4,5-tetramethylcyclopentadiene

After sodium hydride dispersed in mineral oil (0.80 g, 33.47 mmol as sodium hydride) was washed with hexane to remove the mineral oil under nitrogen atmosphere, tetrahydrofuran (38 mL) was added. The temperature of the mixture was elevated to 50° C. and aniline (0.21 g, 2.23 mmol) was added. The mixture was stirred at 50° C. for 1 hour. To the resultant mixture, a solution obtained by dissolving 1,2,3,4-tetramethylcyclopenta-1,3-diene (3.00 g, 24.55 mmol) in tetrahydrofuran (10 mL) was added dropwise and stirred at 50° C. for 2 hours. The solution was cooled to 0° C. To the solution, a solution obtained by dissolving chloro(n-butyl)methylphenyl silane (4.75 g, 22.32 mmol) in toluene (10 mL) was added dropwise and stirred at 35° C. for 2 hours. The resultant mixture was added dropwise to a mixed solution of a 10% sodium hydrogen carbonate solution (24 mL) and a 10% sodium carbonate solution (24 mL) at 0° C. Toluene (24 mL) was added to separate an organic phase. The organic phase was washed with water (40 nit) and further washed with a saturated brine (20 mL). The organic phase was dried over sodium sulfate and then filtrated. The solvent was concentrated under reduced pressure to obtain 1-n-butylmethylphenylsilyl-2,3,4,5-tetramethylcyclopentadiene (5.16 g, yield 77.4%).

$^1$H-NMR (CDCl$_3$, δ ppm): 0.13 (s, 3H), 0.66-0.90 (m, 214), 0.84 (t, J=7.0 Hz, 3H), 1.15-1.35 (m, 4H), 1.67 (s, 3H), 1.71 (s, 3H), 1.73 (s, 3H), 1.80 (s, 3H), 3.10 (s, 1H), 7.29-7.36 (m, 3H), 7.41-7.47 (m, 2H)

Mass Spec (EI-MS, m/z): 298 (M$^+$)

Synthesis of Complex 1

Under nitrogen atmosphere, to a toluene solution (23 mL) of 1-n-butylmethylphenylsilyl-2,3,4,5-tetramethylcyclopentadiene (2.30 g, 7.70 mmol) and triethylamine (1.95 g, 19.25 mmol), a 1.55 M hexane solution (6.21 mL, 9.63 mmol) of n-butyllithium was added dropwise at −78° C. After the temperature of the mixture was gradually elevated to room temperature, the mixture was stirred at 35° C. for 2.5 hours. The resultant mixture was cooled to −78° C., a solution obtained by dissolving titanium tetrachloride (2.19 g, 11.55 mmol) in toluene (12 mL) was added dropwise at the same temperature. The temperature or the mixture was elevated again to an interior temperature of 60° C. and stirred at the same temperature for 2 hours. After the reaction, the solvent was concentrated under reduced pressure. To the residue, heptane was added and filtrated to remove insoluble matter. The solvent was concentrated from the filtrate under reduced pressure. Pentane was added, precipitated white solid substance was removed by filtration, and the filtrate was cooled to −20° C. The resultant solid substance was filtrated, washed with a small amount of pentane, and dried under reduced pressure to obtain Complex 1 (0.25 g, yield 7.2%) as an orange solid substance.

$^1$H-NMR (CDCl$_3$, δ ppm): 0.76 (s, 3H), 0.87 (t, J=7.0 Hz, 3H), 1.23-1.42 (m, 6H), 2.27 (s, 3H), 2.28 (s, 3H), 2.36 (s, 3H), 2.46 (s, 3H), 7.30-7.42 (m, 3H), 7.43-7.52 (m, 2H)
$^{13}$C-NMR (CDCl$_3$, δ ppm): −2.61, 13.69, 14.13, 14.32, 14.90, 17.71, 25.86, 26.51, 128.01, 129.53, 134.45, 136.25, 139.44, 141.96, 142.47, 144.63, 144.92

Mass Spec (EI-MS, m/z): 393 (M$^+$-Bu)

Reference Example 2

Synthesis of Catalytic Component 1

Under nitrogen, 2-allyloxy-1-bromo-3-tert-butyl-5-methyl benzene (25.00 g, 88.28 mmol) was dissolved in toluene (289 mL). After the solution was cooled to −78° C., a 1.58 M hexane solution (72.63 mL, 114.76 mmol) of n-butyllithium was added dropwise. The temperature of the mixture was gradually elevated to −15° C. After stirred at −15° C. for 1.5 hours, the mixture was cooled to −78° C. Dichloromethylphenylsilane (50.62 g, 264.83 mmol) was added in one stroke, and the temperature of the mixture was gradually elevated to room temperature. After the mixture was stirred at 50° C. for 1 hour, the solvent was concentrated under reduced pressure. Hexane was added and then insoluble matter was removed by Celite filtration. The solvent was concentrated under reduced pressure and further concentrated at 70° C. for 3 hours under reduced pressure to obtain residue A (29.29 g).

THF (43 mL) was added to sodium hydride (60 wt %, 0.89 g, 22.32 mmol) under nitrogen. The temperature of the THF slurry of sodium hydride was elevated to 50° C. Aniline (0.14 g, 1.49 mmol) was added and the mixture was stirred at 50° C. for further 1 hour. A solution obtained by dissolving 1,2,3,4-tetramethyl-1,3-cyclopentadiene (2.00 g, 16.37 mmol) in THF (11 mL) was slowly added dropwise. After the completion of the dropwise addition, the mixture was stirred at 50° C. for further 2 hours until the generation of hydrogen gas was terminated. After the mixture was cooled to 20° C., a solution obtained by dissolving residue A (6.91 g) in toluene (11 mL) was added dropwise. The mixture was continuously stirred at room temperature for 3 hours. The resultant reacted solution was added dropwise to a solution mixture of a 10% aqueous sodium hydrogen carbonate solution (27 mL) and a 10% aqueous sodium carbonate solution (27 mL) cooled to 0° C. to terminate the reaction. Toluene (27 mL) was added and phases were separated. After the reacted solution was dried over sodium sulfate, the solvent was concentrated under reduced pressure to obtain residue B (9.80 g).

Under nitrogen, to a toluene solution (104 mL) of residue B (9.79 g) and triethylamine (6.78 g, 66.99 mmol), a 1.60 M hexane solution (20.93 mL, 33.49 mmol) of n-butyllithium was added dropwise at −78° C. After the temperature of the mixture was gradually elevated to room temperature, the mixture was stirred at room temperature for 3 hours. To the resultant mixture, a solution obtained by dissolving titanium tetrachloride (4.24 g, 22.33 mmol) in toluene (22 mL) was added dropwise, and the temperature of the mixture was gradually elevated to room temperature. After the temperature was elevated to 90° C., the mixture was stirred at 90° C. for 2 hours. After the solvent was concentrated under reduced pressure, hot heptane was added. The mixture was filtrated to remove insoluble matter and the solvent was concentrated under reduced pressure. Pentane was added and the precipitated solid substance was filtrated to obtain a catalytic component (hereinafter, referred to as "catalytic component 1") (1.29 g). The catalytic component was mostly methylphenylsilylene-(tetramethylcyclopentadienyl)(3-tert-butyl-5-methyl-2-phenoxy)titanium dichloride, wherein 2 mol % of Complex 1 was contained (calculated from an integral value of 0.76 ppm).

Reference Example 3

Synthesis of dimethylsilylene(tetramethylcyclopentadienyl)(3-tert-butyl-5-methyl-2-phenoxy)titanium dichloride (hereinafter, referred to as "complex 2")

Complex 2 was produced in accordance with the method described in Example 53 of JP 9-87313 A.

Reference Example 4

Synthesis of [1-dimethyl(4-methoxyphenyl)silyl-2,3,4,5-tetramethylcyclopentadienyl]titanium trichloride (hereinafter, referred to as "Complex 3")

Synthesis of 1-dimethyl(4-methoxyphenyl)silyl-2,3,4,5-tetramethylcyclopentadiene Under nitrogen atmosphere, sodium hydride dispersed in mineral oil (0.96 g, 40.00 mmol as sodium hydride) was washed with hexane to remove the mineral oil, and thereafter tetrahydrofuran (43 mL) was added. The temperature of the mixture was elevated to 50° C. and aniline (0.25 g, 2.67 mmol) was added. The mixture was stirred at 50° C. for 2 hours and a half. A solution obtained by dissolving 1,2,3,4-tetramethylcyclopenta-1,3-diene (3.42 g, 28.00 mmol) in tetrahydrofuran (11 mL) was added dropwise to this. The mixture was stirred at 50° C. for 2 hours and a half and cooled to 0° C. To the solution, a solution obtained by dissolving chlorodimethyl(4-methoxyphenyl)silane (5.35 g, 26.67 mmol) in toluene (11 mL) was added dropwise. The mixture was stirred at room temperature overnight. The resultant mixture was added dropwise to a 10% aqueous sodium carbonate solution (56 ml) at 0° C. Toluene (80 ml) was added to separate an organic phase. The organic phase was washed twice with water (80 ml) and further washed with saturated brine (50 ml). The organic phase was dried over sodium sulfate and filtrated, and then the solvent was concentrated under reduced pressure to obtain 1-dimethyl(4-methoxyphenyl)silyl-2,3,4,5-tetramethylcyclopentadiene (7.30 g, yield 95.5%).

$^1$H-NMR (CDCl$_3$, δ ppm): 0.18 (s, 6H), 1.75 (s, 6H), 1.77 (s, 6H), 3.06 (s, 1H), 3.83 (s, 3H), 6.90 (d, J=8.6 Hz, 7.39 (d, J=8.7 Hz, 2H)

Mass Spec (EI-MS, m/z): 286 (M$^+$)

Synthesis of Complex 3

Under nitrogen atmosphere, to a toluene solution (48 ml) of 1-dimethyl(4-methoxyphenyl)silyl-2,3,4,5-tetramethylcyclopentadiene (2.01 g, 7.00 mmol) and triethylamine (3.54 g, 35.00 mmol), a 1.65 M hexane solution (5.09 ml, 8.40 mmol) of n-butyllithium was added dropwise at −78° C. After the temperature was gradually elevated to room temperature, the mixture was stirred at room temperature for 2 hours. The resultant mixture was cooled to −78° C. and a solution obtained by dissolving titanium tetrachloride (1.46 g, 7.70 mmol) in toluene (8 ml) was added dropwise at the same temperature. After the temperature was gradually elevated to room temperature, the mixture was stirred at room temperature overnight. After the reaction, the solvent was concentrated under reduced pressure, and heptane was added to the residue and filtrated to remove insoluble matter. The solvent was concentrated from the filtrate under reduced pressure. Pentane was added, and the resultant solid substance was filtrated, washed with a small amount of pentane and dried under reduced pressure to obtain complex 3 (0.48 g, yield 15.6%) as an orange solid substance.

$^1$H-NMR (CDCl$_3$, δ ppm): 0.73 (s, 6H), 2.32 (s, 6H), 2.39 (s, 6H), 3.81 (s, 3H), 6.90 (d, J=8.7 Hz, 2H), 7.39 (d, J=8.7 Hz, 2H)

$^{13}$C-NMR (CDCl$_3$, δ ppm): 0.50, 14.35, 17.81, 55.20, 114.00, 128.16, 135.71, 139.59, 142.33, 145.04, 160.98

Mass Spec (EI-MS, m/z): 438 (M$^+$)

Reference Example 5

Synthesis of [1-triphenylsilyl-2,3,4,5-tetramethylcyclopentadienyl]titanium trichloride (Hereinafter, Referred to as "Complex 4")

Synthesis of 1-triphenylsilyl-2,3,4,5-tetramethylcyclopentadiene

Under nitrogen atmosphere, sodium hydride dispersed in mineral oil (0.54 g, 22.32 mmol as sodium hydride) was washed with hexane to remove mineral oil, and thereafter tetrahydrofuran (35 ml) was added. The temperature of the mixture was elevated to 50° C. and aniline (0.14 g, 1.49 mmol) was added. The mixture was stirred at 50° C. for 1 hour. A solution obtained by dissolving 1,2,3,4-tetramethylcyclopenta-1,3-diene (2.00 g, 16.37 mmol) in tetrahydrofuran (9 ml) was added dropwise to this, and the mixture was stirred at 50° C. for 2 hours and cooled to 20° C. To the solution, a solution obtained by dissolving chlorotriphenylsilane (4.39 g, 14.88 mmol) in toluene (9 ml) was added dropwise, and the mixture was stirred at 35° C. overnight. The resultant mixture was added dropwise at 0° C. to a mixture of a 10% sodium hydrogen carbonate solution (22 ml) and a 10% sodium carbonate solution (22 ml). Toluene (22 ml) was added to separate an organic phase. The organic phase was dried over sodium sulfate and filtrated, and the solvent was concentrated under reduced pressure to obtain 1-triphenylsilyl-2,3,4,5-tetramethylcyclopentadiene (3.76 g, yield 66.3%).

$^1$H-NMR (CDCl$_3$, δ ppm): 1.55 (s, 6H), 1.57 (s, 6H), 3.77 (s, 1H), 7.27-7.42 (m, 9H), 7.54-7.63 (m, 6H)

Mass Spec (EI-MS, m/z): 380 (M$^+$)

Synthesis of Complex 4

Under nitrogen atmosphere, to a toluene solution (28 ml) of 1-triphenylsilyl-2,3,4,5-tetramethylcyclopentadiene (1.42 g, 4.45 mmol) and triethylamine (2.25 g, 22.24 mmol), a 1.55 M hexane solution (3.44 ml, 5.34 mmol) of n-butyllithium was added dropwise at −78° C. After the temperature was gradually elevated to room temperature, the mixture was stirred at 35° C. for 3 hours. The resultant mixture was cooled to −78° C. and a solution of titanium tetrachloride (0.93 g, 4.89 mmol) dissolved in toluene (5 ml) was added dropwise at the same temperature. The temperature was elevated again to obtain an interior temperature of 35° C., and the mixture was stirred at the same temperature for 1 hour. After the reaction, the solvent was concentrated under reduced pressure. Heptane was added to the residue and filtrated to remove insoluble matter. The solvent was concentrated from a filtrate under reduced pressure. Pentane was added, and the resultant solid substance was filtrated, washed with a small amount of pentane and dried under reduced pressure to obtain complex 4 (0.07 g, yield 3.1%) as an orange solid substance. Furthermore, to the aforementioned insoluble matter removed by adding heptane, toluene was added and filtrated to further remove toluene-insoluble matter. The solvent was concentrated under reduced pressure from the filtrate. Pentane was added to the mixture and the resultant solid substance was filtrated, washed with a small amount of pentane, and dried under reduced pressure to obtain complex 4 (0.34 g, yield 14.5%) as an orange solid substance.

$^1$H-NMR (CDCl$_3$, δ ppm): 2.05 (s, 6H), 2.36 (s, 6H), 7.32-7.49 (m, 9H), 7.59-7.65 (m, 6H)

$^{13}$C-NMR (CDCl$_3$, δ ppm): 14.48, 17.76, 127.96, 130.07, 132.99, 136.93, 142.35, 146.04

Mass Spec (EI-MS, m/z): 532 (M$^+$)

Production of Ethylenic Polymer

Measured values of the physical properties in Examples and Comparative Examples were obtained by the following methods. To the measurement samples, an appropriate amount (for example 1000 ppm) of antioxidant was added in advance, as necessary.

(4) Intrinsic Viscosity ([η], unit: dl/g)

A tetralin solution of 2,6-di-t-butyl-p-cresol (BHT) dissolved in a concentration of 0.5 g/L (hereinafter, referred to as "blank solution") and a solution of the ethylenic polymer dissolved in the blank solution at a concentration of 1 mg/ml (hereinafter, referred to as "sample solution") were prepared. The fall times of the blank solution and the sample solution at 135° C. were measured with a Ubbelohde viscometer. After relative viscosity (ηrel) at 135° C. was determined from the fall time, intrinsic viscosity [η] was calculated in accordance with the following formula.

$$\eta = 23.3 \times \log(\eta rel)$$

(5) Flow Activation Energy (Ea) (Unit: kJ/mol)

Using a viscoelasticity measurement apparatus (for example, Rheometrics Mechanical Spectrometer RMS-800 manufactured by Rheometrics), three or more melt complex viscosity-angular frequency curves of the polymer were measured at 130° C., 150° C., 170° C., 190° C., 210° C. and 230° C. under the following measurement conditions. Then, from the obtained melt complex viscosity-angular frequency curves, a master curve of a melt complex viscosity-angular frequency curve at 190° C. was drawn using a computational software Rhios V.4.4.4 produced by Rheometrics to determine the activation energy (Ea).

(Measurement Conditions)
Geometry: Parallel plate
Plate diameter: 25 mm
Plate spacing: 1.5 to 2 mm
Strain: 5%
Angular frequency: 0.1 to 100 rad/second
Measurement atmosphere: Nitrogen (6) Molecular Weight Distribution (Mw/Mn, Mz/Mw)

Using gel permeation chromatography (GPC), the z-average molecular weight (Mz), the weight-average molecular weight (Mw) and the number average molecular weight (Mn) of the polymer were determined under the following conditions (1) to (8) to obtain Mw/Mn and Mz/Mw.
(1) Apparatus: Waters 150C manufactured by Waters
(2) Separation column: TOSOH TSK gel GMH6-HT, 2 columns
(3) Measurement temperature: 140° C.
(4) Carrier: Orthodichlorobenzene
(5) Flow rate: 1.0 mL/minute
(6) Injection volume: 500 µL
(7) Detector: Differential refractometer
(8) Molecular weight reference material: standard polystyrene (7) Measurement of Storage Modulus (G') and Loss Modulus (G")

Using a viscoelasticity measurement apparatus (for example, Rheometrics Mechanical Spectrometer RMS-800 manufactured by Rheometrics), a storage modulus (G')-angular frequency curve and a loss modulus (G")-angular frequency curve were measured at 190° C. under the following measurement conditions. Based on values of the storage modulus (G') and the loss modulus (G") measured at the angular frequency of 0.1 rad/second, the value (G'/G") was determined.

<Measurement Conditions>
Geometry: Parallel plate
Plate diameter: 25 mm
Plate spacing: 1.5 to 2 mm
Strain: 5%
Angular frequency: 0.1 to 100 rad/second
Measurement atmosphere: Nitrogen (8) Ratio of Storage Modulus (G') to Loss Modulus (G"), (G'/G")

The value of (G'/G") was calculated from the values of the storage modulus (G') and the loss modulus (G") at the angular frequency of 0.1 rad/second at 190° C. in the storage modulus (G')-angular frequency curve and the loss modulus (G")-angular frequency curve measured under the aforementioned measurement conditions.

(9) Measurement of Storage Modulus (G')

In the storage modulus (G')-angular frequency curve measured under the aforementioned measurement conditions, the storage modulus (G') at 190° C. and at the angular frequency of 0.1 rad/second was determined.

(10) The Relationship Between Storage Modulus (G') and Loss Modulus (G") in the Angular Frequency Range of 0.1 to 10000 at 190° C.

Using a viscoelasticity measurement apparatus (for example, Rheometrics Mechanical Spectrometer RMS-800 manufactured by Rheometrics) three or more melt complex viscosity-angular frequency curves of the polymer at 130° C., 150° C., 170° C., 190° C., 210° C. and 230° C. were measured under the following measurement conditions. Then, from the melt complex viscosity-angular frequency curves thus obtained, master curves of the storage modulus (G')-angular frequency curve and the storage modulus (G")-angular frequency curve at 190° C. were prepared by using computational software Rhios V.4.4.4 produced by Rheometrics. Then, the relationship between the storage modulus (G') and the loss modulus (G") in the angular frequency range of from 0.1 to 10000 at 190° C. and the angular frequency at which the storage modulus (G') is crossed with the loss modulus (G") (hereinafter, also referred to as "$\omega_x$") were obtained.

<Measurement Conditions>
Geometry: Parallel plate
Plate diameter: 25 mm
Plate spacing: 1.5 to 2 mm
Strain: 5%
Angular frequency: 0.1 to 100 rad/second
Measurement atmosphere: Nitrogen

(11) Characteristic Relaxation Time ($\tau$, Unit: Seconds)

Using a viscoelasticity measurement apparatus (for example, Rheometrics Mechanical Spectrometer RMS-800, manufactured by Rheometrics), three or more melt complex viscosity-angular frequency curves of the polymer were measured at 130° C., 150° C., 170° C., 190° C., 210° C. and 230° C. under the following measurement conditions. Then, from the melt complex viscosity-angular frequency curves thus obtained, a master curve of the melt complex viscosity-angular frequency curve at 190° C. was drawn using a computational software Rhios V.4.4.4 produced by Rheometrics to determine the activation energy (Ea).

(Measurement Conditions)
Geometry: Parallel plate
Plate diameter: 25 mm
Plate spacing: 1.5 to 2 mm
Strain: 5%
Angular frequency: 0.1 to 100 rad/second
Measurement atmosphere: Nitrogen

(12) Preparation of Blended Material

A linear polyethylene, Sumikathene L, FS 150 (manufactured by Sumitomo Chemical Co., Ltd.), (4.75 g) and the ethylenic polymer (0.25 g) were dissolved in 100 ml of xylene (140° C.) to which an antioxidant (BHT) was added in an amount of 1000 ppm based on the total amount of the resins and reprecipitated with ethanol to prepare a blended material.

(13) Measurement of Elongational Viscosity Nonlinear Index ($\lambda$) of Blended Material The elongational viscosity nonlinear index ($\lambda$) is a maximum $\lambda(t)$ value obtained in the following equation:

$$\lambda(t) = \sigma_1(t)/\sigma_{0.1}(t).$$

which was obtained by dividing viscosity-time curve $\sigma_1(t)$ of the molten resin when the resin was uniaxially stretched at the strain rate of 1 s$^{-1}$ in terms of Hencky strain at the temperature of 150° C. obtained by using an elongational viscosity measurement apparatus (for example, ARES, manufactured by TA Instruments) by viscosity-time curve $\sigma_{0.1}(t)$ of the molten resin when the resin was uniaxially stretched at the strain rate of 0.1 s$^{-1}$ in terms of Hencky strain at the temperature of 150° C.

It should be noted that, as the measurement test piece, a sheet having the size of 18 mm×10 mm and the thickness 0.7 mm obtained by press molding was used.

(14) Melt Complex Viscosity ($\eta^*$, unit: Pa·sec)

Using a viscoelasticity measurement apparatus (for example, Rheometrics Mechanical Spectrometer RMS-800 manufactured by Rheometrics), a melt complex viscosity-angular frequency curve at 190° C. was measured under the following measurement conditions and the melt complex viscosity at the angular frequency of 100 rad/second was determined. The lower the melt complex viscosity is, the more excellent the extrusion load during the extrusion molding is.

<Measurement Conditions>
Geometry: Parallel plate
Plate diameter: 25 mm
Plate spacing: 1.5 to 2 mm
Strain: 5%.
Angular frequency: 0.1 to 100 rad/second
Measurement atmosphere: Nitrogen

(15) Numbers of Each Alkyl Branches and Long Chain Branches Per 1000 Carbon Atoms A carbon nuclear magnetic resonance ($^{13}$C-NMR) spectrum of the polymer was measured by carbon nuclear magnetic resonance ($^{13}$C-NMR) method under the following measurement conditions and the numbers of each alkyl branches and long chain branches per 1000 carbon atoms in the polymer were determined in accordance with the following calculation method.

(Measurement Conditions)
Apparatus: AVANCE 600 manufactured by Bruker Corporation
Measurement probe: 10 mm CryoProbe
Measurement solvent: Liquid mixture of 1,2-dichlorobenzene/1,2-dichlorobenzene-d4=75/25 (volume ratio)
Measurement temperature: 130° C.
Measurement method: Proton decoupling method
Pulse width: 45 degrees
Pulse repeat duration: 4 seconds
Measurement reference: tetramethylsilane
Window function: Exponential or Gaussian
Accumulation number: 2500

(Method for Calculating the Number of Methyl Branches)
In an NMR spectrum processed with an exponential window function, the peak area of the peak having the peak top thereof at 19 to 20 ppm normalized assuming that the sum total of the peak areas of all the peaks having the peak tops thereof in 5 to 50 ppm was 1000 was determined as the number of methyl branches.

(Method for Calculating the Number of Ethyl Branches)
In an NMR spectrum processed with an exponential window function, the peak area of the peak having the peak top thereof at 39.5 to 40.0 ppm normalized assuming that the sum total of the peak areas of all the peaks having the peak tops thereof in 5 to 50 ppm was 1000 was determined as the number of ethyl branches.

(Method for Calculating the Number of Propyl Branches)
In an NMR spectrum processed with an exponential window function, the peak area of the peak having the peak top thereof at 14.3 to 14.8 ppm normalized assuming that the sum total of the peak areas of all the peaks having the peak tops thereof in 5 to 50 ppm was 1000 was determined as the number of propyl branches.

(Method for Calculating the Number of the Branches Having 4 or More Carbon Atoms)
In an NMR spectrum processed with an exponential window function, the sum total of the peak areas of the peaks having the peak tops thereof in 38.0 to 38.5 ppm normalized assuming that the sum total of the peak areas of all the peaks having the peak tops thereof in 5 to 50 ppm was 1000 was determined as the number of the branches having 4 or more carbon atoms (Method for Calculating the Number of Amyl Branches)
In an NMR spectrum processed with an exponential window function, the peak area of the peak having the peak top thereof at 32.5 to 32.7 ppm normalized assuming that the sum total of the peak areas of all the peaks having the peak tops thereof in 5 to 50 ppm was 1000 was measured.

(Method for Calculating the Number of Hexyl Branches)
In an NMR spectrum processed with an exponential window function, the peak area of the peak derived from 3B6 carbons in hexyl branches (see the following formula (X)) normalized assuming that the sum total of the peak areas of all the peaks having the peak tops thereof in 5 to 50 ppm was 1000 was determined as the number of hexyl branches. When measuring an ethylene-1-octene copolymer in the present measurement conditions, since the peak derived from 3B6 carbon in the hexyl branches was observed at 32.16 ppm, the peak area of the peak having the peak top thereof in the range of 32.14 to 32.19 ppm was measured. Formula (X):

[Formula 6]

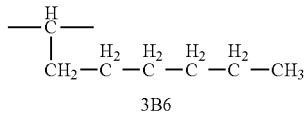

(Method for Calculating the Number of Branches Having 7 or More Carbon Atoms (Long Chain Branch (LCB))
In an NMR processed with a Gaussian window function, the number of long chain branches (the number of branches having 7 or more carbon atoms) was determined from the peak area of the peak derived from methine carbons to which a branch having 7 or more carbon atoms is bonded assuming that the sum total of the peak areas of all the peaks having the peak tops thereof in 5 to 50 ppm was 1000. In the measurement conditions, the number of long chain branches (the number of branches having 7 or more carbon atoms) was determined from the peak area of the peak having the peak top thereof around 38.22 to 38.27 ppm. The peak area of the peak is defined as the area of signals within the range from the chemical shift of the valley with the adjacent peak at the higher magnetic-field side to the chemical shift of the valley with the adjacent peak at the lower magnetic-field side. It should be noted that, when measuring an ethylene-1-octene copolymer in the present measurement conditions, the peak-top position of a peak derived from methine carbons to which a hexyl branch was bonded was 38.21 ppm.

(Method for Calculating the Number of Butyl Branches)
The number of butyl branches was determined as a value obtained by subtracting the number of amyl branches, the number of hexyl branches and the number of branches having 7 or more carbon atoms (the number of long chain branches) from the calculated number of branches having 4 or more carbon atoms.

(Method for Calculating the Number of Branches (Short-Chain Branch (SCB)) Having 6 or Less Carbon Atoms)
The sum total of the number of branches having 6 or less carbon atoms calculated above is determined as the number of short-chain branches (SCB).

Example 1

A 0.4-liter autoclave equipped with a stirrer was dried under reduced pressure and the inside of the autoclave was replaced with argon. Subsequently, the autoclave was vacuumized and toluene (82.2 ml) was placed in the autoclave. The temperature of the system was elevated to 80° C. Subsequently, a hexane solution (4.1 ml) of methylaluminoxane (PMAO-s, manufactured by Tosoh Finechem Corporation) having the concentration of 2.45 mmol/ml was supplied to the autoclave. Subsequently, ethylene was introduced into the autoclave so that the partial pressure thereof reaches at 0.5 MPa to stabilize the system. Then, catalytic component 1 (7.0 mg) and toluene (3.7 ml) were supplied to the autoclave to initiate polymerization. The polymerization was carried out at 80° C. for 30 minutes. During the polymerization, ethylene gas was continuously supplied so as to maintain the total pressure in the autoclave constant. Thirty minutes after the initiation of the polymerization, ethylene within the autoclave was purged and the content was taken out from the autoclave. The content was deashed with ethanol-hydrochloric acid and filtrated to obtain polymer (6.5 g). The activity was 1,900 g polymer/h per 1 g of catalytic component 1. Furthermore, the relationship between the storage modulus (G') and the loss modulus (G") at 190° C. obtained in the dynamic viscoelasticity measurement was investigated to reveal that the relationship of G'>G" was constantly obtained in the angular frequency range of from 0.1 to 10000. The results of the determination of the structure and physical properties of the polymer thus obtained are shown in Table 1.

Example 2

A 5-liter autoclave equipped with a stirrer was dried under reduced pressure and the inside of the autoclave was replaced with argon. Subsequently, the autoclave was vacuumized and toluene (1000 ml) was placed in the autoclave. The temperature of the system was elevated to 80° C. Subsequently, a hexane solution (4.1 ml) of methylaluminoxane (PMAO-s, manufactured by Tosoh Finechem Corporation) having the concentration of 2.45 mmol/ml was supplied to the autoclave. Subsequently, ethylene was introduced into the autoclave so that the partial pressure thereof reaches at 0.5 MPa to stabilize the system. Then, a toluene solution (4.5 ml (9 mmol, 4.1 mg)) of complex 2 having the concentration of 2 μmol/ml and a toluene solution (1 ml (1 μmol, 0.46 mg)) of complex 1 having the concentration of 1 μmol/ml were supplied to the autoclave to initiate polymerization. The polymerization was performed at 80° C. for 30 minutes. During the polymerization, ethylene gas was continuously supplied so as to maintain the total pressure in the autoclave constant. Thirty minutes after the initiation of the polymerization, ethylene within the autoclave was purged and the content was taken out from the autoclave. The content was deashed with ethanol-hydrochloric acid and filtrated to obtain polymer (6.2 g). The activity was 2,700 g polymer/h per 1 g of the transition metal complexes (total of complex 1 and complex 2). Furthermore, the relationship between the storage modulus (G') and the loss modulus (G") at 190° C. obtained in the dynamic viscoelasticity measurement was investigated to reveal that the relationship G'>G" was constantly obtained in the angular frequency range of from 0.1 to 10000. The results of the determination of the structure and physical properties of the polymer thus obtained are shown in Table 1.

Example 3

A 0.4-liter autoclave equipped with a stirrer was dried under reduced pressure and the inside of the autoclave was replaced with argon. Subsequently, the autoclave was vacuumized and toluene (80 ml) was placed in the autoclave. The temperature of the system was elevated to 40° C. Subsequently, a toluene solution (1 ml) of methylaluminoxane (TMAO, manufactured by Tosoh Finechem Corporation) having a concentration of 2.5 mmol/ml was supplied to the autoclave. Subsequently, ethylene was introduced into the autoclave so that the partial pressure thereof reaches at 0.5 MPa to stabilize the system. Then, a toluene solution (0.4 ml (0.4 μmol, 0.18 mg)) of complex 3 having the concentration of 1 μmol/ml was supplied to the autoclave to initiate polymerization. The polymerization was performed at 40° C. for 30 minutes, and thereafter the temperature of the system was elevated to 80° C. Thirty minutes after the initiation of the temperature elevation, a toluene solution (2 ml) of methylaluminoxane (TMAO, manufactured by Tosoh Finechem Corporation) having the concentration of 2.5 mmol/ml and a toluene solution (1 ml (1 μmol, 0.46 mg)) of complex 2 having the concentration of 1 μmol/ml were supplied and the polymerization was performed for further 30 minutes. During the polymerization, ethylene gas was continuously supplied so as to maintain the total pressure in the autoclave constant. Thereafter, ethylene within the autoclave was purged and the content was taken out from the autoclave. The content was deashed with ethanol-hydrochloric acid and filtrated to obtain polymer (5.3 g). The activity was 5,100 g polymer/g catalyst/h per 1 g of the transition metal complexes (total of complex 3 and complex 2). Furthermore, the relationship between the storage modulus (G') and the loss modulus (G") at 190° C. obtained in the dynamic viscoelasticity measurement was investigated to reveal that the relationship G'>G" was constantly obtained in the angular frequency range of from 0.1 to 10000. The results of the determination of the structure and physical properties of the polymer thus obtained are shown in Table 1.

Example 4

A 0.4-liter autoclave equipped with a stirrer was dried under reduced pressure and the inside of the autoclave was replaced with argon. Subsequently, the autoclave was vacuumized and toluene (80 ml) was placed in to the autoclave. The temperature of the system was elevated to 40° C. Subsequently, a toluene solution (1 ml) of methylaluminoxane (TMAO, manufactured by Tosoh Finechem Corporation) having the concentration of 2.5 mmol/ml was supplied to the autoclave. Subsequently, ethylene was introduced into the autoclave so that the partial pressure thereof reaches at 0.5 MPa to stabilize the system. Then, a toluene solution (0.2 ml, (0.1 μmol, 0.053 mg)) of complex 4 having the concentration of 0.5 μmol/ml was supplied to the autoclave to initiate polymerization. The polymerization was performed at 40° C. for 30 minutes, and thereafter the temperature of the system was elevated to 80° C. Thirty minutes after the initiation of the temperature elevation, a toluene solution (2 ml) of methylaluminoxane (TMAO, manufactured by Tosoh Finechem Corporation) having the concentration of 2.5 mmol/ml and a toluene solution (1 ml (2 μmol, 0.92 mg)) of complex 2 having the concentration of 1 μmol/ml were supplied and the polymerization was performed for further 30 minutes. During the polymerization, ethylene gas was continuously supplied so as to maintain the total pressure of the autoclave constant. Thereafter, ethylene within the autoclave was purged and the content was taken out from the autoclave. The content was deashed with ethanol-hydrochloric acid and filtrated to obtain polymer (7.0 g). The activity was 4,800 g polymer/g catalyst/h per 1 g of the transition metal complexes (total of complex 3 and complex 2). Furthermore, the relationship between the storage modulus (G') and the loss modulus (G") at 190° C. obtained in the dynamic viscoelasticity measurement was investigated to reveal that the relationship G'>G" was constantly obtained in the angular frequency range of from 0.1 to 10000. The results of the determination of the structure and physical properties of the polymer thus obtained are shown in Table 1.

Example 5

A 0.4-liter autoclave equipped with a stirrer was dried under reduced pressure and the inside of the autoclave was replaced with argon. Subsequently, the autoclave was vacuumized and toluene (80 ml) was placed in the autoclave. The temperature of the system was elevated to 40° C. Subsequently, a toluene solution (1 ml) of methylaluminoxane (TMAO, manufactured by Tosoh Finechem Corporation) having the concentration of 2.5 mmol/ml was supplied to the autoclave. Subsequently, ethylene was introduced into the autoclave so that the partial pressure thereof reaches at 0.5 MPa to stabilize the system. Then, a toluene solution (0.13 ml, (0.13 μmol, 0.060 mg)) of complex 1 having the concentration of 1 mmol/ml was supplied to initiate polymerization. The polymerization was performed at 40° C. for 30 minutes, and thereafter the temperature of the system was elevated to 80° C. Thirty minutes after the initiation of the temperature elevation, a toluene solution (2 ml) of methylaluminoxane (TMAO, manufactured by Tosoh Finechem Corporation) having the concentration of 2.5 mmol/ml and a toluene solution (1 ml, (1 μmol, 0.46 mg)) of complex 2 having the concentration of 1 μmol/ml were supplied and the polymerization was performed for further 30 minutes. During the polymerization, ethylene gas was continuously supplied so as to maintain the total pressure in the autoclave constant. Thereafter, ethylene within the autoclave was purged and the content was taken out from the autoclave. The content was deashed with ethanol-hydrochloric acid and filtrated to obtain polymer (5.3 g). The activity was 6,800 g polymer/g catalyst/h per 1 g of the complexes (total of complex 1 and complex 2). Furthermore, the relationship between the storage modulus (G') and the loss modulus (G") at 190° C. obtained in the dynamic viscoelasticity measurement was investigated to reveal that the relationship G'>G" was constantly obtained in the angular frequency range of from 0.1 to 10000. The results of the determination of the structure and physical properties of the polymer thus obtained are shown in Table 1.

It should be noted that all the polymers obtained in Examples 1 to 5 were non-crosslinked polymers. No solvent-insoluble portion was observed in the GPC measurement (and the viscosity measurement).

Comparative Example 1

A commercially available linear low-density polyethylene, Sumikathene-L FS 150 (manufactured by Sumitomo Chemical Co., Ltd.) was used. The results of the determination of the structure and physical properties are shown in Table 1. Furthermore, the relationship between the storage modulus (G') and the loss modulus (G") at 190° C. obtained in the dynamic viscoelasticity measurement was investigated to reveal that the intersection ($\omega_x$) between G' and G" curves was at 110 and that the relationship G'>G" was constantly obtained at $\omega_x$ and higher frequencies.

Comparative Example 2

A commercially available high-pressure low-density polyethylene, Sumikathene-F200 (manufactured by Sumitomo Chemical Co., Ltd.) was used. The results of the determination of the structure and physical properties are shown in Table 1. Furthermore, the relationship between the storage modulus (G') and the loss modulus (G") at 190° C. obtained in the dynamic viscoelasticity measurement was investigated to reveal that the intersection ($\omega_x$) between G' and G" curves was at 25 and that the relationship G'>G" was constantly obtained at $\omega_x$ and higher frequencies.

Comparative Example 3

A commercially available high-density polyethylene, HI-ZEX 2200J (manufactured by Prime Polymer Co., Ltd.) was used. The results of the determination of the structure and physical properties are shown in Table 1. Furthermore, the relationship between the storage modulus (G') and the loss modulus (G") at 190° C. obtained in the dynamic viscoelasticity measurement was investigated to reveal that the relationship G'<G" was constantly obtained in the angular frequency range of from 0.1 to 10000.

Comparative Example 4

A commercially available high-density polyethylene, HI-ZEX 7000F (manufactured by Prime Polymer Co., Ltd.) was used. The results of the determination of the structure and physical properties are shown in Table 1. Furthermore, the relationship between the storage modulus (G') and the loss modulus (G") at 190° C. obtained in the dynamic viscoelasticity measurement was investigated to reveal that the intersection ($\omega_x$) between G' and G" curves was at 1.0 and that the relationship G'>G" was constantly obtained $\omega_x$ and higher frequencies.

Comparative Example 5

A commercially available high-density polyethylene, HI-ZEX 8000F (manufactured by Prime Polymer Co., Ltd.) was used. The results of the determination of the structure and physical properties are shown in Table 1. Furthermore, the relationship between the storage modulus (G') and the loss modulus (G") at 190° C. obtained in the dynamic viscoelasticity measurement was investigated to reveal that the intersection ($\omega_x$) between G' and G" curves was at 0.6 and that the relationship G'>G" was constantly obtained at $\omega_x$ and higher frequencies.

TABLE 1

| | SCB (/1000C) | LCB (/1000C) | Ea (KJ/mol) | G'/G" (190° C., ω = 0.11) | G' (190° C., ω = 0.11) | [η] (dl/g) | Mw | MWD | Mz/Mw | η* | τ (sec) | λ of Blended Material |
|---|---|---|---|---|---|---|---|---|---|---|---|---|
| Example 1 | 3.4 | 1.1 | 134 | 1.87 | 17899 | 1.35 | 127263 | 10.5 | 4.1 | 1499 | 71 | — |
| Example 2 | 2.2 | 0.26 | 65 | 1.98 | 22624 | 2.23 | 201780 | 24.2 | 7.5 | 1096 | 125 | 2.1 |
| Example 3 | 0.7 | 0.21 | 110 | 2.04 | 21088 | 1.25 | 91686 | 2.8 | 5.6 | 2129 | 70 | 1.8 |
| Example 4 | 2.6 | 0.21 | 87 | 1.81 | 14533 | 1.72 | 135051 | 3.1 | 3.8 | 1144 | 330 | 2.1 |
| Example 5 | 12 | 0.35 | 54 | 1.13 | 7598 | 1.35 | 88677 | 5.6 | 3.0 | 1634 | 23 | 1.7 |
| Comparative Example 1 | 19 | 0 | 28 | 0.06 | 54 | 1.70 | 131900 | 3.4 | 2.6 | 2431 | 0.1 | 1.0 |
| Comparative Example 2 | 15.2 | 1.01 | 63 | 0.20 | 182 | 0.90 | 72200 | 3.8 | 2.3 | 709 | 0.9 | 1.4 |
| Comparative Example 3 | 0.2 | 0.00 | 28 | 0.16 | 44 | 1.30 | 98400 | 7.1 | 9.4 | 610 | 0.4 | 1.0 |
| Comparative Example 4 | 2.16 | 0.00 | 30 | 0.71 | 6343 | 2.93 | 260200 | 34.2 | 8.4 | 2379 | 5.2 | 1.0 |
| Comparative Example 5 | 4.1 | 0.00 | 30 | 0.79 | 10226 | 3.26 | 316800 | 28.8 | 7.8 | 2851 | 5.9 | 1.2 |

INDUSTRIAL APPLICABILITY

The ethylenic polymer provided by the present invention has a long characteristic relaxation time and can be suitably used in a wide variety of applications in various industrial fields such as shrink packaging films and thus is highly useful in industries.

The invention claimed is:

1. An ethylenic polymer satisfying the following requirements:
  (a) the ethylenic polymer is a non-crosslinked ethylenic polymer;
  (b) the number of long-chain branches (LCB) per 1000 carbon atoms is 0.1 or more and 1.5 or less;
  (c) the intrinsic viscosity [η] is 1.0 dl/g or more and 3.0 dl/g or less; and
  (d) the ratio (G'/G") of the storage modulus (G') to the loss modulus (G"), determined by dynamic viscoelasticity measurement at 190° C. and at an angular frequency of 0.1 rad/sec is 0.8 or more and 4.0 or less.

* * * * *